(12) United States Patent
Barasch et al.

(10) Patent No.: US 7,776,824 B2
(45) Date of Patent: Aug. 17, 2010

(54) NGAL FOR REDUCTION AND AMELIORATION OF ISCHEMIC AND NEPHROTOXIC INJURIES

(75) Inventors: Jonathan M. Barasch, New York, NY (US); Prasad Devarajan, Cincinnati, OH (US); Kiyoshi Mori, New York, NY (US)

(73) Assignees: The Trustees of Columbia University, New York, NY (US); Children's Hospital Medical Center, Cincincati, OH (US)

( * ) Notice: Subject to any disclaimer, the term of this patent is extended or adjusted under 35 U.S.C. 154(b) by 792 days.

(21) Appl. No.: 11/123,364

(22) Filed: May 6, 2005

(65) Prior Publication Data

US 2005/0261191 A1 Nov. 24, 2005

Related U.S. Application Data

(60) Provisional application No. 60/568,645, filed on May 6, 2004, provisional application No. 60/615,566, filed on Oct. 1, 2004.

(51) Int. Cl.
*A61K 38/04* (2006.01)
*A01N 1/00* (2006.01)
*A01N 1/02* (2006.01)

(52) U.S. Cl. .......................................... 514/12; 435/1.1

(58) Field of Classification Search .................... 514/12
See application file for complete search history.

(56) References Cited

U.S. PATENT DOCUMENTS

| | | | |
|---|---|---|---|
| 6,114,123 A | 9/2000 | Murry et al. | |
| 6,447,989 B1 | 9/2002 | Comper | |
| 6,664,385 B1 | 12/2003 | Sanicola-Nadel et al. | |
| 2004/0132984 A1 | 7/2004 | Dieckmann et al. | |
| 2004/0219603 A1 | 11/2004 | Devarajan et al. | |

FOREIGN PATENT DOCUMENTS

| | | |
|---|---|---|
| WO | WO 03/029462 A1 | 4/2003 |
| WO | WO 2004/005544 | 1/2004 |

OTHER PUBLICATIONS

Horwitz, L.D., et al. Apr. 1998 Proc. Natl. Acad. Sci. 95: 5263-5268.*
Singbartl, K., et al. 2000 FASEB J 14: 48-54.*
Kubes, P., et al. 1995 J Clin Invest 95: 2510-2519.*
Hard, G. 1998 Toxicologic Pathology 26(1): 104-112.*
Davarajan, P., et al., The Von Hippel-Lindau gene product inhibits renal cell apoptosis via Bcl-2-dependent pathways, J. Biol. Chem., No. 44, 276: 40599-40605, Nov. 2, 2001.
Del Rio, M., et al, The death domain of kidney ankyrin interacts with Fas and promotes Fas-mediated cell death in renal epithelia, J. Am. Soc. Nephrol., 15: 41-51, 2004.
Feldenberg, L.R., et al., Partial ATP deletion induces Fas- and caspase- mediated apoptosis in MDCK cells, Am. J. Physiol., 276 (Renal Physiol 45): F837-F846, 1999.
Goetz, D. H., et al., The Neutrophil Lipocalin NGAL is a Bacteriostatic Agent that Interferes with Siderophore-Mediated Iron Acquisition, Molecular Cell, vol. 10, 1033-1043, Nov. 2002.
Holmes, M., et al., Siderocalin (Lcn 2) Also Binds Carboxymycobactins, Potentially Defending against Mycobacterial Infections through Iron Sequestration, Structure, vol. 13, 29-41, Jan. 2005.
Kelly, K.J., et al., Guanosine supplementation reduces apoptosis and protects renal function in the setting of ischemic injury, J. Clin. Invest., No. 9, vol. 108: 1291-1298, Nov. 2001.
Kjeldsen, L., et al., Isolation and Primary Structure of NGAL, a Novel Protein Associated with Human Neutrophil Gelatinase, The Journal of Biological Chemistry, vol. 268, No. 14, Issue of May 15, pp. 10425-10432, 1993.
Kjeldsen, L., et al., Human neutrophil gelatinase-associated lipocalin and homologous proteins in rat and mouse, Biochim. Biophys. Acta, 1482:272-283, 2000.
Li, Jau-Yi, et al., Detection of intracellular iron by its regulatory effect, Am. J. Physiol. Cell Physiol. 287: C1547-C1559, 2004.
Li Yan, et al., The High Molecular Weight Urinary Matrix Metalloproteinase (MMP) Activity is a Complex of Gelantinase B/MMP-9 and Neutrophil Gelantinase-associated Lipocalin (NGAL), J.Biol. Chem., Oct. 5, vol. 276, No. 40, pp. 37258-37265, 2001.
Mishra, J., et al, Amelioration of Ischemic Acute Renal Injury by Neutrophil Gelatinase-Associated Lipocalin; J. Am. Soc. Nephrol. 15:3073-3082, 2004.
Mishra, J., et al, Neutrophil gelatinase-associated lipocalin (NGAL) as a biomarker for acute renal injury after cardiac surgery, The Lancet, vol. 365, Apr. 2, 2005, pp. 1231-1238.
Mishra, J., et al., Identification of Neutrophil Gelatinase-Associated Lipocalin as a Novel Early Urinary Biomarker for Ischemic Renal Injury, J. Am. Soc. Nephrol 14: 2534-2543, 2003.
Mishra, J., et al., Neutrophil Gelatinase-Associated Lipocalin: A Novel Early Urinary Biomarker for Cisplatin Nephrotoxicity, Am. J. Nephrol. 2004; 24:207-315.
Mori, J., et al., Endocytic delivery of lipocalin-siderophore-iron complex rescues the kidney from ischemia-reperfusion injury, J. Clin. Invest 115:610-621 (2005.).

(Continued)

*Primary Examiner*—Maryam Monshipouri
*Assistant Examiner*—Marsha M Tsay
(74) *Attorney, Agent, or Firm*—Hasse & Nesbitt LLC; Daniel F. Nesbitt

(57) ABSTRACT

Use of neutrophil gelatinase-associated lipocalin (NGAL) as a therapeutic and in a method of treating, reducing, or ameliorating an injury selected from an ischemic injury, an ischemic-reperfusion injury, and a toxin-induced injury, to an organ in a patient. The invention includes administering to the patient NGAL in an amount effective to treat, reduce or ameliorate ischemic, ischemic-reperfusion, or toxin-induced injury to the organ, such as the kidney. A siderophore can be co-administered with the NGAL. The invention also relates to administering a sideophore to enhance a response to secretion of NGAL following an ischemic or toxin-induced injury to an organ in a patient.

23 Claims, 31 Drawing Sheets

OTHER PUBLICATIONS

Yang, J., et al., An iron delivery pathway mediated by a lipocalin, Mol. Cell., vol. 10: 1045-1056, Nov. 2002.

Yang, J., et al., Iron, lipocalin, and kidney epithelia, Am. J. Physiol Renal Physiol 285: F9-F18, 2003.

U.S. Appl. No. 10/811,130, filed Mar. 26, 2004, DeVarajan, et al.

U.S. Appl. No. 11/096,113, filed Mar. 31, 2005, DeVarajan, et al.

Blaser, J., et al., A sandwich enzyme immunoassay for the determination of neutrophil lipocalin in body fluids; *Clinica Chimica Acta* 235 (1995) pp. 137-145.

Devarajan, P, Novel biomarkers for the early prediction of acute kidney injury; *Cancer Therapy* (2005); vol. 3, pp. 477-488.

Kramer, A. A., et al.; Renal ischemia/reperfusion leads to macrophage-mediated increase in pulmonary vascular permeability; *Kidney International* (1999), vol. 55; pp. 2362-2367.

Matthaeus, T. et al., Co-Regulation of Neutrophil Gelatinase-Associated Lipocalin and Matrix Metalloproteinase-9 in the Postischemic Rat Kidney, *Pathophysiology of Renal*, A4112, SUI-0348 (PS).

Matthaeus, T., et al., Acute Ischemic Renal Failure Induces Expression of Neutrophil Gelatinase-Associated Lipocalin and Matrix Metalloproteinase-9 in Damaged Tubuli, *Kidney Blood Press Res* (2001), vol. 24, Congress of Nephrology 2001, p. 342.

Ohlsson, S., et al., Increased circulating levels of proteinase 3 in patients with anti-neutrophilic cytoplasmic autoantibodies-associated systemic vasculitis in remission, *Clin Exp Immunol* (2003): vol. 131 pp. 528-535.

Rabb, H., et al., Acute renal failure leads to dysregulation of lung salt and water channels; *Kidney International* (2003); vol. 63; pp. 600-606.

Schmidt-Ott, K. M., et al.; Neutrophil gelatinase-associated lipocalin-mediated iron traffic in kidney epithelia; *Current Opinion in Nephrology and Hypertension* (2006); vol. 15:000-000 pp. 1-8.

U.S. Appl. No. 11/374,285, filed Oct. 13, 2005, Barasch, et al.

Devarajan, P. et al., Gene Expression in Early Ischemic Renal Injury: Clues Toward Pathogenesis, Biomarker Discovery, and Novel Therapeutics, Molecular Genetics and Metabolism, Dec. 2003, vol. 80, Issue 4, pp. 365-376.

Eichler, I., Human neutrophil lipocalin, a highly specific marker for acute exacerbation in cystic fibrosis, Eur Respir J, Nov. 1999, vol. 14, pp. 1145-1149.

Han, W. K. et al., Kidney Injury Molecue-1(KIM-1): A novel biomarker for human renal proximal tubule injury; Kidney International, Jul. 2002, vol. 62, Issue 1, pp. 237-244.

Han, W. K. et al., Urinary biomarkers in the early diagnosis of acute kidney injury, Kidney International, http://kidney.international.org, 2007, pp. 1-7. (online Dec. 5, 2007).

Ichimura, T. et al., Kidney Injury Molecule-1 (KIM-1), a Putative Epithelial Cell Adhesion Molecule Containing a Novel Immunoglobulin Domain, Is Up-regulated in Renal Cells after Injury, The Journal for Biological Chemistry, Feb. 13, 1998.vol. 273, No. 7, pp. 4136-4142.

Muramatsu, Y., et al., Early detection of cysteine rich protein 61 (CYR61, CCNI) in urine following renal ischemic reperfusion injury, Kidney International, Nov. 2002, vol. 62, Issue 5, pp. 1601-1610.

\* cited by examiner

NGAL FOR REDUCTION AND AMELIORATION OF ISCHEMIC AND NEPHROTOXIC INJURIES

CROSS-REFERENCE TO RELATED APPLICATIONS

This application claims the benefit of U.S. Provisional Application Nos. 60/586,645, filed May 6, 2004 and 60/615,566, filed Oct. 1, 2004.

INTERESTS

This invention was made with Government support awarded by the National Institute of Health (NIH)/National Institute of Diabetes and Digestive and Kidney Diseases, under Grant Nos. DK53289, DK52612, and DK070163. The Government has certain rights in this invention.

FIELD OF THE INVENTION

The present invention relates to methods of reducing or ameliorating ischemic and nephrotoxic injury in organs. The invention further relates to the treatment of patients suffering from various diseases that are associated with ischemic and toxin-induced injury or insult. The invention further relates to the treatment of patients suffering from acute or chronic kidney injury.

BACKGROUND OF THE INVENTION

A decrease in oxygen flow to an organ, called ischemia, triggers a complex series of events that affect the structure and function of virtually every organelle and subcellular system of the affected cells. Ischemia-reperfusion (resumption of blood flow) injury leads to the production of excessive amounts of reactive oxygen species (ROS) and reactive nitrogen species (RNS), thus causing oxidative stress which results in a series of events such as alterations in mitochondrial oxidative phosphorylation, depletion of ATP, an increase in intracellular calcium and activation of protein kinases, phosphatases, proteases, lipases and nucleases leading to loss of cellular function/integrity. It has been shown that the inflammatory response induced by ischemia followed by reperfusion is largely responsible for tissue and organ damage.

Ischemic-reperfusion injury is a serious problem in organ transplantation because the harvested organ is removed from the body, isolated from a blood source, and thus deprived of oxygen and nutrients for an extended period of time. A critical problem to be addressed in present-day kidney transplantation procedures is the relatively high incidence of delayed graft function (DGF) due to acute tubular necrosis (ATN) following surgery. Illustratively, DGF affects about 20-35% of kidney transplants in many transplant centers and is the most common complication of the immediate post-operative period in renal transplantation. Although the incidence and definition of DGF vary among transplant centers, the consequences most frequently involve a prolonged hospital stay, additional invasive procedures and additional costs to the patient and health-care system. Delay in graft function not only affects the individual patient, it also impacts the infrastructure for organ procurement and sharing as a consequence of the drain it places on the available organ supply. DGF also increases the risk of early acute rejection episodes and increases early graft loss from chronic rejection.

With current preservation methods, cold ischemia resulting from organ preservation has been identified as a major risk factor in causing DGF after transplant. For kidneys, cold ischemia times in excess of 24 hours are associated with a significantly increased risk of DGF. In the mid-1960's, cold preservation of kidneys was effectively achieved by using machine perfusion and a solution derived from cryoprecipitated plasma. Thereafter, by simple cold-storage methods were introduced and involved the use of a cold crystalloid solution. Since the early successes with kidneys, preservation solutions have evolved into entirely synthetic defined media designed to prevent cold ischemic injury by suppression of cell swelling and provision of metabolic support. An early synthetic solution, a lactobionate-based solution (UW) from the University of Wisconsin has been used for both pancreas and liver. With the advent of synthetic and serum-free preservation formulations, the quality and duration of feasible organ preservation have improved. Despite this, however, clinical data on DGF in kidneys and other problems involving renal cell structure and morphology clearly demonstrate that such solutions are not completely successful in preventing ischemic injury or insult.

In addition, acute renal failure (ARF) secondary to ischemic or nephrotoxic injury also remains a common and potentially devastating problem in clinical nephrology, with a persistently high rate of mortality despite significant advances in supportive care. Over several decades, a number of studies have illuminated the roles of persistent vasoconstriction, tubular obstruction, cellular structural and metabolic alterations, and the inflammatory response in the pathogenesis of ARF. Treatments and remedies for ARF have been hampered by the multifaceted response of the kidney to ischemia, as well as a lack of early markers for ARF. Recent advances in cellular and molecular biology of ischemic and nephrotoxic renal injury have shown that proximal tubule cells undergo a complex temporal sequence of events, including loss of cell polarity, cell death due to apoptosis and necrosis, de-differentiation and proliferation of viable cells, and re-establishment of the epithelial phenotype.

As a result of ischemic or nephrotoxic damage, cells may die through two different processes. Apoptosis or programmed cell death ("cell suicide") is a physiological mechanism for removing senescent, damaged or abnormal cells that affects individual cells. Apoptosis is initiated by an endonuclease and is characterized by DNA fragmentation into multiples of 180-200 base pairs. Apoptotic cells are ingested by macrophages or neighboring cells without release of proteolytic enzymes or toxic oxygen species and the process is not accompanied by inflammation. By contrast, necrosis ("cell murder") is a pathological process that affects populations of cells and results in focal tissue destruction, inflammation and often serious systemic consequences. Apoptotic cell death has now been shown to play an important role in an increasing array of kidney diseases, including ischemia, ischemia-reperfusion, nephrotoxins, polycystic kidney disease, obstruction, and glomerular diseases. Down-regulation of apoptosis therefore offers a unique and powerful therapeutic approach to the amelioration of several acute and chronic kidney injuries.

An individual is considered to have acute renal failure when the patient's serum creatinine value either (1) increased by at least 0.5 mg/dL when the baseline serum creatinine level was less than 2.0 mg/dL; (2) increased by at least 1.5 mg/dL when the baseline serum creatinine level was greater than or equal to 2.0 mg/dL; or (3) increased by at least 0.5 mg/dL, regardless of the baseline serum creatinine level, as a consequence of exposure to radiographic agents.

cDNA microarray techniques have allowed the identification of neutrophil gelatinase-associated lipocalin (NGAL) as a highly induced transcript in the kidney early after ischemic and nephrotoxic injury. The role of NGAL in the kidney has yet to be elucidated. NGAL is a member of the lipocalin family of proteins and is characterized as a secreted 25 kDa glycoprotein found in granules of human neutrophils. (Kjeldsen et al, 1993, J. Biol. Chem. 268:10425-10432). Lipocalins, which are able to bind small lipophilic substances, share a common three-dimensional β-barrel structure which functions, in at least some lipocalins, to bind lipophilic ligands, e.g., steroid, bilin, retinoid, or other lipid. Murine forms of NGAL (homologs) from mice and rats are known. In mice, NGAL has been designated as NGAL, 24p3 protein, SIP24, P25, lipocalin 2, and uterocalin. NGAL in rats is known as NGAL or alpha 2-microglobulin. A full-length cDNA encoding human NGAL protein has been cloned and sequenced. The human NGAL gene, which includes seven exons and six introns, has also been cloned and sequenced, and its expression in various tissues has been analyzed. The human NGAL gene encodes a polypeptide of 197 amino acids, with a 19- or 20-amino acid signal sequence, and a mature NGAL polypeptide containing 178 amino acids. The motifs Gly-X-Trp (amino acids 48-50 in mature human NGAL) and Thr-Asp/Asn-Tyr (amino acids 132-134 in mature human NGAL) are present in all known lipocalins. On the basis of X-ray crystallography, it has been suggested that these motifs are important in the tertiary β-barrel structure shared among the lipocalins. The cysteine residues 95 and 194 in the human NGAL sequence are conserved, and have been reported to form an intramolecular disulfide bridge. Human NGAL contains a single N-glycosylation site (an asparagine residue) at position 65 of the mature amino acid sequence (approximately position 84 or 85 of the pre-NGAL polypeptide).

A mechanism that may underlie ATN is mis-localized iron. Unbound iron can catalyze the conversion of $H_2O_2$ to OH and $OH^-$ (the Haber-Weiss reaction) or form reactive ferryl or perferryl species. These ions mutagenize many types of molecules including lipids, nucleotides and the DNA backbone. Catalytic iron, released from free hemoglobin and myoglobin into urine or blood, and peroxidized lipids have been documented in many forms of acute renal failure, including chemotherapy, ischemia-reperfusion, transplant ischemia, and in proteinuria-mediated tubular damage. Preloading animals with iron worsens the disease, and conversely chelating iron with deferoxamine or bacterial siderophores blunts the damage. Iron-catalyzed damage is thought to be one of the earliest events in kidney dysfunction and is likely to be important in other organs, including the heart and the liver (See Mori et al: Endocytic delivery of lipocalin-siderophore-iron complex rescues the kidney from ischemia-reperfusion injury. J Clin Invest 115:610-621, 2005).

Cells acquire iron from carrier proteins (such as transferrin) and by cell surface iron transporters (such as divalent metal transporter I). Intracellular iron is controlled by the actions of the iron responsive proteins (such as IRP1, IRP2), the ferritin complex and heme oxygenase I. Because IRPs are modulated by hypoxia, oxidative stress, and phosphorylation, changes in their activity may play an important role in ischemic disease, by regulating formation of ferritin complexes, which protect cells from iron mediated damage. Ferritin is an iron-phosphorous-protein complex, comprising approximately 23% iron, formed in the intestinal mucosa. Ferritin is the storage form of iron in tissues such as liver, spleen, and bone marrow. Hemoglobin and myoglobin molecules in blood and muscle, respectively, require iron-binding to catalyze transfer of oxygen to cells. However, few other aspects of iron trafficking, storage or metabolism are known in ischemic cells or in other types of tissue damage, despite the primacy of catalytic iron in their pathogenesis.

Despite the many pathways of producing ATN, a number of investigators have discovered general underlying mechanisms of proximal tubule cell damage. These have included the release of cytokines. One idea is that ischemic cells and tubular toxins such as free myoglobin and hemoglobin produce high concentrations of iron locally in the nephron. It is thought that this iron is catalytically active, and produces oxygen radicals. Evidence that iron catalyzed cell damage is pathogenic and leads to proximal tubular dysfunction includes the finding that tubular damage is blunted by infusions of iron chelators. Additional support for the idea that iron is central to the mechanism of organ dysfunction after ischemia comes from experiments that used iron free-bacterially derived, iron chelators, called siderophores, to blunt the effects of ischemia-reperfusion injury in an in vitro model of cardiac ischemia. Each of these general mechanisms is thought to be the principle pathogenic event during different stages of ATN. Iron catalyzed damage is thought to be one of the earliest events in kidney dysfunction.

It is currently unknown how the proximal tubule captures NGAL. Indeed an unambiguous identification of receptors for most lipocalins is still lacking. Perhaps megalin, which is necessary for reclamation of RBP, is also the NGAL receptor (Christensen et al., 1999, *J Am Soc Nephrol.* 10(4) 685-95). In fact, knockout of megalin leads to the appearance of NGAL in the urine, but these animals were also, unexpectedly, found to have much higher levels of NGAL message (Hilpert et al., 2002, *Kidney Int.* 62(5)1672-81), suggesting that urinary NGAL might have derived from local synthesis rather than a failure to capture the filtered load. Despite this ambiguity, NGAL is similar to other lipocalins, such as RBP and α-2u globulin lipocalin (see Borghoff et al., 1990, *Annu Rev Pharmacol Toxicol.* 30:349-67), which enter the cell by a megalin pathway and traffic to lysosomes for degradation. These data contrast with the trafficking of NGAL in cell lines that do not express megalin (such as embryonic kidney cells) and where the protein escapes degradation (see Yang et al., 2002, *Mol. Cell* 10(5):1045-56). Similarly, transferrin is also degraded after delivery to lysosomes by a megalin-cubulin based pathway in the proximal tubule (see Kozyraki et al., 2001, *Proc. Natl Acad Sci USA* 98(22)12491-6), whereas it usually recycles in cell lines. Hence it is reasonable to propose that after filtration, NGAL is captured by megalin and degraded by the proximal tubule and is not recycled. This hypothesis is supported by the observation that full length NGAL does not reappear in the blood at delayed time points post-injection.

There remains a need for compositions and methods suitable for preventing, reducing, or ameliorating ischemic injury, e.g., cold ischemic injury, in organs such as the kidney. Such compositions would be useful both in treating a patient's original organs, as well as organs used for transplantation. Also needed are new biomarkers that can be used to detect toxic damage to cells, for example nephrotoxicity, in patients following drug administration. New and improved methods of treating and reducing ischemic-reperfusion injury to tissues and organs caused by organ transplantation, and of treating and reducing structural and metabolic alterations of organ cells, are clearly useful and important to practitioners and patients alike.

SUMMARY OF THE INVENTION

The present invention relates to neutrophil gelatinase-associated lipocalin (NGAL) and its use in compositions and methods for treating, reducing, ameliorating, or preventing a condition, injury or disease, typically selected from an ischemic, an ischemia-reperfusion, or a toxin-induced injury in an organ. The invention also relates to a method of administering to a patient or subject NGAL in an amount effective to treat, reduce, ameliorate or prevent the condition, injury or disease. The injury can include a renal injury associated with conditions, treatments, therapies, or diseases that predispose a patient to ischemic renal injury, a renal tubule injury, or necrosis/apoptosis. The injury can include acute (including but not limited to shock, stroke, sepsis, trauma, infection, inflammation) or chronic (including but not limited to hypertension, diabetes, heart failure, lupus, infections, inflammations) kidney conditions.

The present invention also provides a method of ameliorating reduction in kidney NGAL function induced by ischemia-reperfusion injury in a patient by administering NGAL to the patient in an amount effective to ameliorate the reduction of kidney function. In accordance with this aspect, NGAL administration reduces high levels of serum or plasma creatinine following ischemia-reperfusion injury. The amount of NGAL administered is effective to prevent or ameliorate cell death.

The invention further provides a method of enhancing renal re-epithelialization or tubular cell proliferation following an ischemic, ischemic-reperfusion, or toxin-induced injury, and in acute or chronic kidney disease, by administering NGAL to a patient in an amount effective to enhance renal re-epithelialization or effect proliferation of tubular cells.

An embodiment of the invention includes the use of NGAL in a method of treating, reducing, preventing or ameliorating acute renal failure (ARF). NGAL has been demonstrated to enhance tubule cell proliferation and reduce or ameliorate tubule cell apoptosis. The methods disclosed can ameliorate the reduction in kidney function in a patient that is induced by an ischemia-reperfusion or toxin-induced injury, and can further be used for treating, reducing, ameliorating or preventing acute renal failure secondary to ischemic injury in the patient.

The invention further provides the use of NGAL in a method for reducing and/or treating delayed graft function (DGF) of a transplanted organ in a patient. In some aspects, DGF is caused by acute tubular necrosis (ATN).

The invention also provides the use of NGAL in a method for transplanting and grafting of an organ into a patient. The use of the method can reduce or ameliorate organ graft or transplant loss or acute rejection by introducing NGAL into one or more of (i) the organ or (ii) a donor thereof, in an amount effective to reduce or ameliorate loss or acute rejection of the organ graft or transplant. In various aspects, the organ is selected from kidney, liver, heart, brain, lung, stomach, intestine, colon, pancreas, blood vessels, bladder, cervix, skin, or a portion or section thereof. In a particular aspect, the organ resides in a cadaverous or living organ donor. In this situation, NGAL can be administered to the patient before, during and/or after the organ is transplanted or grafted into the patient. The organ can be a cadaverous organ, and in those instances in which the organ is obtained from a cadaverous donor, NGAL can be administered to either the cadaver or the extracted organ to prevent injury, insult, or failure of the organ following transplantation. The organ can be a living organ donation, and in those instances NGAL can be administered to the extracted organ to prevent injury, insult, or failure of the organ following transplantation. The organ can be a kidney, liver, heart, brain, lung, stomach, pancreas, blood vessels, bladder, cervix, skin, or a portion or section thereof. In a particular aspect of the present invention, the organ is a kidney.

The present invention also provides the use of NGAL in association with cadaveric and living donor renal transplantation, where oxidant-mediated apoptosis is an important contributor to tubule cell death. In addition to the usual complications of acute renal failure (ARF), ischemia-reperfusion injury in the transplanted kidney is known to result in delayed graft function (DGF), which significantly increases the risk of graft loss and acute rejection. As described herein, NGAL is employed in methods for reducing or ameliorating the adverse ischemic effects associated with organ transplantation. In one embodiment, NGAL can be added to an organ preservation solution, such as is used during cold storage of transplant organs, to ameliorate the DGF that is characteristic of cadaveric kidney transplantation. In accordance with this method, NGAL is at least partially effective even when administered after the ischemic insult. Advantageously, the method affords needed and novel therapeutic treatments of established ischemic conditions, such as ARF, which is an existing, clinically-relevant, adverse event that is commonly associated with a dismal prognosis for the patient. The method of retarding or ameliorating DGF associated with ischemic injury in an organ or graft transplant in a patient includes introducing an amount of NGAL into, or contacting NGAL with, (i) a transplanted organ or graft; (ii) a donor of a transplanted organ; or (iii) both (i) and (ii), in an amount effective to retard or ameliorate DGF, or the loss or acute rejection of the transplanted or grafted organ. Illustratively, and without limitation, the organ or graft for transplant is selected from kidney, liver, heart, brain, lung, stomach, intestine, colon, pancreas, blood vessels, bladder, cervix, skin, or a portion or section thereof. In a particular aspect, the organ is a kidney. More particularly, the kidney transplanted is a cadaveric or living donor kidney. Further, NGAL is a component of the organ preservation solution, e.g., an NGAL-containing organ preservation solution is used during cold storage of the organ transplant.

The present invention further provides a method of reducing, ameliorating, preventing or protecting a patient from renal injury that is associated with conditions, treatments, therapies, or diseases that can predispose a patient to ischemic renal injury. The method comprises administering to the patient an amount of NGAL effective to reduce, ameliorate, prevent or protect the patient from renal injury associated with the patient's condition, treatment, therapy, or disease. Illustrative conditions, treatments, or therapies include without limitation, contrast agent treatment, antibody treatment, antibiotic treatment, organ transplant, kidney transplant, cadaveric kidney transplant, cardiac treatment, cardiac treatment after surgery, or central nervous system treatment. Illustrative diseases according to this aspect include, without limitation, infection, bacterial infection, acute kidney disease, chronic kidney disease, ischemic-reperfusion injury, shock, trauma, sepsis, stroke, cardiac reperfusion injury, cardiopulmonary bypass, open heart surgery, and abdominal surgery.

The invention also provides a method of treating, reducing or ameliorating renal tubule injury or necrosis/apoptosis in a patient, which comprises administering a therapeutically effective amount of NGAL to the patient. According to this aspect, the patient can be affected with acute kidney disease, chronic kidney disease, ischemic-reperfusion injury, organ transplant, toxin-induced injury, ischemia, kidney transplant, shock, trauma, sepsis, stroke, cardiac reperfusion injury, renal tubule injury following cardiopulmonary bypass, renal tubule injury following open heart surgery, renal tubule injury following abdominal surgery, infection, antibiotic treatment, antibody treatment, or contrast agent treatment, for example. In the method, NGAL can function to enhance proliferation of renal tubule cells, since NGAL also directly targets renal proximal tubule cells, resulting in reduction or amelioration of renal tubule injury or necrosis/apoptosis.

The present invention also provides a method of treating, reducing, or ameliorating a toxin-induced injury, including a nephrotoxic injury, to an organ in a patient by administering NGAL to the patient in an amount effective to treat, reduce or ameliorate the toxin-induced injury to the organ. In another aspect, the method of reducing or ameliorating a toxin-induced injury includes co-administering both NGAL and a therapeutic compound that is toxic to the patient, the NGAL being administered in an amount effective to reduce or ameliorate the toxic effect of the therapeutic on the organ.

The present invention also provides a method of treating, reducing, or ameliorating other acute (including but not limited to shock, stroke, sepsis, trauma, infection, inflammation) and chronic (including but not limited to hypertension, diabetes, heart failure, lupus, infections, inflammations) kidney injuries.

In the various methods of the present invention disclosed herein, NGAL can be administered in conjunction with one or more therapeutic agents, such as, for example, vasodilators or oxygen supplying agents. In addition, NGAL can be administered in a physiologically acceptable composition comprising a carrier, diluent, or excipient by various routes of administration, including, without limitation, intravenous or parenteral routes. Further, NGAL can be administered prior to, during, or following ischemia or nephrotoxicity, organ transplant or grafting, or renal tubule insult, damage, or injury, as described herein.

The present invention also provides a method of evaluating a therapeutic for its potential to induce nephrotoxicity by (a) administering a test substance to cause a nephrotoxic injury a mammalian model, such as a mouse; and (b) determining the presence of neutrophil gelatinase-associated lipocalin (NGAL) in a urine or plasma sample of the mammalian model following the administration of the test substance, as an indication that the substance can induce kidney damage. In a particular aspect of this method, NGAL is detected in the urine or plasma within about three hours following administration of the test substance.

The present invention also relates to a composition for use in the treating, reducing, ameliorating, or preventing an injury to an organ in a mammal, comprising a therapeutically-effective amount of NGAL, or a derivative or analog thereof. The composition can further a siderophore, typically in a 1:1 molar ratio, including a complex of the NGAL with the siderophore. The composition can be used in any of the methods disclosed herein.

The present invention also relates to the use of siderophores in association with NGAL in a composition and a method for treating, reducing, ameliorating, or preventing an ischemic or toxin-induced condition and disease, including an ischemic, an ischemia-reperfusion, or a toxin-induced injury in an organ.

In one embodiment of the invention, NGAL and a siderophore are administered as a pharmaceutical composition in an amount effective to enhance the treatment, reduction, amelioration or prevention of an ischemic, an ischemia-reperfusion, or a toxin-induced injury in an organ.

The present invention also relates to a pharmaceutical composition that comprises a siderophore, for use in administration to patients to enhance treatment prevention, amelioration, and reduction of injury in an organ by endogenous NGAL. In another embodiment, a method is provided for co-administering, typically as a complexed compound, of NGAL and a siderophore. In another embodiment, a siderophore is administered to a patient in an amount effective to enhance the renal re-epithelialization or positively affect the proliferation of tubular cells initiated by endogenous NGAL secretion.

In particular, the invention provides a method of enhancing the reduction or amelioration of delayed graft function (DGF) and organ or graft transplant rejection in a patient by endogenous NGAL, comprising the step of introducing a siderophore into (i) a transplanted organ or graft; (ii) a donor of a transplanted organ; or (iii) both (i) and (ii), in an amount effective to enhance the reduction or amelioration of DGF, or the loss or acute rejection of the transplanted or grafted organ. The method includes administering a siderophore in an amount effective to treat, reduce, ameliorate or prevent the injury to the organ.

In an embodiment of the invention, NGAL:siderophore complexes can be added to an organ preservation solution, such as is used during cold storage of transplant organs, to ameliorate the DGF that is characteristic of cadaveric kidney transplantation. In yet another embodiment, siderophores alone in a buffer solution can be added to an organ preservation solution, such as is used during cold storage of transplant organs, to ameliorate the DGF that is characteristic of cadaveric kidney transplantation.

The invention further provides a method for manipulating cellular and extracellular iron in an ischemic or toxin-damaged organ by administering NGAL, or a derivative or analog thereof. This method can also include administering an iron-binding chemical, a co-factor for an iron-binding chemical, or a siderophore in an amount effective to treat, reduce, ameliorate or further prevent organ damage by ischemia or toxins. Typically the ischemic or toxin-damaged organ is a kidney.

In another embodiment, the present invention provides a therapeutic kit comprising a first container for containing a therapeutically-effective amount of NGAL. The first container can include at least one vial, at least one test tube, at least one flask, and at least one bottle. The kit can also include a second container into which at least one composition can be placed, and a means for securing the containers together for commercial sale. The kit can also include a third container for containing a sterile, pharmaceutically acceptable buffer or other diluent. The first container can be a syringe. The means for securing the containers can be an injection or blow-molded plastic container into which the containers are retained. Alternatively, the vials can be prepared in such a way as to permit direct introduction of the composition into an intravenous drug delivery system. Instructions for use are also typically included.

Further aspects, features and advantages of the present invention will be better appreciated upon a reading of the detailed description of the invention when considered in connection with the accompanying drawings.

BRIEF DESCRIPTION OF THE SEQUENCE LISTING

Figure 1:
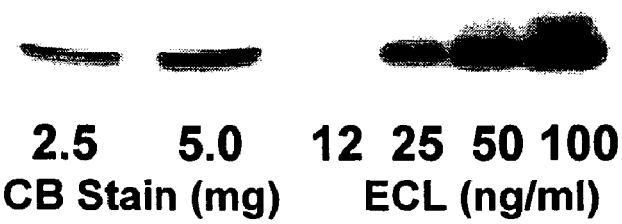
FIG. 1 shows Coomassie Blue (CB) and enhanced chemiluminescence (ECL, with polyclonal NGAL antibody) analysis of defined quantities (as shown) of recombinant purified NGAL.

The accompanying sequence listings, which are incorporated in and constitute a part of this specification, serve to explain the principles of the invention.

SEQ:ID 01 is an example of a Primer sequence (forward primer, positions 93-112) for mouse NGAL mRNA (Genbank NM_008491).

SEQ:ID 02 is an example of a Primer sequence (reverse, positions 576-557) for mouse NGAL mRNA (Genbank NM_008491).

SEQ:ID 03 is an example of Sequences (forward, positions 415-434) for mouse β-actin mRNA (Genbank X03672).

SEQ:ID 04 is an example of Sequences (reverse, positions 696-677) for mouse β-actin mRNA (Genbank X03672).

DETAILED DESCRIPTION OF THE INVENTION

Definitions

As used herein, the term "organ" means a differentiated biological structure comprised of cells and tissues that perform a certain function or functions in an organism, such as a mammal, including humans. Representative organs include, but are not limited to, the kidney, liver, heart, bone, cartilage, skin, lung, blood vessels, bladder, certix, stomach, intestine, pancreas, small intestine, colon, pancreas and brain, and portions or sections thereof.

As used herein, the term "renal injury" or "renal disease" shall include acute (including but not limited to ischemia, ischemia-reperfusion, nephrotoxic, shock, stroke, sepsis, trauma, infection, inflammation) or chronic (including but not limited to hypertension, diabetes, heart failure, lupus, infections, inflammations) kidney injuries or conditions.

The phrases "pharmaceutically acceptable," "pharmacologically acceptable," and "physiologically acceptable" refer to molecular entities and compositions that do not produce an adverse, allergic or other untoward reaction when administered to an animal, such as, for example, a human.

The phrase "pharmaceutically acceptable carrier" as used herein means a material, composition or vehicle, such as a liquid or solid filler, diluent, excipient, solvent or encapsulating material, involved in carrying or transporting the compounds of the invention from one organ, or portion of the body, to another organ, or portion of the body without affecting its biological effect. Each carrier should be "acceptable" in the sense of being compatible with other ingredients of the composition and not injurious to the subject. Some examples of materials which can serve as pharmaceutically-acceptable carriers include, but are not limited to: any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. Except insofar as any conventional carrier is incompatible with the NGAL, sideophore, or complex thereof, or other optional active agent or ingredient, its use in the therapeutic or pharmaceutical compositions is contemplated.

The phrase "therapeutically effective amounts" refers to those amounts of NGAL, siderophore, and mixtures thereof, or of other optional active agents or ingredients, that is effective to produce beneficial results, particularly with respect to the treatments described herein, in the recipient, such as an animal or patient. Such amounts can be initially determined by reviewing the published literature, by conducting in vitro tests or by conducting metabolic studies in healthy experimental animals. Before use in a clinical setting, it can be beneficial to conduct confirmatory studies in an animal model, typically a widely accepted animal model of the particular disease to be treated. Typical animal models for use in certain embodiments are rodent and murine models, which are economical to use and, particularly, because the results gained are widely accepted as predictive of clinical value.

The term "derivative(s)", in reference to NGAL, refers to chemically modified NGAL compounds, substances, inhibitors, or stimulators that still retain the desired effects on property(ies) of ischemia, renal tubule necrosis, nephrotoxicity, ischemic-reperfusion injury, and the like. Such derivatives can include the addition, removal, or substitution of one or more chemical moieties on the parent molecule. Such moieties can include, but are not limited to, an element such as hydrogen, a halide, or a molecular group such as a methyl group. Such a derivative can be prepared by any method known to those of skill in the art. The properties of such derivatives can be assayed for their desired properties by any means described or known to those of skill in the art.

The term "analog" includes a structural equivalent or mimetic, as understood by those of skill in the art.

A "patient", "recipient", or "subject" means an animal or organism, such as a warm-blooded animal or organism. Illustrative animals include, without limitation, mammals, for example, humans, non-human primates, pigs, cats, dogs, rodents, horses, cattle, sheep, goats and cows. The invention is particularly suitable for human patients and subjects.

An "inhibitor" means a compound, substance or agent that produces any measurable decrease in the activity, function, production, or secretion of a protein or biological compound, or in the translation of mRNA, in or from a cell.

As used herein in connection with transplanted and grafted organs, a "reduction" of ischemic injury or ischemic-reperfusion injury refers to any measurable decrease, diminution or reversal of damage to organs that (i) are stored, e.g., in preservation solution or in a cadaver, or (ii) are transplanted or grafted into a patient. Similarly, "reducing" refers to any measurable decrease or diminution, or a complete inhibition of damage, injury, or insult to organs that are stored, transplanted, or grafted into a patient.

The words "a" and "an" as used herein refers to "one or more". More specifically, the use of "comprising," "having," or other open language in claims that claim a combination or method employing an object, denotes that "one or more of the object" can be employed in the claimed method or combination.

The present invention provides neutrophil gelatinase-associated lipocalin, or NGAL, for use in methods of treating, reducing, or ameliorating ischemic injury, ischemic-reperfusion injury, and a toxin-induced injury, to an organ such as the kidney. The present invention also provides the use of NGAL in methods of treating, reducing, or ameliorating acute kidney injuries (including but not limited to shock, trauma, stroke, sepsis, infection, inflammation, stones, and surgeries) and chronic kidney injuries (including but not limited to hypertension, diabetes, heart failure, lupus, inflammation, glomerulonephritis and interstitial nephritis). In accordance with the invention, yet without wishing to be bound by theory, NGAL administration has been found to affect tubule cell death so as to limit apoptotic tubule cell death, i.e., apoptosis, and to enhance re-epithelialization, i.e., the recovery of viable cells following ischemia in the kidney involving de-differentiation and proliferation of viable cells and re-establishment of the epithelial phenotype following ischemia-reperfusion injury. NGAL administration has also been shown to reduce increases in serum and plasma creatinine levels after ischemic injury.

Human NGAL, a 25 kDa protein that is covalently bound to gelatinase from human neutrophils, is expressed at very low levels in several human tissues, including kidney, trachea, lungs, stomach, and colon. NGAL expression is markedly induced in and secreted by stimulated epithelia. For example, NGAL concentrations are elevated in the serum of patients with acute bacterial infections, the sputum of subjects with asthma or chronic obstructive pulmonary disease, and the bronchial fluid from the emphysematous lung. NGAL is also one of the maximally-induced genes in the kidney following early ischemic injury. These data are derived from analyses of mRNA by gene chip, implicating that the damaged kidney synthesizes NGAL. Other studies have shown that NGAL can be found at elevated levels in the serum of human patients with inflammatory diseases. Hence we have evaluated the incidence of expression of NGAL in human ATN compared to chronic forms of renal disease. NGAL is highly expressed in clinically defined ATN and appears in the proximal tubule in biopsied human kidney. Although less abundant, NGAL is also expressed in the kidney in several forms of chronic kidney disease. A mouse model of ischemia/reperfusion induced ATN also expresses NGAL at very high levels. Microgram quantities of injected NGAL provided dramatic protection against ATN as measured by plasma creatinine and by the histology of the kidney. The protection of the kidney was due to the delivery to the proximal tubule of NGAL protein containing the bacterial siderophore.

The preparation of a pharmaceutical composition or formulation comprising NGAL is known to those of skill in the art in light of the present invention, as exemplified by Remington's Pharmaceutical Sciences, 18th Ed., Mack Printing Company, 1990. Moreover, for animal (e.g., human) administration, it will be understood that preparations should meet sterility, pyrogenicity, general safety and purity standards as required by the FDA Office of Biological Standards.

Previously, the role of NGAL was unclear; however, NGAL has now been identified as an iron-transporting protein during nephrogenesis. Despite its high affinity for siderophores and for iron, NGAL can deliver iron to the cytoplasm. The likely mechanism for iron delivery from NGAL is by endocytosis. Fluorescent NGAL protein is endocytosed, and this trafficking is blocked by 4° C. temperatures. Acidification of these vesicles can be necessary for iron release from NGAL because agents that inhibit acidification blocked iron uptake. Moreover, addition of NGAL to cells expressing a fluorescent iron reporter in the cell cytoplasm stimulated iron-activated changes in reporter expression, confirming that NGAL can serve as an iron donor. Notably, the pathway for NGAL endocytosis differed from the pathway taken by holo-transferrin in cells in culture. At steady state, holotransferrin trafficked to rab-5 or rab-7 recycling vesicles (rab5 and rab7 are markers for early and late endosomes, respectively), while NGAL trafficked to late endosomes and in a small percentage to lysosomes. These data demonstrate that NGAL can serve in an iron delivery pathway when it contains a siderophore.

The actions of NGAL in vivo might differ from its pharmacological effects because the critical siderophore in vitro is a bacterial product. A number of analyses have indicated the possibility of endogenous low molecular weight co-factors for iron transport. These include citrate and related compounds, but also iron transport activities in the molecular weight range of 1000 Da. To determine whether such a cofactor might also be present in the kidney, we mixed apo-NGAL from BL21 bacteria with urine samples. While the urine itself failed to trap $^{55}$Fe, and apo-NGAL diluted in salt solutions failed to trap $^{55}$Fe, dilution of NGAL in urine permitted retention of $^{55}$Fe. This finding suggests that a cofactor is present in urine that permits NGAL-iron interactions.

In embodiments of the present invention, the exogenous administration of NGAL can ameliorate the structural damage inflicted by ischemia-reperfusion injury. Both apoptosis and necrosis can be significantly blunted. Without wishing to be bound by theory, the mechanism by which NGAL inhibits apoptosis in the ischemic condition includes an anti-apoptotic effect analogous to that of heme oxygenase 1 (HO-1), which facilitates the extracellular transport of iron, thereby limiting iron-driven oxidant stress in the intracellular compartment (C. D. Ferris et al., 1999, Nat. Cell Biol., 3:152-157). As a carrier of any of various siderophores, NGAL also facilitates the removal of excess intracellular iron, thereby limiting oxidant-mediated apoptosis of renal tubule cell death following ischemia-reperfusion injury. With respect to necrosis, the response of the kidney following ischemia-reperfusion injury can occur by a two-stage process, namely initiation of apoptosis followed by a necrotic cell death. In addition to limiting iron-mediated oxidative-stress, apoptosis inhibition by NGAL can be effective in preventing the secondary necrosis aspect of the process. By the process of apoptosis inhibition, NGAL can be effective in a variety of kidney diseases that are well known to be associated with increased apoptosis, including but not limited to ischemia, ischemia-reperfusion, nephrotoxins, polycystic kidney disease, obstruction, inflammation, and glomerular diseases.

NGAL protein is composed of eight β strands which form a β-barrel or a calyx. The calyx binds and transports low molecular weight chemicals, including siderophores found in urine and/or produced by bacteria. The best evidence for NGAL's ligand-binding properties comes from crystallographic studies, which demonstrated a bacterial siderophore (enterochelin) in the β-barrel. NGAL binds the siderophore with high affinity (0.4 nM) and the siderophore traps iron with high affinity ($10^{-49}$M). The stoichiometry of protein:siderophore:iron is 1:1:1, as demonstrated by binding studies and x-ray crystallography. When the siderophore was loaded with iron, the NGAL complex donated iron to embryonic mesenchyme in vitro and to cell lines, and when the siderophore was iron-free, the NGAL complex chelated iron. NGAL was endocytosed by many cell types, and trafficked to a late endosomal compartment that differed from the transferrin compartment. Donation of iron took place in an endosomal compartment. Because NGAL is the first mammalian protein found to bind bacterial siderophores, it can also been called siderocalin.

Siderophores are small protein molecules that scavenge iron from the environment, having a low molecular weight ranging from about 500 to about 1000 MW. Siderophores can chelate ferric iron. Iron-catalyzed damage is thought to be one of the earliest events in kidney dysfunction following an ischemic, ischemic-reperfusion, or toxin-induced injury, and is likely to be important in the early stages of damage to other organs, including the heart and the liver. Chelating iron with siderophores can blunt the damage to these organs.

Siderophores can be synthetic or naturally-occurring products harvested from bacterial cultures, and are commercially available. Siderophores are avidly taken up by NGAL when mixed together under physiological conditions in a wide variety of commonly used buffers including 10 mM Tris or Phosphate-buffered Saline. Typically, siderophores can be added in excess to a known quantity of NGAL protein. NGAL molecules will bind to siderophore molecules such that each complex will contain one molecule of each species. The 1:1 complexes of NGAL:siderophore are washed to remove the excess unbound siderophore molecules, and can then be further processed for use in the practice of the invention. Alternatively, equimolar amounts of siderophore and NGAL molecules can be combined and incubated to allow binding. Exogenous siderophores contemplated for use in the invention include, but are not limited to enterochelin, carboxymycobactin, aminochelin, desferrioxamine, aerobactin, arthrobactin, schizokinen, foroxymithine, pseudobactins, neoenactin, photobactin, ferrichrome, hemin, achromobactin, achromobactin, rhizobactin, and other bacterial products, as well as citrate and synthetic analogs and moieties and others that can be produced using organic chemistry processes. Endogenous siderophores can also be complexed to NGAL in vivo, as will be described in examples of the methods for use.

The methods of the present invention provide certain advantages for the patient. Acute renal failure secondary to ischemic injury remains a common problem, with limited and unsatisfactory therapeutic options. The identification of factors that inhibit, reduce, or oppose tubule cell death (necrosis/apoptosis) and/or enhance the recovery phase (involving de-differentiation and proliferation of viable renal tubule cells and re-establishment of the epithelial phenotype) can serve as novel therapeutic options. In accordance with this invention, NGAL, both alone and together with siderophores, advantageously exhibits the above-mentioned desirable and cytoprotective properties. Exogenously administered NGAL has been demonstrated to limit the morphologic and functional consequences of ischemia-reperfusion injury in a mouse model, by a combination of limiting apoptotic tubule cell death and enhancing re-epithelialization.

In an embodiment of the invention for treating, reducing, or ameliorating a toxin-induced injury, the toxin and/or the therapeutic that is toxic, can include an antibiotic, an anti-inflammatory agent, an antifungal agents, a radio-contrast agent, a pharmaceutical, a chemotherapeutic agent, a test drug, a medicament substance, or naturally-occurring, commercial and industrial chemicals and minerals. Specific toxins and nephrotoxins include, but not limited to, a cancer chemotherapeutic such as cisplatin, mitomycin, cyclophosphamide, isosfamide, and methotrexate, an antibiotic including gentamicin, vancomycin, and tobramycin, an antifungal agent, such as amphotericin, an anti-inflammatory agent, such as an NSAID, an immunosuppressant, such as cyclosporine and tacrolimus, other medicaments, commercial and industrial chemicals, such as hydrocarbons, chlorocarbons and fluorocarbons, and minerals such as arsenic, mercury, bismuth and lead. Other nephrotoxic compounds can include an aminoglycoside, foscarnet, pentamidine, vancomycin, neomycin, nitrous oxide, isoflurane, kanamycin, and cyclophosphamide.

In accordance with embodiments of the invention, NGAL can be administered prior to, during (at the same time as), or following ischemia, ischemic-reperfusion injury, organ transplant, ATN, toxin administration, and the like, as described herein. More particularly, NGAL can be administered to the patient from about 30 minutes to about 90 minutes before an organ is transplanted. It is also contemplated that the compositions can be administered at times outside the range of 30 to 90 minutes.

The invention also includes a method of administering from about 1 to about 200 mg/kg body weight of NGAL to a patient, more typically from about 1 to about 100 mg/kg body weight. The amount of NGAL administered to a patient can vary or fall out side of the ranges given above. As discussed herein, the amount of NGAL administered to the patient can vary.

A composition of the present invention, such as a medicament or pharmaceutical composition, can typically comprise a level of NGAL and/or sideophore of at least about 10 microgram/100 microliter of composition, and more typically at least about 100 microgram/100 microliter of composition.

A composition of the present invention can include different types of pharmaceutically acceptable carriers, depending on whether they are to be administered in solid, liquid or aerosol form, and whether they need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the foregoing as would be known to one of ordinary skill in the art.

The actual dosage amount of a composition of the present invention administered to an animal patient can be determined by physical and physiological factors such as body weight, severity of the condition being treated, the type of disease being treated, previous or concurrent therapeutic interventions, idiopathy of the patient, and the route of administration. The practitioner responsible for administration will, in any event, determine the concentration of the NGAL, sideophore and mixtures thereof, and of other optional active agents, in a composition and appropriate dose(s) for the individual subject.

In certain embodiments, pharmaceutical compositions can comprise, for example, at least about 0.1% of another optional active agent or ingredient. In other embodiments, the active agent or ingredient can comprise between about 2% to about 75% of the weight of the unit, more typically between about 25% to about 60%, and any range derivable therein. In other non-limiting examples, a dose amount of the active agent or ingredient can comprise from about 1 microgram/kg body weight about 500 milligram/kg body weight, more typically from about 5 mg/kg body weight to about 100 mg/kg body weight.

In some instances, the composition can comprise various antioxidants to retard oxidation of one or more ingredient. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The compositions can be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as, for example, sodium, potassium, ammonium, calcium or ferric hydroxides, or such organic bases as isopropylamine, trimethylamine, histidine or procaine.

In embodiments where the composition is in a liquid form, a carrier can be a solvent or dispersion medium including, but not limited to, water, ethanol, polyol (e.g., glycerol, propylene glycol, liquid polyethylene glycol, etc), lipids (e.g., triglycerides, vegetable oils, liposomes), and combinations thereof. The proper fluidity can be maintained, for example, by the use of a coating such as lecithin, by the maintenance of the required particle size by dispersion in carriers such as, for example liquid polyol or lipids, by the use of surfactants such as, for example, hydroxypropylcellulose, or combinations thereof such methods. In many cases it is typical to include isotonic agents, such as, for example, sugars, sodium chloride or combinations thereof.

In other embodiments of the present invention, one can use eye drops, nasal solutions or sprays, aerosols or inhalants. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in typical embodiments, the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, can be included in the formulation. For example, various commercial nasal preparations are known and include drugs such as antibiotics or antihistamines.

In certain embodiments, the compositions are prepared for administration by such routes as oral ingestion. In these embodiments, the solid composition can comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions can be incorporated directly with the food of the diet. Typical carriers for oral administration comprise inert diluents, assimilable edible carriers, or combinations thereof. In other aspects of the invention, an oral composition can be prepared as a syrup or elixir, and can comprise, for example, at least one optional active agent or ingredient, a sweetening agent, a preservative, a flavoring agent, a dye, a preservative, or combinations thereof. In other embodiments, an oral composition can comprise one or more binders, excipients, disintegration agents, lubricants, flavoring agents, or combinations thereof.

In certain embodiments, a composition can comprise one or more of the following: a binder, such as, for example, gum tragacanth, acacia, cornstarch, gelatin or combinations thereof, an excipient, such as, for example, dicalcium phosphate, mannitol, lactose, starch, magnesium stearate, sodium saccharine, cellulose, magnesium carbonate or combinations thereof, a disintegrating agent, such as, for example, corn starch, potato starch, alginic acid or combinations thereof, a lubricant, such as, for example, magnesium stearate, a sweetening agent, such as, for example, sucrose, lactose, saccharin or combinations thereof, a flavoring agent, such as, for example peppermint, oil of wintergreen, cherry flavoring, orange flavoring, etc., or combinations of the foregoing. When the dosage unit form is a capsule, it can contain, in addition to materials of the above type, carriers such as a liquid carrier. Various other materials can be present as coatings or to otherwise modify the physical form of the dosage unit. For instance, tablets, pills, or capsules can be coated with shellac, sugar or both.

Additional formulations that are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general for suppositories, traditional carriers can include, for example, polyalkylene glycols, triglycerides or combinations thereof. In certain embodiments, suppositories can be formed from mixtures containing, for example, the active agent or ingredient in the range of about 0.5% to about 10%, and typically about 1% to about 2%.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active compounds into a sterile vehicle that contains the basic dispersion medium and/or the other ingredients. In the case of sterile powders for the preparation of sterile injectable solutions, suspensions or emulsion, the typical methods of preparation are vacuum-drying or freeze-drying techniques that yield a powder of the active compound plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active compounds to a small area.

The composition should be stable under the conditions of manufacture and storage, and preserved against the contaminating action of microorganisms, such as bacteria and fingi. It will be appreciated that exotoxin contamination should be kept minimally at a safe level, for example, less that 0.5 ng/mg protein.

Experimental Protocols

The invention will be better understood through examples illustrating its use and efficacy. The experimental protocols described below will be referenced in the examples that follow.

1. Expression, Purification, and Radiolabeling of Recombinant Human and Mouse NGAL:

Full length mouse NGAL cDNA was cloned into the pGEX expression vector, expressed as a fusion protein with glutathione S-transferase (GST) in bacteria, and purified using glutathione-sepharose columns (Amersham) followed by thrombin cleavage as previously by Bundgaard J et al., Biochem Biophys Res Commun 202: 1468-1475, 1994; Yang J et al., Mol Cell 10: 1045-1056, 2002; and Del Rio M et al., J Am Soc Nephrol 15: 41-51, 2004. Purified NGAL was made endotoxin-free with using the Detoxi-Gel endotoxin removing column (Pierce) as recommended by the manufacturer. Proteins were analyzed by SDS-PAGE followed by Coomassie blue staining or by Western blotting with a polyclonal antibody to NGAL as described by Mishra et al., J Am Soc Nephrol 14: 2534-2543, 2003. Protein concentrations were determined using the Bradford assay. A single clean polypeptide of the predicted size was detected, as shown in FIG. 1.

2. Expression and Purification of Recombinant Human and Mouse NGAL

Recombinant human and mouse GST-NGAL were expressed in BL21 or XL1-Blue strains of *E. coli* (Stratagene) with additional ferric sulfate (50 Micro Molar, Sigma-Aldrich Co.). NGAL was isolated using Glutathione Sepharose 4B beads (Amersham Biosciences), eluted by thrombin cleavage (Sigma-Aldrich Co.; St. Louis, Mo.) and then further purified by gel filtration (Superdex75, SMART system, Amersham Biosciences) and examined by Coomassie gels (Biorad). BL-21 derived NGAL was loaded with iron free or iron saturated enterochelin, a siderophore (EMC Microcollections) using a 5 fold molar excess. Unbound siderophore (0.7 KD) was removed by washing (Microcon YM-10) with PBS. To produce $^{55}$Fe or gallium (Ga) loaded NGAL we incubated the iron-free enterochelin NGAL complex with equimolar $^{55}$Fe (18 mCi) or Ga in NaCl (150 mM) Hepes (20 mM; pH 7.4) and the complex was washed 3 times (10K filter). Iodobeads (Pierce) were used to label NGAL with $^{125}$I and unincorporated $^{125}$I was removed by gel filtration (PD-10 column) followed by extensive dialysis (7 kDa cut off membrane, Pierce) against PBS. Alexa-568 and fluorescein isothiocyanate (Molecular Probes) was coupled to NGAL, according to the manufacturer, and then extensively dialyzed. Protein concentration was determined by Coomassie gels in comparison with bovine serum albumin standard.

3. NGAL Injections:

Purified endotoxin-free NGAL was administered either intravenously into mice via tail vein injections, subcutaneously, or intraperitoneally. In preliminary studies, animals were treated with three different concentrations of NGAL (50, 100, or 250 µg of a 250 µg/100 µl solution), subjected to 30 minutes of bilateral renal artery clamping one hour later, and examined after 24 hours of reflow. When compared to animals pre-treated with an equal volume (100 µl) of saline, only the group given 250 µg of NGAL exhibited a significant protection from the tubular damage and azotemia. All subsequent studies as reported here were carried out using the 250 µg dose of NGAL. Comparisons were made between five different animal groups: non-ischemic controls (n=8), ischemic controls pre-treated with saline alone (n=8), NGAL pre-treated one hour prior to renal artery clamping (n=6), NGAL treated during renal artery clamping (n=6), and NGAL treated one hour post renal artery clamping (n=6).

4. Human Studies:

Healthy volunteers and patients diagnosed with either acute or chronic renal failure were analyzed for NGAL protein levels in urine and serum. Acute renal failure (ARF) was diagnosed by a doubling of the serum creatinine in less than 5 days. The presumed etiology of ARF included sepsis which was defined by the presence of at least two of the following criteria: positive blood cultures or evidence of local infection in the lung, skin or urinary tract and fever or an elevated WBC count. Some of these patients required blood pressure support. Other etiologies of ARF included hypotension due to bleeding or heart failure, nephrotoxins, or post-transplant ischemia. The definition of chronic renal failure (CRF) was a serum creatinine greater than 2 mg/dl, but unchanged during at least the prior 2 months. The presumed etiologies of CRF included obstructive uropathy, chronic interstitial nephritis, and diabetes. Samples of blood and urine were collected from patients evaluated at Columbia University Medical Center and at Kyoto University Hospital with approval of both Institutional Review Boards and then analyzed in a blinded fashion.

5. Measurement of NGAL:

An anti-mouse NGAL polyclonal antibody was raised in rabbit and then purified on a column of Sepharose 4 fast flow beads (Amersham Biosciences) coupled to recombinant mouse NGAL (see below) followed by elution at pH 2.5. Monoclonal anti-human NGAL (AntibodyShop) was also used to detect NGAL. Human NGAL was better recognized by the monoclonal antibody while mouse NGAL was recognized only by the affinity-purified polyclonal.

Human blood samples were initially collected in citrate, EDTA or heparin, but since all of these preparations showed similar NGAL immunoreactivity, human serum and mouse plasma are collected in the examples described below. The samples were centrifuged through a 100 KDa cut-off filter (YM-100, Amicon) and the flow-through used for immunoblot. In patients undergoing hemodialysis, samples were taken immediately before dialysis. Fresh urine samples were centrifuged at low speed and then used without further concentration.

6. Pathologic Specimens:

Pathological specimens included ischemic ATN (10 cases), toxic ATN (11 cases—(5) antibiotics, (2) zoledronate, (1) carboplatinum, (2) non-steroidal anti-inflammatory agents, and (1) hemoglobinuria), and glomerulopathies (10 cases— including diabetic, anti-GBM, pauci-immune cresentic glomerulonephritis, IgA nephropathy, minimal change, focal segmental glomerulosclerosis), and also normal kidneys (3 cases). Formalin-fixed, paraffin-embedded tissues were sectioned (5 µm) and subjected to antigen retrieval using microwave in a citrate buffer (pH6.0) for 30 min. Endogenous peroxidase was blocked with 5% $H_2O_2$ for 30 min, followed by blocking in 10% goat serum/1% BSA. Affinity purified anti-mouse NGAL (0.4 µg/ml) was applied overnight at 4 C, followed by biotinylated goat anti-rabbit IgG (1:100, Vector) and avidin-HRP, each for 30 minutes. Slides were developed with DAB/0.3% $H_2O_2$ for 2.5 minutes and counterstained with hematoxylin. Non-immune rabbit IgG (0.4 µg/ml; Vector) was used as a control.

7. NGAL Trafficking:

To detect delivery of NGAL to the kidney rNGAL (10 or 100 µg), Alexa 568-NGAL (100 µg), $^{125}$I-NGAL (10 µg, $2\times10^6$ cpm), or $^{55}$Fe loaded enterochelin-NGAL (10 µg, $1\times10^6$ cpm) was injected into the peritoneum and blood, urine, kidney and liver samples were obtained. NGAL was detected by immunoblot. Alexa-568 NGAL was detected by confocal microscopy (LSM Meta Detector) and NGAL mediated iron trafficking was detected by scintillation counter and by light microscopic radioautography of Epon embedded kidneys. Slides were exposed to emulsion (Polyscience) for 1 week and then developed with Microdol and counterstained with Toluidine blue. To detect lysosomes in the proximal tubule, mice were injected with Fluorescein Dextran (46 kD; 0.5 mg; Sigma) 24 hours before Alexa 568 NGAL injections. LAMP1 (Santa Cruz) was detected in cryostat sections of 4% paraformaldehyde fixed kidneys.

8. Mouse Model of ATN or Ischemia/Reperfusion Injury:

Male C57BL/6 mice (20-25 gr; Charles River) were anesthetized with intraperitoneal pentobarbital (50 mg/kg) and placed on a heating pad under a warming light to maintain 37© core body temperature. Kidneys were exposed through an abdominal section and the right kidney was either removed or its vascular pedicle and ureter ligated. The vascular pedicle of the left kidney or both kidneys was clamped by a microaneurysm clip (Kent Scientific) for 30 minutes after right nephrectomy. This period of ischemia generated reproducible renal injury but minimized mortality. During the procedure, PBS (0.5 ml) was used to dampen the peritoneum. The animal was closed with 5-0 Nylon. Saline, NGAL, retinol-loaded retinol binding protein (RBP), enterochelin, or desferroxamine mesylate (DFO) were injected into the peritoneum or subcutaneously 15 min. prior to ischemia or 1-2 hr after reperfusion.

After 6 or 24 hr of reperfusion, heparinized plasma, urine and kidney samples were obtained to measure NGAL (polyclonal 1:500), Heme oxygenase-1 (Stressgen, 1:2000), E-cadherin (BD Transduction Labs, 1:2000), N-cadherin (BD Transduction Labs, 1:3000) and GAPDH (Chemicon International, 1:3000) using immunoblots. Plasma was also used for creatinine and blood urea nitrogen colorimetric assays. Sagittal sections of the kidney were fixed in 4% formalin, or were snap frozen for mRNA and protein analysis. Paraffin-embedded sections (5 µm) were stained with hematoxylin-eosin or by an in situ kit (Fluorescein-TUNEL, Roche) for apoptotic nuclei or for total nuclei (Toprol, Molecular Probes). For cell proliferation analysis, BrdU was injected into the peritoneum 1 hour before sacrifice, and cryostat sections were stained with anti-BrdU (Roche) according to the manufacturer.

For some studies, the mice were allowed to recover in a warmed cage, and timed urine collections were obtained. After various reperfusion periods, the animals were then reanesthetized, the abdominal cavity opened, and blood obtained via puncture of the inferior vena cava for measurement of serum creatinine by quantitative colorimetric assay. The mice were killed, the kidneys perfusion fixed in situ with 4% paraformaldehyde in PBS, and both kidneys harvested. One half of each kidney was snap frozen in liquid nitrogen and stored at −70° C. until further processing; a sample was fixed in formalin, paraffin-embedded, and sectioned (4 µm). Paraffin sections were stained with hematoxylin-eosin and examined histologically. The other half of each kidney was embedded in OCT compound (Tissue-Tek) and frozen sections (4 µm) obtained for immunohistochemistry.

9. Real-Time PCR:

Total RNA was extracted from mouse kidneys using RNeasy mini kit (Qiagen) with on-column DNase digestion according to the manufacturer's instructions. The cDNA template was synthesized using Omniscript Reverse Transcriptase and oligo-dT primer (Qiagen). The PCR reaction was carried out using iQ SYBR green super mix and MyiQ single-color real-time PCR detection system (Biorad) with incubation times of 2 min at 95° C., followed by 40 cycles of 95° C./30 s and 60° C./30 s. Specificity of the amplification was checked by melting curve analysis and by agarose gel electrophoresis. Primer sequences for mouse NGAL mRNA (Genbank NM_008491) were CTCAGAACTTGATCCCT-GCC (forward primer, positions 93-112) and TCCTTGAG-GCCCAGAGACTT (reverse, 576-557). Sequences for mouse β-actin mRNA (Genbank X03672) were CTAAGGC-CAACCGTGAAAAG (forward, 415-434) and TCTCAGCT-GTGGTGGTGAAG (reverse, 696-677). Each plate included a dilution series of standard sample, which was used to determine mRNA quantities. The NGAL mRNA content was normalized by β-actin mRNA.

10. Iron Binding Co-Factor

Cofactor-dependent iron binding to NGAL was measured in 150 mM NaCl-20 mM Hepes (pH7.4) buffer (100 μl) with apo-NGAL (10 μM), $^{55}$Fe (1 μM), and a low molecular weight fraction (<3 Kd) of mouse urine (0-30 μl) and incubated 70 min. at room temperature. The urine fraction was obtained by passing fresh urine sequentially through 10 kDa and 3 kDa membranes (YM-10 and YM-3, Amicon). The mixture was then washed three times on 10 kDa membrane (YM-10, Amicon). Iron-free enterochelin-loaded NGAL (rather than NGAL without siderophore) served as a positive control for iron capture. Ferric citrate (1 mM) or iron-loaded enterochelin (Sid:Fe, 50 μM) were used as competitors of $^{55}$Fe binding.

11. NGAL Immunohistochemistry:

For NGAL detection, frozen kidney sections were permeabilized with 0.2% Triton X-100 in PBS for 10 min, blocked with goat serum for 1 hr, and incubated with primary antibody to NGAL (1:500 dilution) for 1 hr. Slides were then exposed for 30 min in the dark to secondary antibodies conjugated with Cy5 (Amersham, Arlington Heights, Ill.), and visualized with a fluorescent microscope (Zeiss Axiophot) equipped with rhodamine filters.

12. Histopathology Scoring:

Kidney sections of 4 microns were stained with hematoxylin-eosin and scored for histopathologic damage to the tubules in a blinded fashion, as previously described by Yokota N. et al., Am J Physiol Renal Physiol 285: F319-F325, 2003 and Kjeldsen L. et al., Biochim Biophys Acta 1482: 272-283, 2000. Each parameter was assessed in five high power fields (40×) in the inner cortex and outer medullary regions (where the tubular damage was most evident), and an average determined for each section. The parameters included tubule dilatation, tubule cast formation, and tubule cell necrosis. Each parameter was scored on a scale of 0 to 4, ranging from none (0), mild (1), moderate (2), severe (3), to very severe/extensive (4).

13 Apoptosis Assays:

For the TUNEL assay to detect apoptotic nuclei, we utilized the ApoAlert DNA Fragmentation Assay Kit (Clontech). Paraffin sections were deparaffinized through zylene and descending grades of ethanol, fixed with 4% formaldehyde/PBS for 30 min at 4° C., permeabilized with proteinase K at room temperature for 15 min and 0.2% triton X-100/PBS for 15 min at 4° C., and incubated with a mixture of nucleotides and TdT enzyme for 60 min at 37° C. The reaction was terminated with 2×SSC, the sections washed with PBS, and mounted with Crystal/mount (Biomeda, Foster City, Calif.). TUNEL-positive apoptotic nuclei were detected by visualization with a fluorescent microscope. Only cells that displayed the characteristic morphology of apoptosis, including nuclear fragmentation, nuclear condensation, and intensely fluorescent nuclei by TUNEL assay, were counted as apoptotic. Merely TUNEL positive cells, in the absence of morphologic criteria, were not considered apoptotic. Slides were examined in a blinded fashion, and apoptosis was quantified by counting the number of TUNEL positive nuclei per 100 cells counted in an average of five high power (40×) fields in each section.

14. Proliferation Assays:

For detection of proliferating cells, sections were incubated with a monoclonal antibody to Proliferating Cell Nuclear Antigen (PCNA, 1:500 dilution, Upstate Biotechnology), and detection accomplished by immunoperoxidase staining as recommended by the manufacturer (ImmunoCruz Staining System, Santa Cruz Biotechnology). Slides were examined in a blinded fashion, and proliferation was quantified by counting the number of PCNA positive cells per 100 cells counted in an average of five high power (40×) fields in each section.

15. Statistical Analysis:

The SPSS software (version 8/0) was employed to generate univariate statistics for each continuous variable, including means, standard deviations, distributions, range, and skewness. The data were examined for normality and equality of distribution. One way ANOVA was employed to compare means±SD of continuous variables among different treatment groups. The Kruskal-Wallis ANOVA on Ranks was used for non-normally distributed data. To identify the group or groups that differed from the others, a multiple comparison procedure was used (Tukey test or Dunn's Method depending on the normality of distribution). A p value <0.05 was considered statistically significant. NGAL levels in humans were log transformed for statistical analysis. The data were analyzed by one-way ANOVA with Bonferroni's post-test to compare mean values across groups. The Jablonski score of kidney damage was analyzed by the Kruskal-Wallis test with Dunn's post-test.

EXAMPLES

The following examples are provided to more fully describe the practice of the invention in its various embodiments. Experimental protocols provided above are used as indicated in the examples.

Example 1

Figure 2:
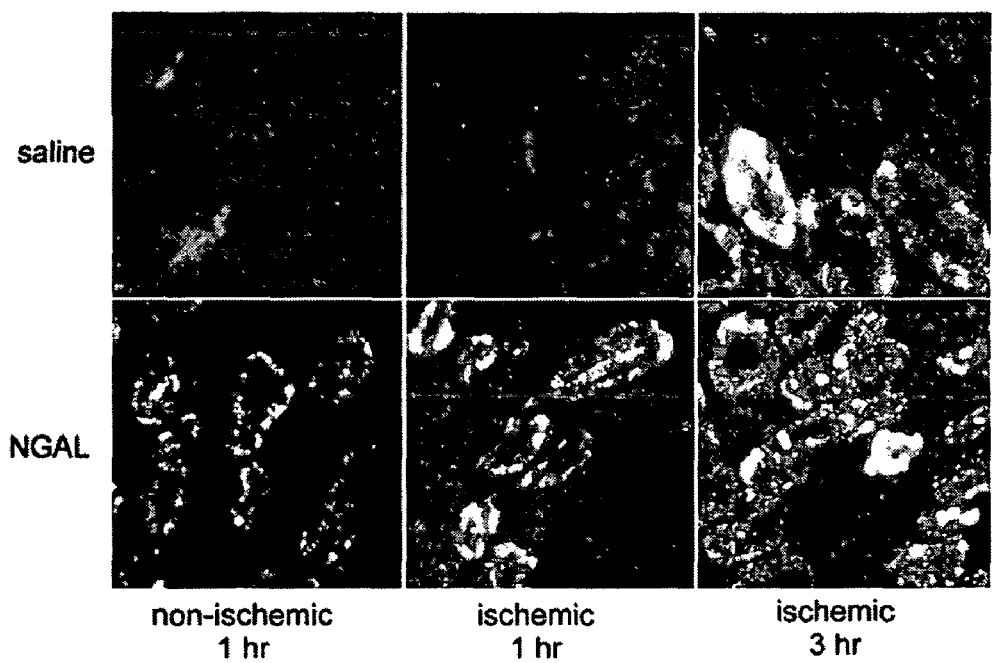
FIG. 2 shows immunofluorescent staining of kidneys from control non-ischemic animals one hour after injection, or ischemic kidneys one or three hours after either injection, using polyclonal NGAL antibody.
Figure 3:
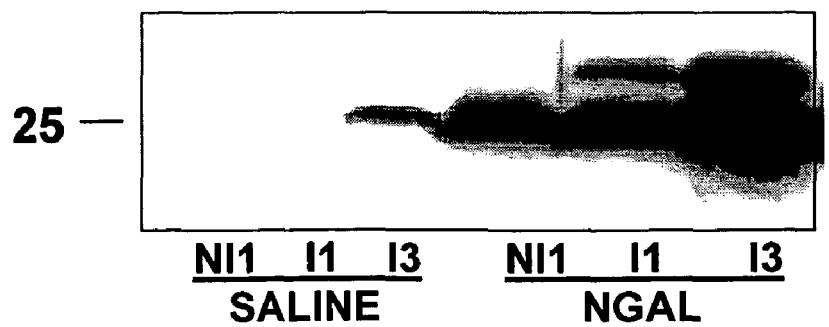
FIG. 3 shows Western blot for NGAL detection in urine samples from non-ischemic (NI) and ischemic (I) animals within 1 hour of administration of NGAL.

Intravenous NGAL is rapidly taken up by proximal tubule cells in vivo. Purified NGAL was delivered to its putative site of action, namely the proximal tubule. Mice received intravenous NGAL (250 μg in 100 μl saline) or an equal volume of saline alone, subjected to ischemia-reperfusion injury, and the kidneys and urine examined at various time periods, as shown in FIG. 2. Non-ischemic saline control animals had no NGAL (upper left panel), while non-ischemic NGAL-treated animals had NGAL (lower left panel). Saline-injected animals were devoid of kidney NGAL at one hour (upper center panel). Endogenous NGAL was detected in saline-treated animals at 3 hours after ischemic-reperfusion injury (upper right panel). In contrast, within one hour of NGAL injection, it was easily detected in a punctate cytoplasmic distribution predominantly in the proximal tubules (lower center panel), and was still seen at 3 hours (lower right panel). Identification of proximal tubules in these sections was based on location and morphology. This represents uptake of injected NGAL following ischemic injury, since NGAL was not detected at the one hour reflow period in saline-injected animals. In addition, NGAL was detected in the urine within one hour of injection, as shown in FIG. 3.

Example 2

Intravenous NGAL rapidly appears in the urine following administration and ischemic-reperfusion injury. Urine from the animals of Example 1 was examined at various time periods. Saline-injected animals were devoid of kidney or urinary NGAL at the 1 hour reflow period, and NGAL was just detectable at the 3-hour reflow period, as shown in FIG. 3 (left panel). The 3 hour data represents the endogenous response of kidney tubule cells to ischemic injury. In contrast, in animals injected with NGAL and simultaneously subjected to ischemia-reperfusion injury, NGAL was easily detected in the kidney and urine with 1 hour of reflow, as shown in FIG. 3 (right panel).

Example 3

Figure 4:
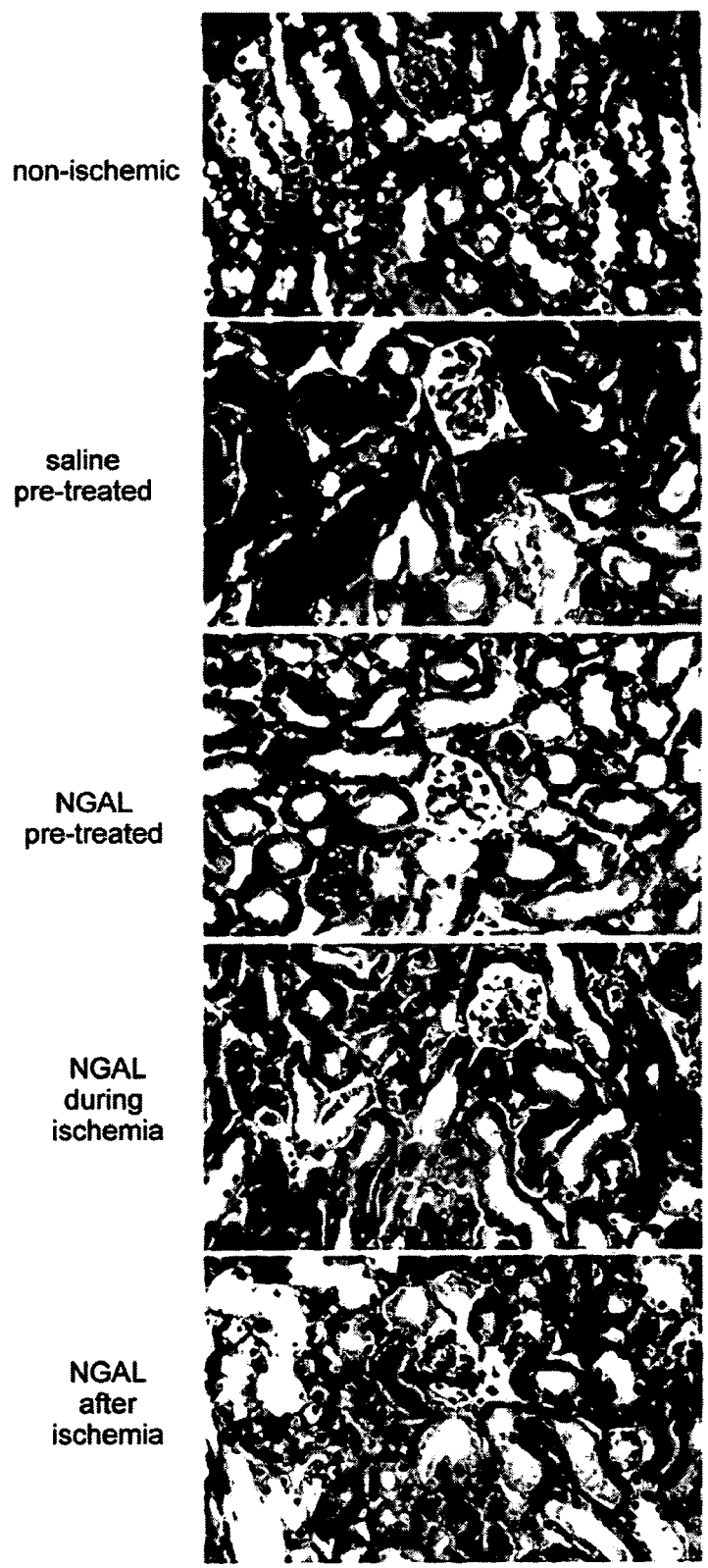
FIG. 4 shows sections stained with hematoxylineosin of kidneys from control non-ischemic mice, saline pre-treated ischemic mice, or ischemic mice treated with NGAL one hour before, during, or one hour after ischemia.
Figure 5A:
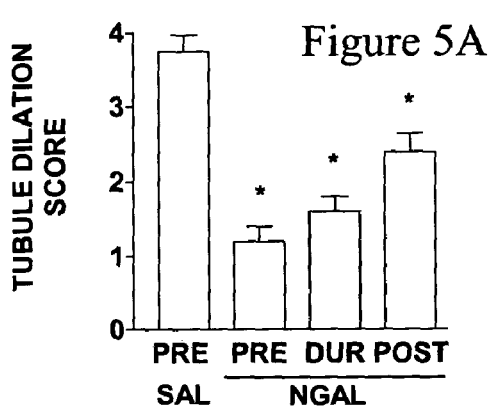
FIGS. 5A, 5B and 5C show scoring of histological sections of kidneys from ischemic mice that were saline pre-treated or treated with NGAL one hour before, during, or one hour after ischemia. The sections were analyzed and scored for tubule dilatation (FIG. 5A), tubule casts (FIG. 5B), and tubule cell necrosis (FIG. 5C) using an arbitrary scale of 0 to 4.
Figure 5B:
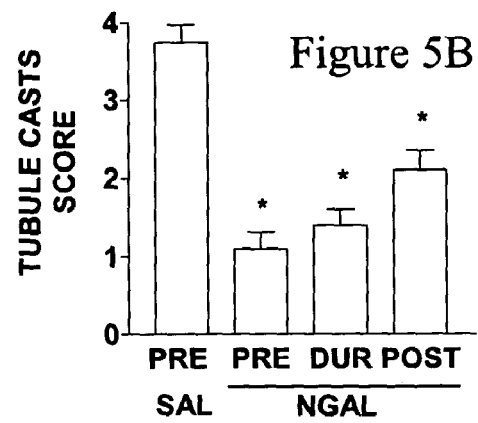
Figure 5C:
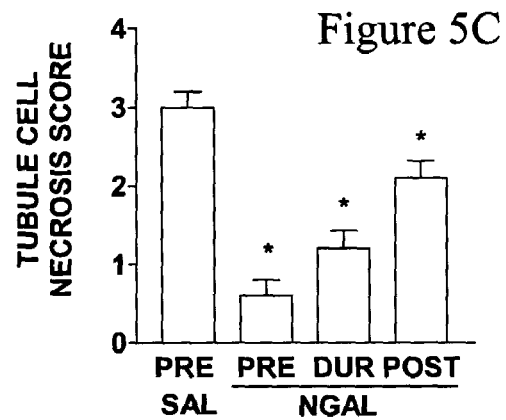

NGAL ameliorates the histopathologic damage to tubules induced by ischemia-reperfusion injury. NGAL administered one hour before, during, or even one hour after ischemia resulted in a significant decrease in the histopathologic damage to tubules. Representative kidney sections obtained at 24 hours of reflow and stained with hematoxylin-eosin are shown in FIG. 4. While the non-ischemic controls (Non-Ischemic panel) displayed normal histology, animals pre-treated with saline alone (Saline Pre-treated panel) (100 µl, volume of diluent) displayed extensive features of acute tubular necrosis, including tubular dilatation, tubular cast formation, and necrotic cells. In contrast, NGAL-treated kidneys displayed an attenuated histopathologic response. This was most evident in animals pre-treated with NGAL (NGAL Pre-treated panel), but was also evident when the NGAL was administered during (NGAL During Isch panel) or even one hour after (NGAL After Isch panel) the ischemic injury. In order to quantify this response, kidney sections were scored for histopathologic damage to the tubules in a blinded fashion. The results are illustrated in FIG. 5A-5C. In all three parameters examined, dilatation (FIG. 5A), casts (FIG. 5B), and cell necrosis (FIG. 5C), all three modalities of NGAL treatment (before, during, or after ischemia) resulted in a significantly improved score when compared to controls. This difference was most striking in animals pre-treated with NGAL, followed in a graded fashion by findings in animals treated with NGAL during ischemia or after the ischemic insult. However, the structural protection was not complete, and even animals pre-treated with NGAL did display some degree of histopathologic damage, which was completely absent from non-ischemic controls.

Example 4

Figure 6:
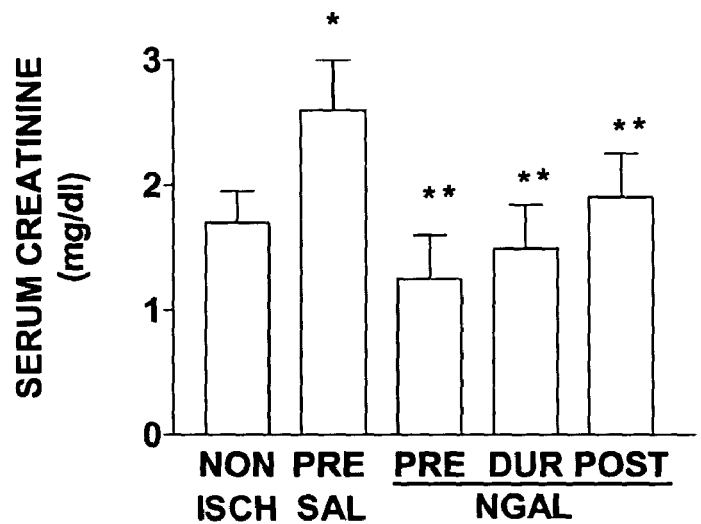
FIG. 6 shows serum creatinine measured in non-ischemic (Non Isch) control mice, or 24 hours following ischemia in mice pre-treated with saline (Pre Sal) or treated with NGAL one hour before (Pre NGAL), during (Dur NGAL) or one hour after (PostNGAL) ischemic injury.

NGAL ameliorates the reduction in kidney function induced by ischemia-reperfusion injury. NGAL administered one hour before, during, or even one hour after ischemia resulted in a significant decrease in the serum creatinine measured at 24 hours of reflow, as shown in FIG. 6. While the non-ischemic controls (Non Isch) displayed serum creatinine (0.65±0.13 mg/dl), animals pre-treated with saline alone (Pre Sal) (100 µl, volume of diluent) displayed a significant increase in serum creatinine (2.6±0.28 mg/dl). In contrast, NGAL-treated kidneys displayed an attenuated functional response. This was most evident in animals pre-treated with NGAL (1.25±0.3 mg/dl), but was also evident when the NGAL was administered during (Dur NGAL) (1.5±0.2 mg/dl) or even one hour after (Post NGAL) (1.95±0.2 mg/dl) the ischemic injury. However, the functional protection was not complete, and even animals pre-treated with NGAL did display a significant increase in serum creatinine when compared to non-ischemic controls.

Example 5

Figure 7:
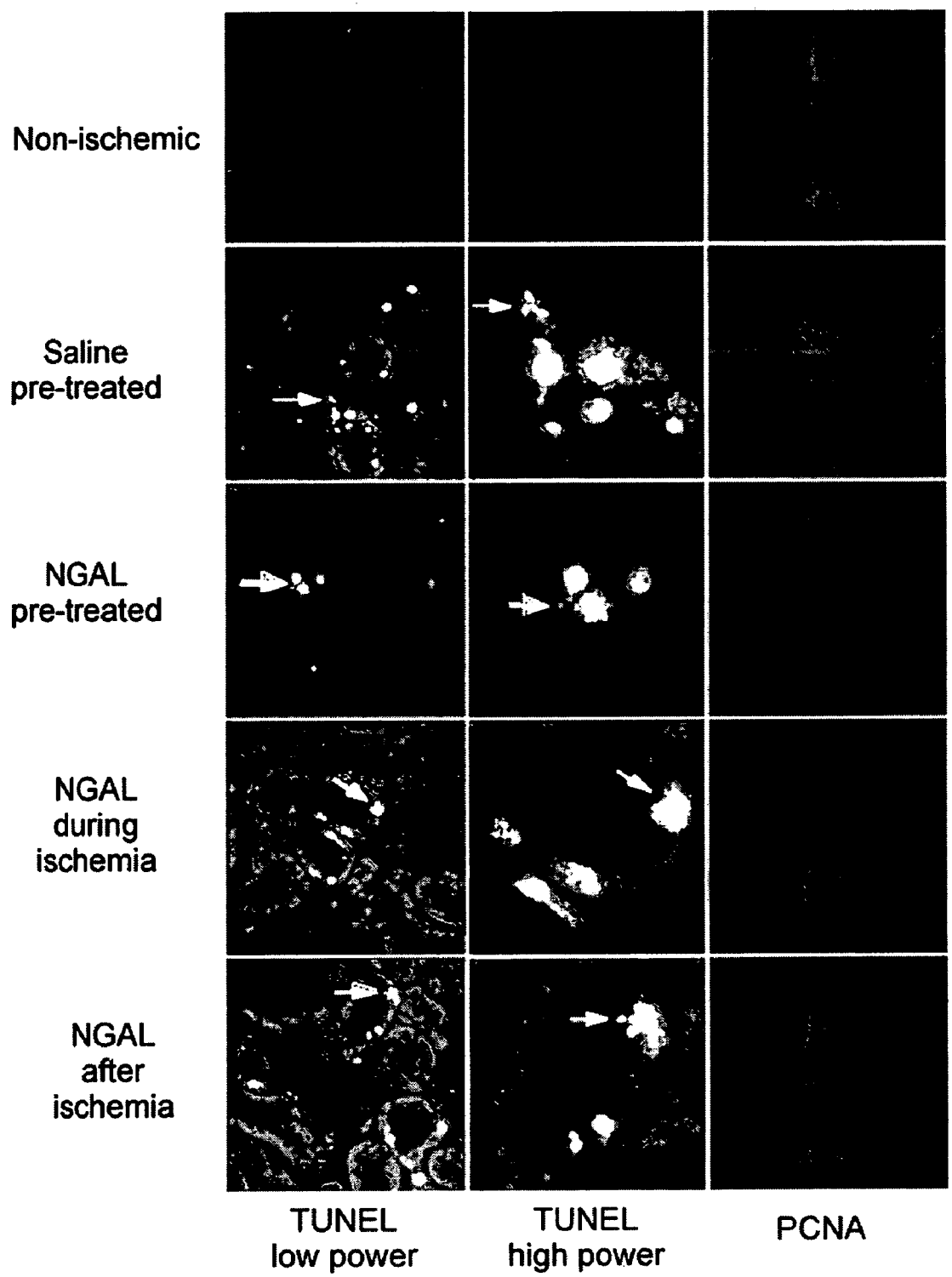
FIG. 7 shows results of TUNEL staining of representative sections from non-ischemic control mice, or 24 hours following ischemia in mice pre-treated with saline or treated with NGAL one hour before, during, or one hour after ischemic injury. Arrows point to the condensed, fragmented, intensely staining nuclei characteristic of apoptosis in low and high power magnifications, compared to staining with proliferating cell nuclear antigen (PCNA).
Figure 8:
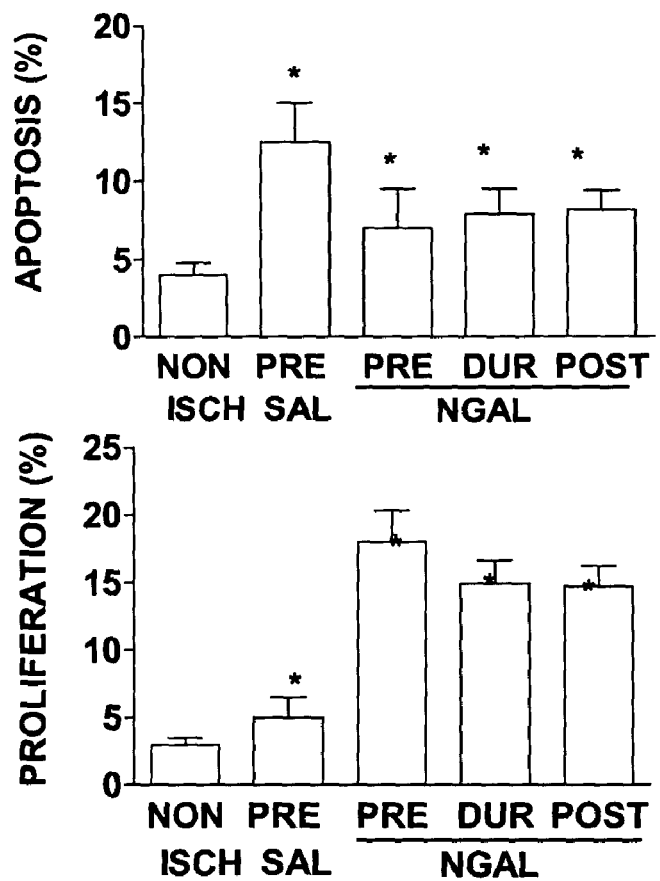
FIG. 8 shows quantitation of apoptosis (upper panel) and proliferation (center panel) in kidneys from non-ischemic control mice, or 24 hours following ischemia in mice pre-treated with saline or treated with NGAL one hour before, during, or one hour after ischemic injury.

NGAL ameliorates the apoptotic tubule cell death induced by ischemia-reperfusion injury. The structural and functional protection observed with exogenous NGAL administration was a result of decreased apoptosis. Representative kidney sections obtained at 24 hours of reflow and subjected to TUNEL assay are shown in FIG. 7 at low (left column) and high (center column) magnifications. While the non-ischemic controls displayed a minimal incidence of apoptosis (2.2±0.5 cells per hundred (%) cells examined), animals pre-treated with saline alone (100 µl, volume of diluent) displayed a significantly greater number of apoptotic tubule epithelial cells (12.6%±2.2), as shown quantitatively in FIG. 8 (left panel). In contrast, NGAL-treated kidneys displayed an attenuated apoptotic response. This was most evident in animals pre-treated with NGAL (6.7%±1.6), but was also evident when the NGAL was administered during (7.6%±0.8) or even one hour after (8.5%±0.8) the ischemic injury. However, the protection from apoptotic cell death was not complete, and even animals pre-treated with NGAL did display a significantly greater degree of apoptotic damage when compared to non-ischemic controls.

Example 6

NGAL enhances tubule cell proliferation following ischemic injury. Representative kidney sections obtained at 24 hours of reflow and stained with an antibody to PCNA are shown in FIG. 7 (right column). While the non-ischemic controls displayed a minimal incidence of proliferating cells (1.9%±0.4 cells per hundred cells examined), animals pre-treated with saline alone (100 µl, volume of diluent) displayed a small but significant increase in the number of PCNA-positive tubule epithelial cells (4.4%±1.2), as shown quantitatively in FIG. 8 (right panel). In contrast, NGAL-treated kidneys displayed a marked increase in proliferating cells. This was most evident in animals pre-treated with NGAL (19.1%±2.1), but was also evident when the NGAL was administered during (14.9%±1.2) or even one hour after (14.5%±1.2) the ischemic injury.

Example 7

Figure 9:
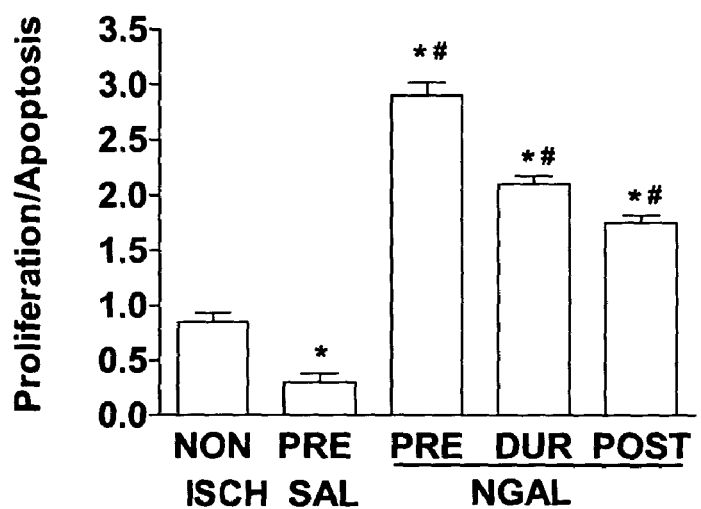
FIG. 9 shows a ratio of proliferation:apoptosis calculated in kidneys from non-ischemic control mice, or 24 hours following ischemia in mice pretreated with saline or treated with NGAL one hour before, during, or one hour after ischemic injury.
Figure 10:
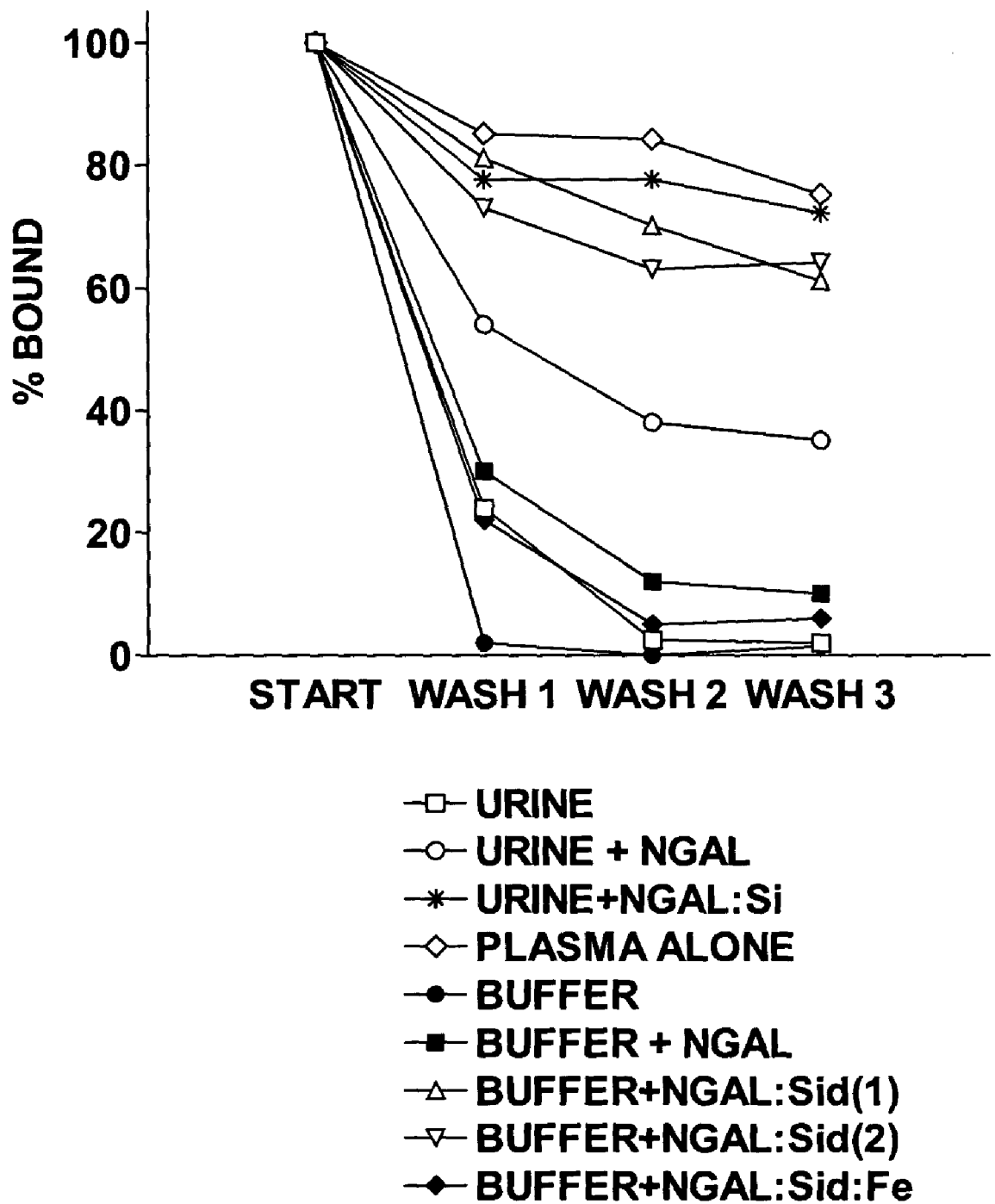
FIG. 10 shows binding of $^{55}$Fe detected in urine alone, a urine and NGAL mixture (urine+Ngal), a urine and NGAL: siderophore mixture (urine+Ngal:Si), plasma alone, buffer alone, buffer and NGAL mixture (buffer+Ngal), a buffer and NGAL:siderophore mixture (buffer+Ngal:Sid(1)), a second buffer and NGAL:siderophore mixture (buffer+Ngal:Sid(2)), and a third buffer and NGAL:siderophore mixture in which the siderophore was saturated with iron (buffer+Ngal:Sid:Fe).

NGAL tilts the balance of tubule cell fate towards survival following ischemic injury. The overall tubule cell fate following ischemic injury was estimated using a one-way ANOVA to compare means±SD of proliferation and apoptosis among the different treatment groups at 24 hours of reflow. A ratio of unity can be assumed to indicate equal rates of cell survival and death, as would be expected in the mature kidney at rest, illustrated in FIG. 9. Non-ischemic control kidneys displayed a proliferation:apoptosis ratio of 0.86±0.1, close to the value of unity. Animals pre-treated with saline alone (100 µl, volume of diluent) displayed a significant decrease in the proliferation:apoptosis ratio (0.34%±0.05), indicating that cell death is the predominant feature at the 24 hour reflow timepoint. In contrast, NGAL-treated kidneys displayed a marked increase in the ratio of proliferating versus apoptotic tubule cells. This was most evident in animals pre-treated with NGAL (2.9%±0.5), but was also evident when the NGAL was administered during (2.0%±0.1) or even one hour after (1.7%±0.1) the ischemic injury. This analysis indicates that NGAL tilts the overall balance of tubule cell fate towards cell survival following ischemic injury.

Example 8

Figure 11A:
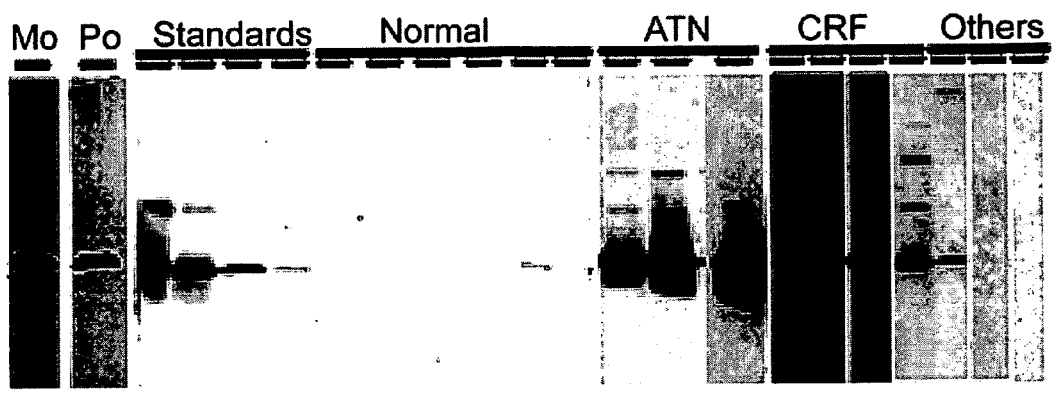
FIG. 11A shows immunoblots of NGAL protein in human urine samples from healthy subjects (Normal), or subjects with Acute Tubular Necrosis (ATN) or chronic renal failure (CRF), or from subjects with liver cirrhosis, hemochromatosis, or pancreatic carcinoma but lacking a renal diagnosis (Others). Monoclonal anti-human NGAL (Mo) and polyclonal anti-mouse NGAL (Po) antibodies recognizes recombinant and native human NGAL and NGAL Standards.
Figure 11B:
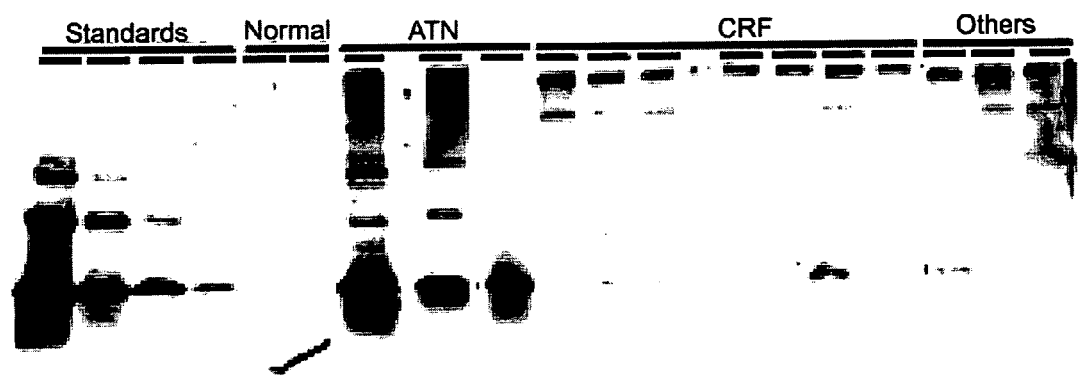
FIG. 11B shows immunoblots of NGAL protein in human serum samples from healthy subjects (Normal), or subjects with Acute Tubular Necrosis (ATN) or chronic renal failure (CRF), or from subjects with liver cirrhosis, hemochromatosis, or pancreatic carcinoma but lacking a renal diagnosis (Others), compared to NGAL Standards.
Figure 11C:
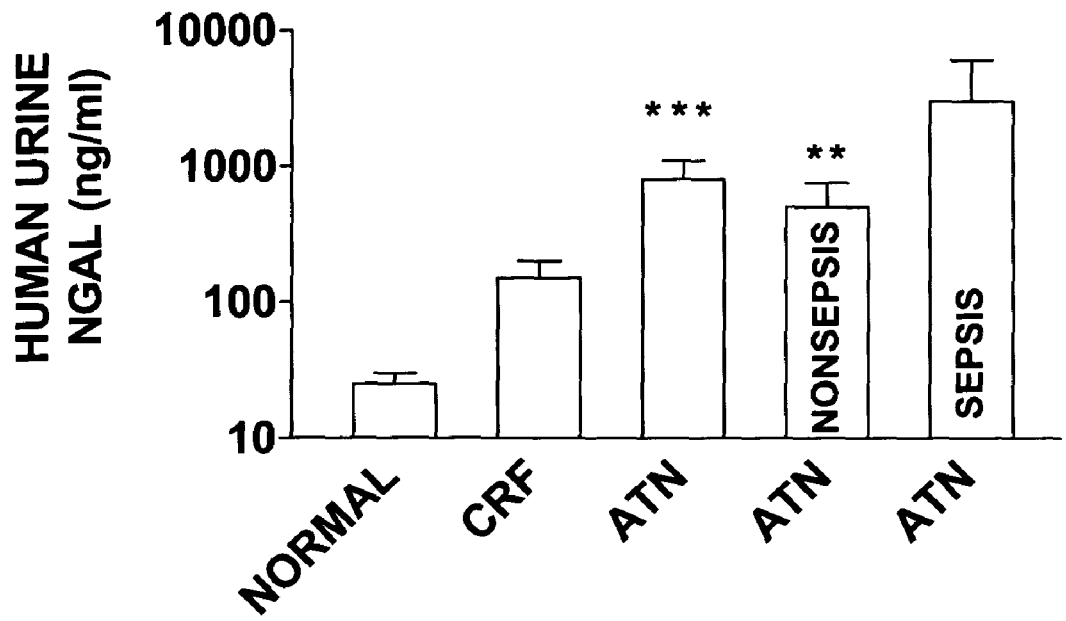
FIG. 11C shows a quantitative comparison of NGAL protein levels in urine from healthy subjects (Normal), or subjects with Acute Tubular Necrosis (ATN) or chronic renal failure (CRF). ATN is further subdivided into non-sepsis and sepsis groups.
Figure 11D:
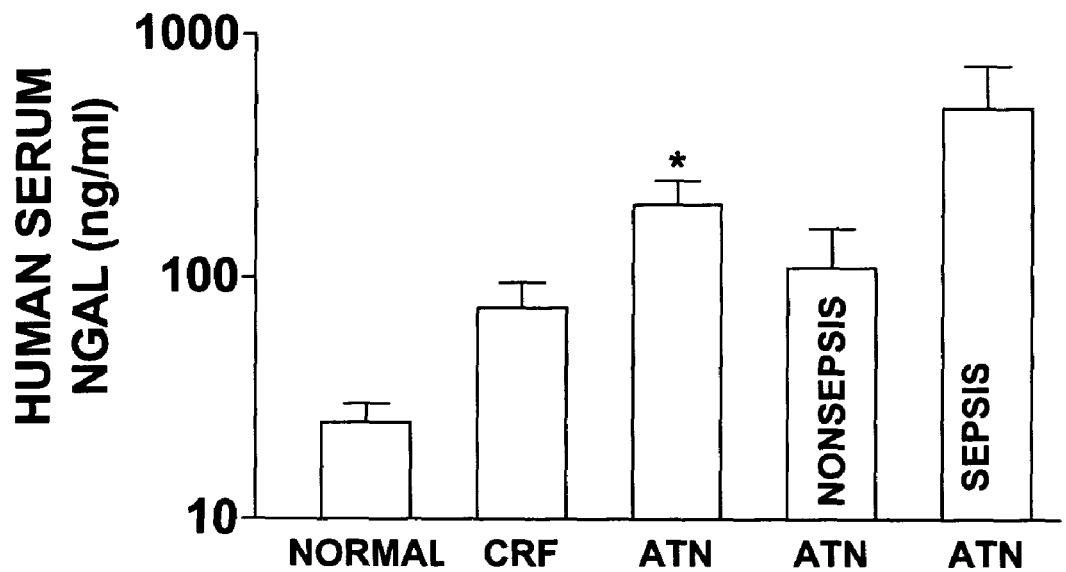
FIG. 11D shows a quantitative comparison of NGAL protein levels in serum from healthy subjects (Normal), or subjects with Acute Tubular Necrosis (ATN) or chronic renal failure (CRF). ATN is further subdivided into non-sepsis and sepsis groups.

Expression of NGAL increases in Acute Renal Failure of the Human. Acute renal failure in humans was marked by log order elevations in the concentration of serum and urinary NGAL protein, shown in FIG. 11. Urinary NGAL protein was 22 ng/ml (n=10) in normal subjects, and 557 ng/ml (25-fold elevation, p<0.001) in subjects with acute renal failure and a variety of co-morbidities. Urinary NGAL immunoblots are shown in FIG. 11A, and as quantitative graphs in FIG. 11C. Compared to normal subjects, in which serum NGAL was 21 ng/ml (geometric mean; n=5) subjects with acute renal failure and a variety of co-morbidities had 7.3-fold elevations in serum NGAL (146 ng/ml, p<0.05). These data are shown as immunoblots in FIG. 11B, and as quantitative graphs in FIG. 11D. Patients with acute renal failure associated with bacterial infection tended to have the highest levels of serum (331 ng/ml) and urinary (2786 ng/ml) NGAL, but this was not statistically different from acute renal failure without infection. To determine whether NGAL expression correlated with the extent of acute renal impairment, we used simple regression analysis after log transformation of NGAL levels. We found both serum (r=0.64, n=32) and urinary NGAL levels (r=0.68, n=38), as well as urine NGAL normalized for urine creatinine (r=0.67, n=36) were highly correlated with serum creatinine levels (p<0.0001). In comparison, patients with chronic renal failure had less prominent elevations in serum NGAL (49 ng/ml, n=10) and urine NGAL (119 ng/ml, n=9), and these values failed to correlate with serum creatinine. These data correlate NGAL expression with acute kidney damage, implicating the kidney as the major source of serum and urinary NGAL. Indeed, in several cases of severe renal failure, the fractional excretion of NGAL (the clearance of NGAL, normalized for the clearance of creatinine) was greater than 100%, demonstrating that urinary NGAL derived from local synthesis, rather than only by filtration from the blood. By comparison, mouse urine also contained markedly elevated levels of NGAL, shown in FIG. 11E, following induction of ATN injury.

Figures 12A, 12B, 12C, 12D, 12E, 12F, 12G, 12H, 12I:
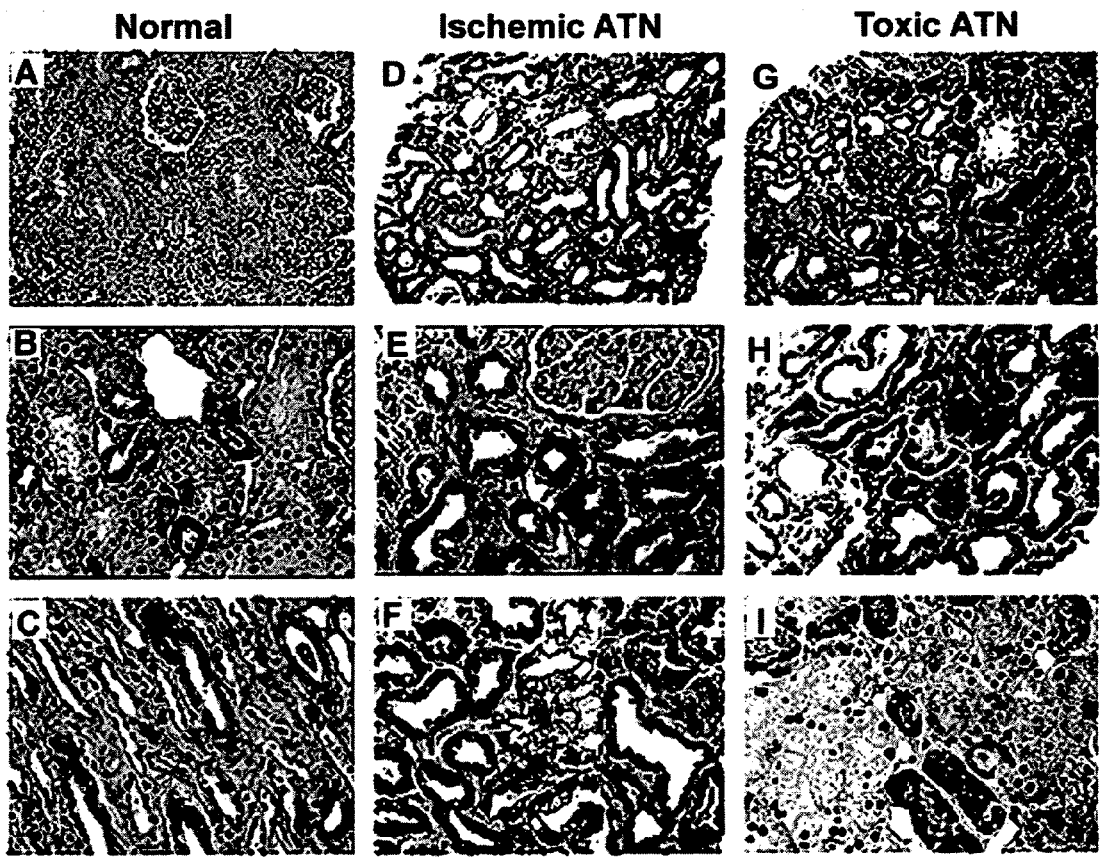
FIG. 12A shows immunohistochemical staining for NGAL in a healthy human kidney (Normal).
FIG. 12B shows immunohistochemical staining for NGAL in a healthy human kidney.
FIG. 12C shows immunohistochemical staining for NGAL in a healthy human kidney.
FIG. 12D shows increased immunohistochemical staining for NGAL in a human kidney with ischemic ATN caused by sepsis (Ischemic ATN).
FIG. 12E shows increased immunohistochemical staining for NGAL in a human kidney with ischemic ATN caused by hypovolemia due to vomiting and diarrhea.
FIG. 12F shows increased immunohistochemical staining for NGAL in a human kidney with ischemic ATN caused by heart failure.
FIG. 12G shows increased immunohistochemical staining for NGAL in a human kidney with toxic ATN caused by nephrotoxicity due to bisphosphonate (Toxic ATN).
FIG. 12H shows increased immunohistochemical staining for NGAL in a human kidney with toxic ATN caused by nephrotoxicity due to cephalosporin toxicity.
FIG. 12I shows increased immunohistochemical staining for NGAL in a human kidney with toxic ATN caused by nephrotoxicity due to hemoglobinuria.
Figures 12J, 12K:
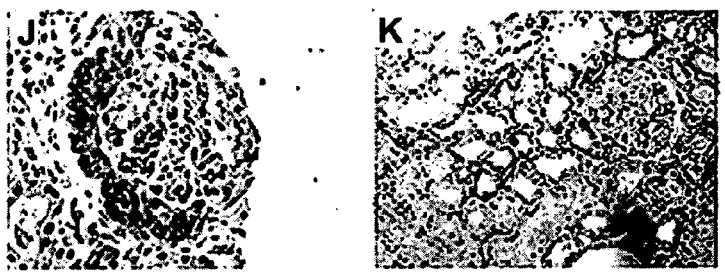
FIG. 12J shows immunohistochemical staining for NGAL in a human kidney with glomerular disease, with NGAL weakly expressed in crescents.
FIG. 12K shows immunohistochemical staining for NGAL in a human kidney with glomerular disease, with NGAL weakly expressed in the proximal tubules of nephrotics.

To visualize sites of expression of NGAL in acute renal diseases, human kidney tissue sections were stained with affinity-purified polyclonal antibody to NGAL (FIG. 12). The normal kidney demonstrated very weak staining in the distal tubular epithelia (mean 10% of cortical area) and in medullary collecting ducts, shown at low power in FIG. 12A, and at high power in FIGS. 12B, and 12C. Rare focal staining of glomerular parietal epithelial cells, but not other glomerular cells was also identified. Proximal tubules however were entirely negative. In contrast, nearly 50% of cortical tubules were stained for NGAL in kidneys exposed to nephrotoxins or ischemia in kidney sections from subjects with the following diagnoses: FIG. 12D, ischemic ATN caused by sepsis; FIG. 12E, hypovolemia (acute loss of blood volume); FIG. 12F, heart failure; FIG. 12G, nephrotoxicity due to bisphosphonate; FIG. 12H, nephrotoxicity due to cephosporin; and FIG. 12I, hemoglobinuria. NGAL was also widely expressed in the proximal tubule of patients with proliferative glomerulopathies, shown in FIGS. 12J and 12K, but to a lower degree than that found in ischemic damage (percentage of cortical parenchyma positive for NGAL was 20% in minimal change disease, 40% in diabetic nephropathy and 50 and 65% in ANCA and anti-glomerular basement membrane diseases). Tubular cells displaying features of cell injury, including simplification and enlarged reparative nuclei with prominent nucleoli, had the most intense staining. Tubular cells with less derangement had much less staining. These data demonstrate de novo and widespread NGAL reactivity in cortical tubules of different renal diseases and demonstrate that NGAL expression is a common response of damaged epithelia in human kidney.

Example 9

Figure 11E:
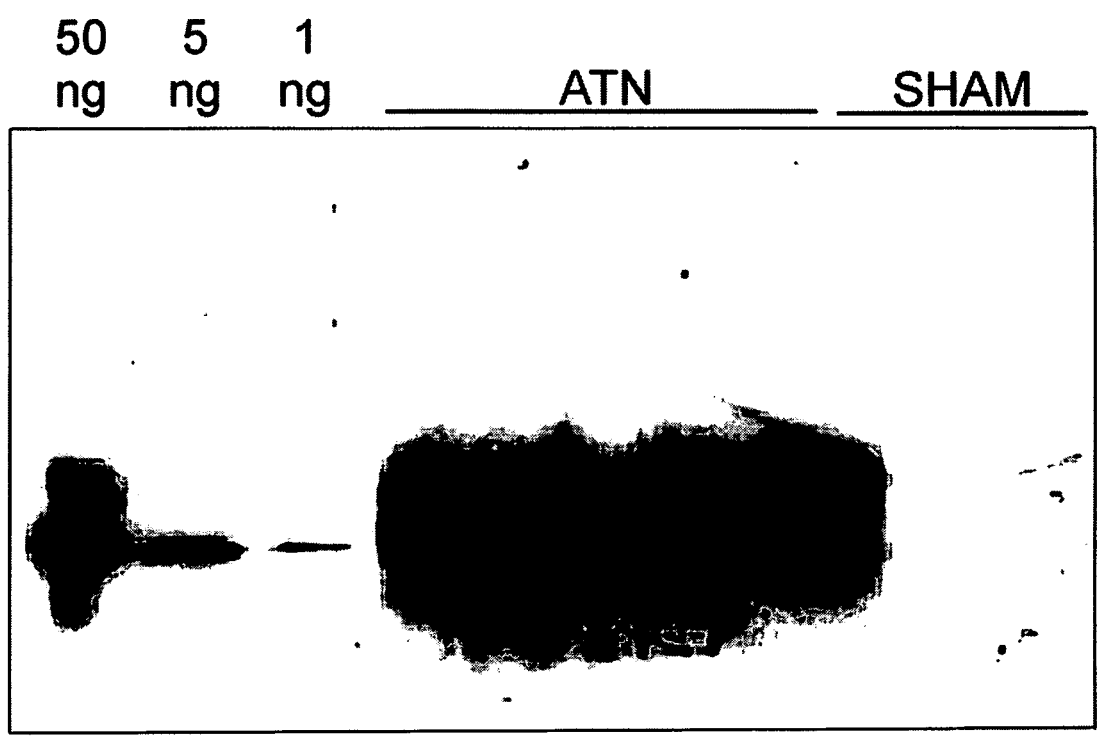
FIG. 11E shows an immunoblot of NGAL in urine from ATN-injured and Sham-treated control mice, along with standards of 50, 5, and 1 ng NGAL protein.

Exogenous NGAL Rescues the Mouse Proximal Tubule from ATN. To examine the functional significance of NGAL expression in renal ischemia, ATN injury was induced in mice. The renal artery was clamped for 30 min and the contralateral kidney was removed. Twenty-four hours after reperfusion, the plasma creatinine rose from $0.41\pm0.1$ mg/dl (n=4) to $3.16\pm0.17$ mg/dl (n=8; p<0.001) and NGAL mRNA message and protein were intensely expressed. NGAL mRNA levels rose approximately 1000 fold, reducing the threshold for detection by Real-Time PCR from $17.7\pm0.87$ cycles in sham kidneys to $7.52\pm0.44$ cycles (p<0.0001, n=4 each) in ischemic kidneys (normalized to beta actin mRNA levels). NGAL protein rose 1000 fold in the urine (40 µg/ml in ATN compared to 40 ng/ml in the sham operated and normal mouse, as shown in FIG. 11E), 300 fold in the blood (30 µg/ml in ATN compared to 100 ng/ml in the sham-operated mouse) and was elevated close to 100 fold in kidney extracts (Average 73 µg/g compared to <1 µg/g kidney wet weight in sham-operated kidney, n=3, p<0.05). The amount of NGAL protein in the kidney correlated well with the duration of cross-clamping.

To determine whether NGAL was protective in the ischemic model of ATN, we introduced NGAL systemically (1-300 µg by subcutaneous or intraperitoneal injection) prior to, or within one hour of the release of the arterial clamp. Injection of µg 100 NGAL 15 minutes before clamping blocked the rise in plasma creatinine measured 24 hours after reperfusion ($1.18\pm0.18$ mg/dl, n=7; compared to $3.16\pm0.17$ mg/dl in untreated animals). Similar data were obtained for dosages ranging from 10-300 µg of NGAL, but 1 µg NGAL was not protective (creatinine=$3.09\pm0.11$ mg/dl, n=3). Introduction of NGAL one hour after reperfusion also blocked the azotemia (creatinine=$1.60\pm0.28$, n=3, p<0.001), but to a lesser degree than pre-treatment with NGAL. These data were confirmed by measurement of the blood urea nitrogen (data not shown).

Figure 13A:
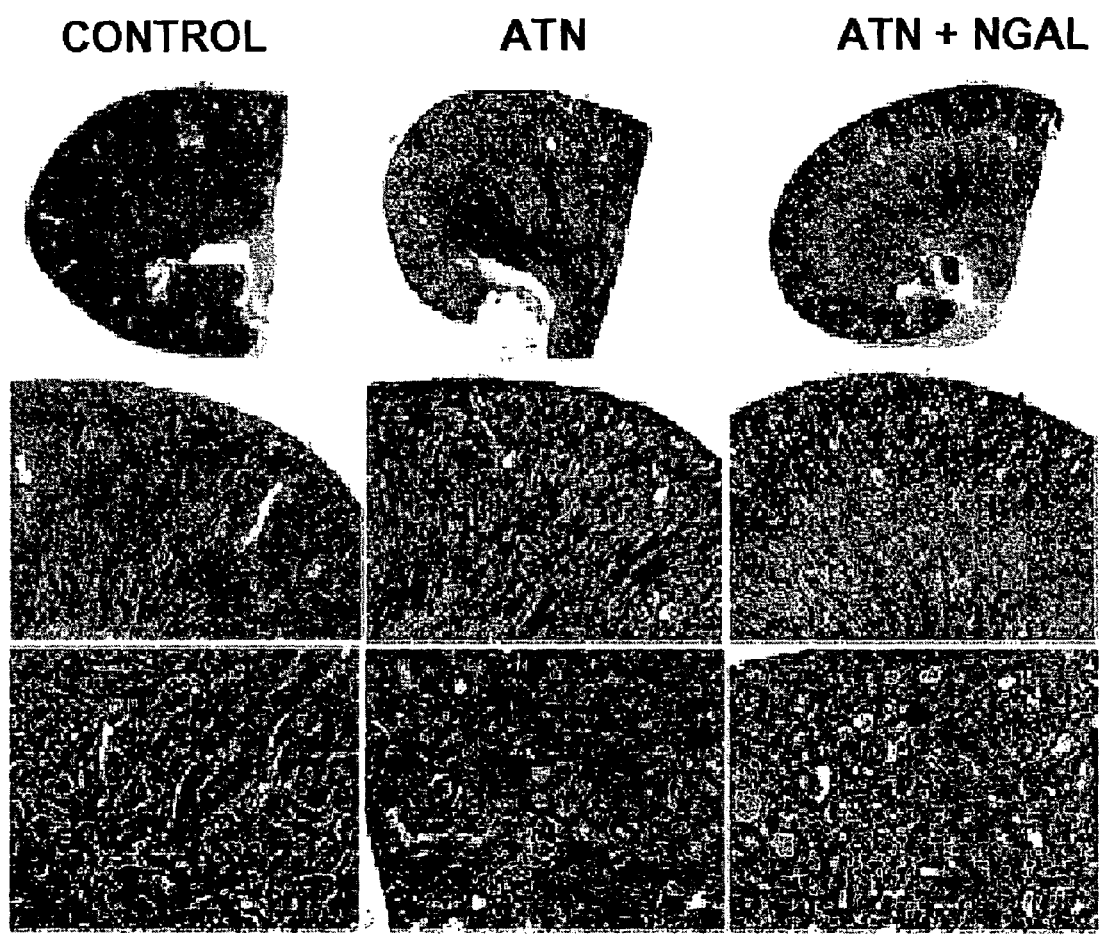
FIG. 13A shows histological sections of sham-treated (Control), ischemic (ATN), and NGAL-treated ATN-injured (ATN+Ngal) kidneys. Loss of tubular nuclei is observed in ATN but not control or ATN+Ngal sections (upper panels), as well as cortical (center panels) and medullary (lower panels) intratubular casts. NGAL pretreatment resulted in preservation of cortical tubules, but residual cortical-medullary casts.
Figure 13B:
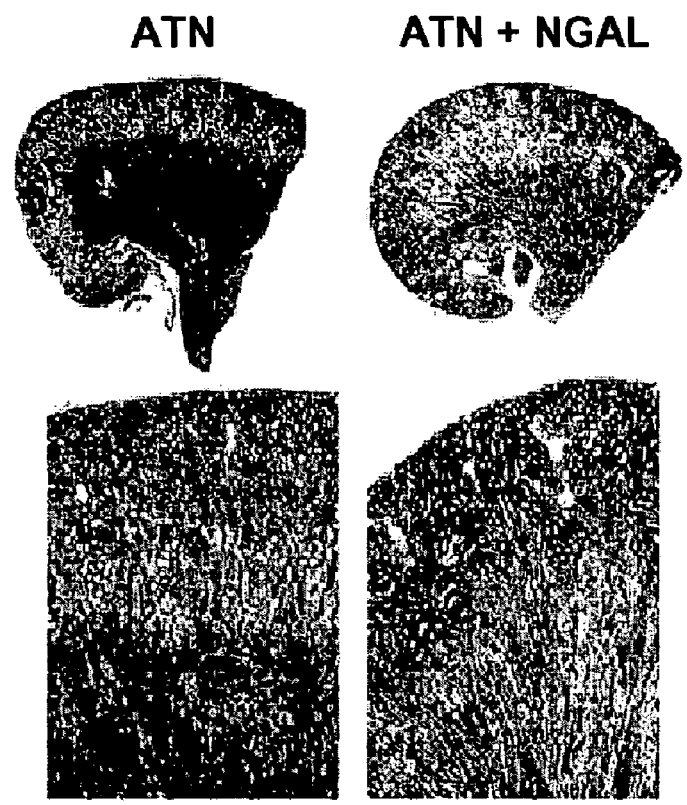
FIG. 13B shows histological sections of ischemic (ATN), and NGAL-treated ATN-injured (ATN+Ngal) kidneys, with PAS staining highlighting the luminal casts and the rescue of cortical tubules by pre-treatment with NGAL.
Figure 13C:
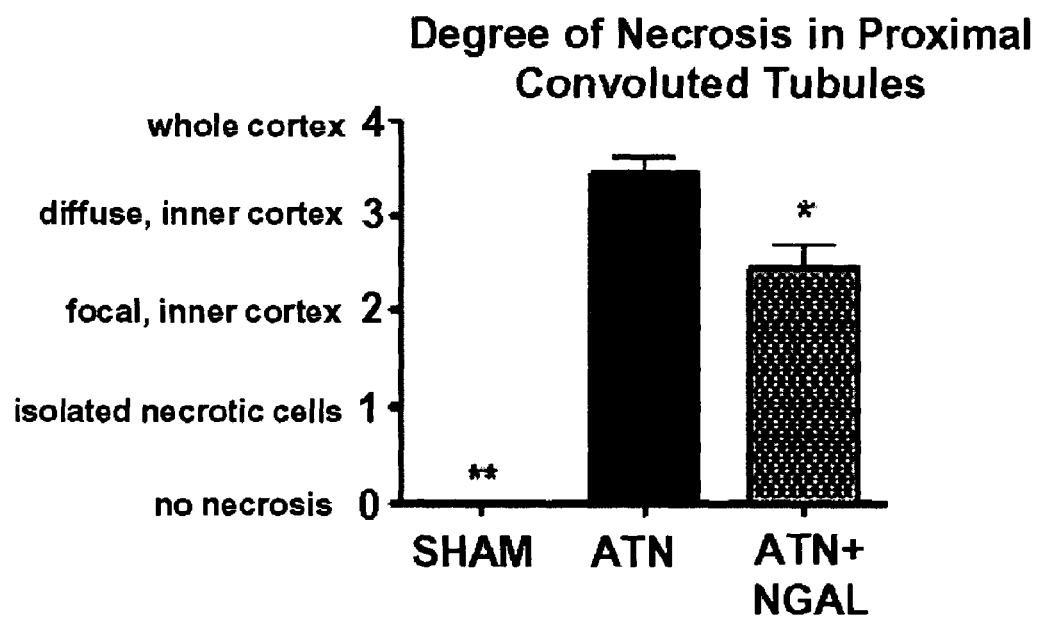
FIG. 13C shows Jablonski scoring of sham-treated (Sham), ischemic (ATN), and NGAL-treated ATN-injured (ATN+ Ngal) kidneys to demonstrate rescue of the ischemic cortex by NGAL.

The activity of NGAL was also demonstrated by histological findings that rather than necrotic tubules and luminal debris, normal epithelial morphology was preserved in the S1 and S2 segments of the proximal tubule, shown in FIG. 13A, in Control and NGAL-treated kidneys (ATN+NGAL), compared to ATN kidneys. The S3 segment in the outer stripe of the outer medulla was less protected by injection of NGAL, but tubular casts were less evident, shown in FIG. 13B. These observations were supported by Jablonski scoring of the sections, shown in FIG. 13C. In contrast, treatment with NGAL 2 hours after ischemia had no protective effect (creatinine=$3.12\pm0.35$ mg/dl, n=3).

Example 10

Figure 14A:
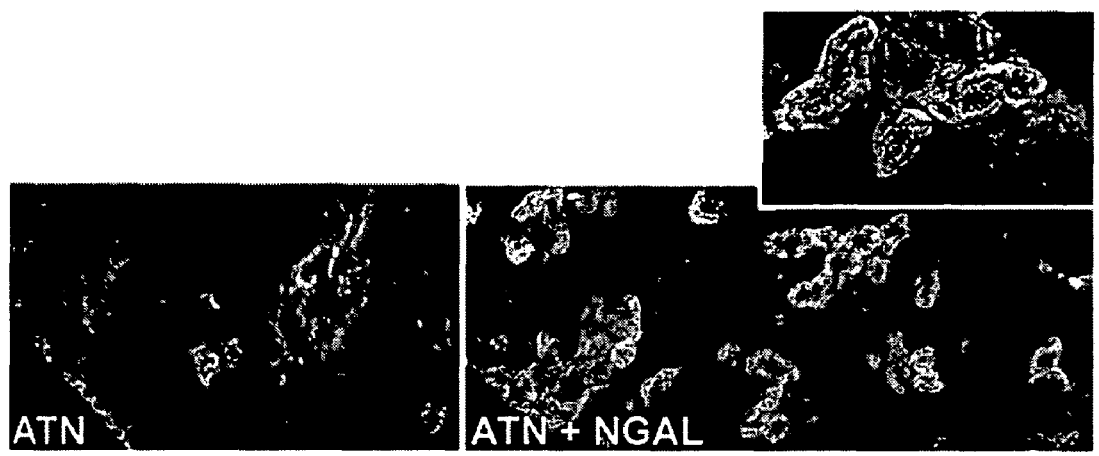
FIG. 14A shows N-cadherin staining in kidney sections is nearly abolished by ischemia reperfusion (ATN), but is rescued when NGAL is administered (ATN+Ngal).
Figure 14B:
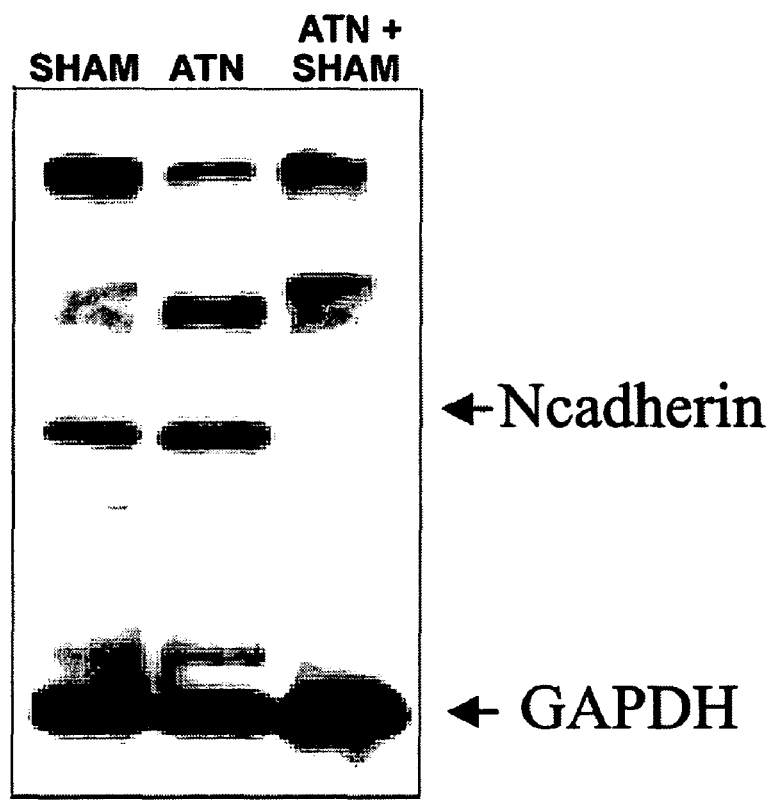
FIG. 14B shows full length N-cadherin protein levels are rescued by NGAL treatment (ATN+Ngal), compared to ischemic (ATN), as indicated by the N-cadherin fragments (arrow) in ischemia-reperfusion and sham-treated animals, but their suppression in NGAL-treated animals. GAPDH is the loading control.

Correlates of Ischemia Perfusion Injury. Because the trafficking and metabolism of the cadherins is rapidly affected by ischemia, and because NGAL acts as an inducer of E-cadherin in rat embryonic metanephric mesenchyme, NGAL rescues cadherin expression in the ischemic kidney. To test this hypothesis we first confirmed that while E-cadherin could be detected in mouse proximal tubules by immunofluorescence, N-cadherin was present in all segments of the proximal tubule, shown in FIG. 14A, and appeared to be its major cadherin. N-cadherin is known to be processed by caspases, β-secretase and by matrix metalloproteinases which generate 30-40 Kd cytoplasmic fragments which are potentially important signaling molecules that modulate CREB signaling. N-cadherin was degraded to a 30 Kd fragment after ischemia reperfusion, demonstrated by immunoblot in FIG. 14B, suggesting the activation of one or more of these pathways. In some animals degradation of the protein could be detected within 6 hours of reperfusion, and by 24 hours both N-cadherin immunofluorescence and the full-length protein was nearly abolished. In contrast, pre-treatment with NGAL preserved N-cadherin immunofluorescence, enhanced the expression of full length N-cadherin and reduced the appearance of its fragment when monitored at 6 hours (in some animals) or 24 hours of reperfusion. Hence, the preservation of proximal tubule marker N-cadherin correlates with and is a sensitive marker of NGAL activity. E-cadherin, which is highly expressed in the distal tubule and collecting duct, was much less affected by ischemia and by NGAL treatment. Similarly, metal induced nephrotoxic ATN triggered the degradation of N-cadherin but not E-cadherin. One effect of NGAL, therefore, is to inhibit signaling by N-cadherin fragments.

Figure 14C:
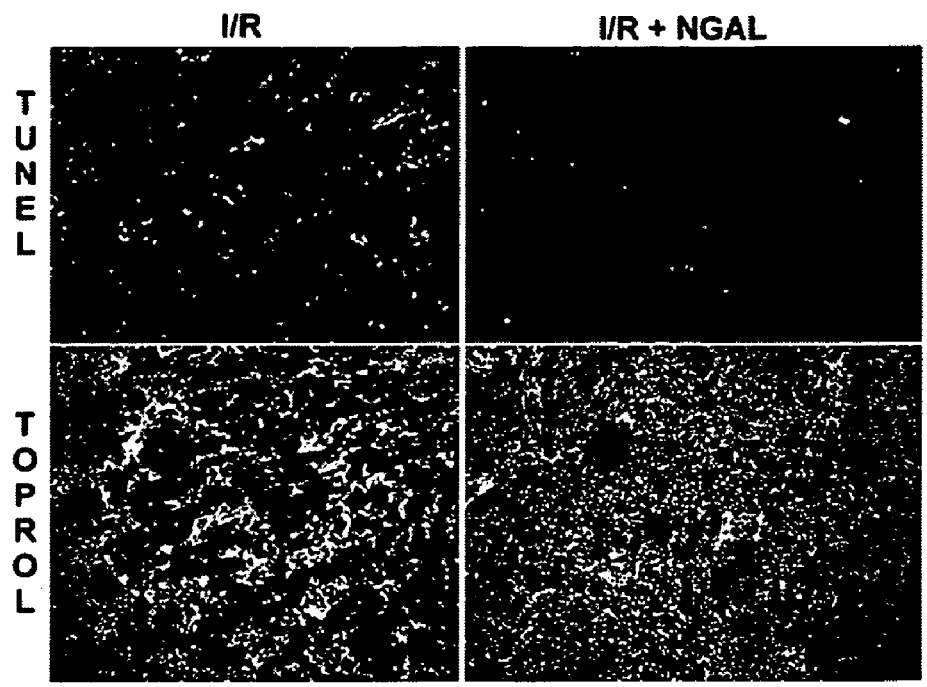
FIG. 14C shows tubules with TUNEL-positive apoptotic cells (fluorescence) in ischemic-reperfused mice (I/R) reduced by pretreatment with NGAL (I/R+Ngal). Toprol is the nuclear counterstain.
Figure 14D:
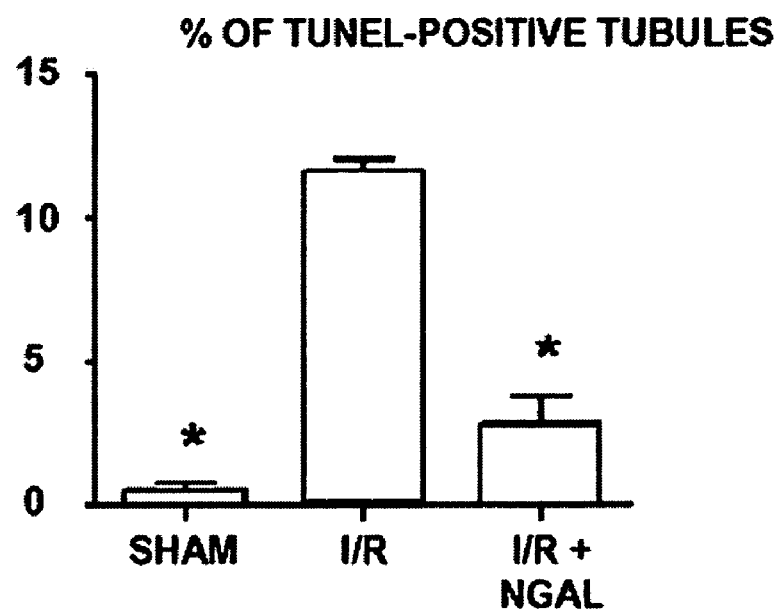
FIG. 14D shows a quantitative analysis of the percentage of tubules containing an apoptotic nucleus in sham-treated controls (sham), ischemic-reperfused (I/R), and ischemic-reperfused mice treated with NGAL (+Ngal).

Because disruption of the proximal cell results in apoptotic cell death, the effect of NGAL on cell viability was determined using a TUNEL assay of apoptosis induction. Twenty-four hours after reperfusion, we counted the percentage of tubules with at least one TUNEL-positive tubular cell, shown in FIG. 14C. Ischemic kidneys (I/R) showed 11.5%±0.6 (SEM, n=4 animals) of cortical tubules contained TUNEL-positive cells, but after treatment with NGAL (I/R+Ngal), the percentage of positive tubules fell to 2.9%+0.9 (SEM, n=7; p<0.001). By comparison, 0.5%±0.3 of cortical tubules had TUNEL-positive cells in sham kidneys, shown in the quantitative graph in FIG. 14D.

BrDU uptake was determined as a method to measure cell proliferation by determining the percent of cortical tubules with at least one BrDU-positive tubular cell in histological sections of kidneys (not shown). Ischemic cortical tubules contained rare BrDU-positive cells (1.9%±0.3; n=3) while ischemic kidneys pretreated with NGAL had a small but significant increase in positive cells (3.9%±0.5; n=4; p<0.05) measured 24 hours after the insult. By comparison, 3.7%±0.7 of cortical tubules had BrdU-positive cells in sham kidneys. Hence, rescue by NGAL reduced apoptosis of cortical cells and either stimulated compensatory tubular cell proliferation or rescued cells from damage.

Because the expression of NGAL correlates with ischemic damage, endogenous NGAL expression after treatment with exogenous NGAL protein was measured. Treatment of ischemic animals with 100 mg NGAL reduced the increase in endogenous NGAL RNA by 72%±16 (p<0.01; n=5) at 24 hours of reperfusion as measured by real time PCR. Treatment with 100 mg NGAL reduced the appearance of endogenous NGAL protein in the kidney by 2.5 fold (ischemia 73±7 µg/g; NGAL-treated ischemia, 29±7 µg/g; n=3 each; p<0.01) as measured by immunoblot, preserved tubular cells with proliferation potential.

Example 11

Figure 14E:
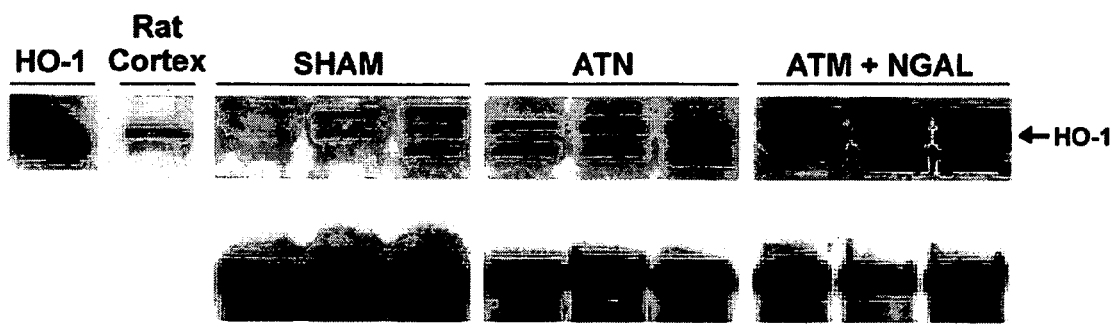
FIG. 14E shows an immunoblot of heme oxygenase-1 (HO-1) expression in sham-treated (Sham), ischemic-reperfused (ATN), or ischemic-reperfused NGAL-treated kidneys (ATN+Ngal). Recombinant HO-1 (HO-1) and rat cortex are included for comparison. GAPDH is the loading control.

NGAL Upregulates Heme Oxygenase-1 in ATN. A number of studies have identified heme oxygenase 1 (HO-1) as a critical regulator of the proximal tubule in renal ischemia. HO-1 is necessary for recovery from ATN and its level of expression is directly correlated with the rescue of tissue damage. As shown in FIG. 14E, ischemia reperfusion (ATN lanes) enhanced the expression of HO-1, but when ATN-injured mice were treated with 10-100 µg NGAL (ATN Ngal lanes), the enzyme was further upregulated 5-10 fold by 24 hours after reperfusion. To determine whether NGAL alone induced HO-1, healthy mice (Sham lanes) were injected with increasing doses of NGAL, and HO-1 protein levels were measured. However, the expression of HO-1 after NGAL injection was much less than the NGAL-treated ATN-injured kidneys, indicating that NGAL synergizes with other activators to upregulate HO-1 during ischemic-reperfusion events and protect the kidney from iron-mediated damage.

Example 12

Figure 15:
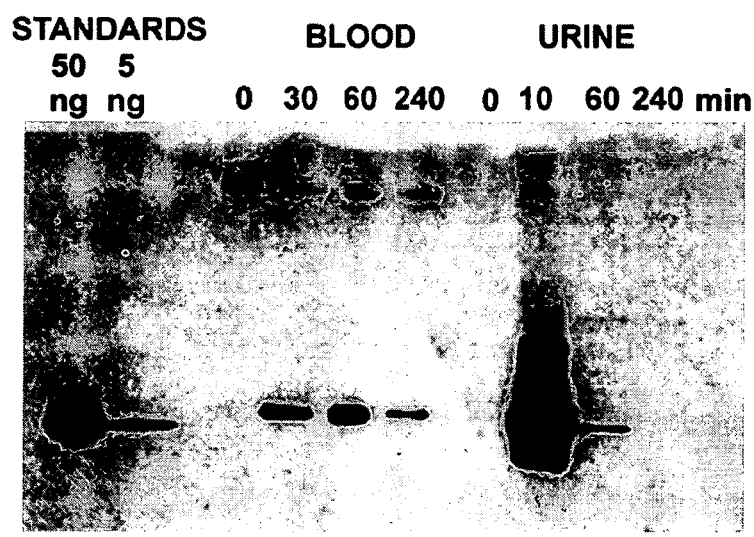
FIG. 15 shows an immunoblot of clearance of NGAL protein in blood and urine of mice following intraperitoneal injection of 100 μg NGAL.
Figure 16A:
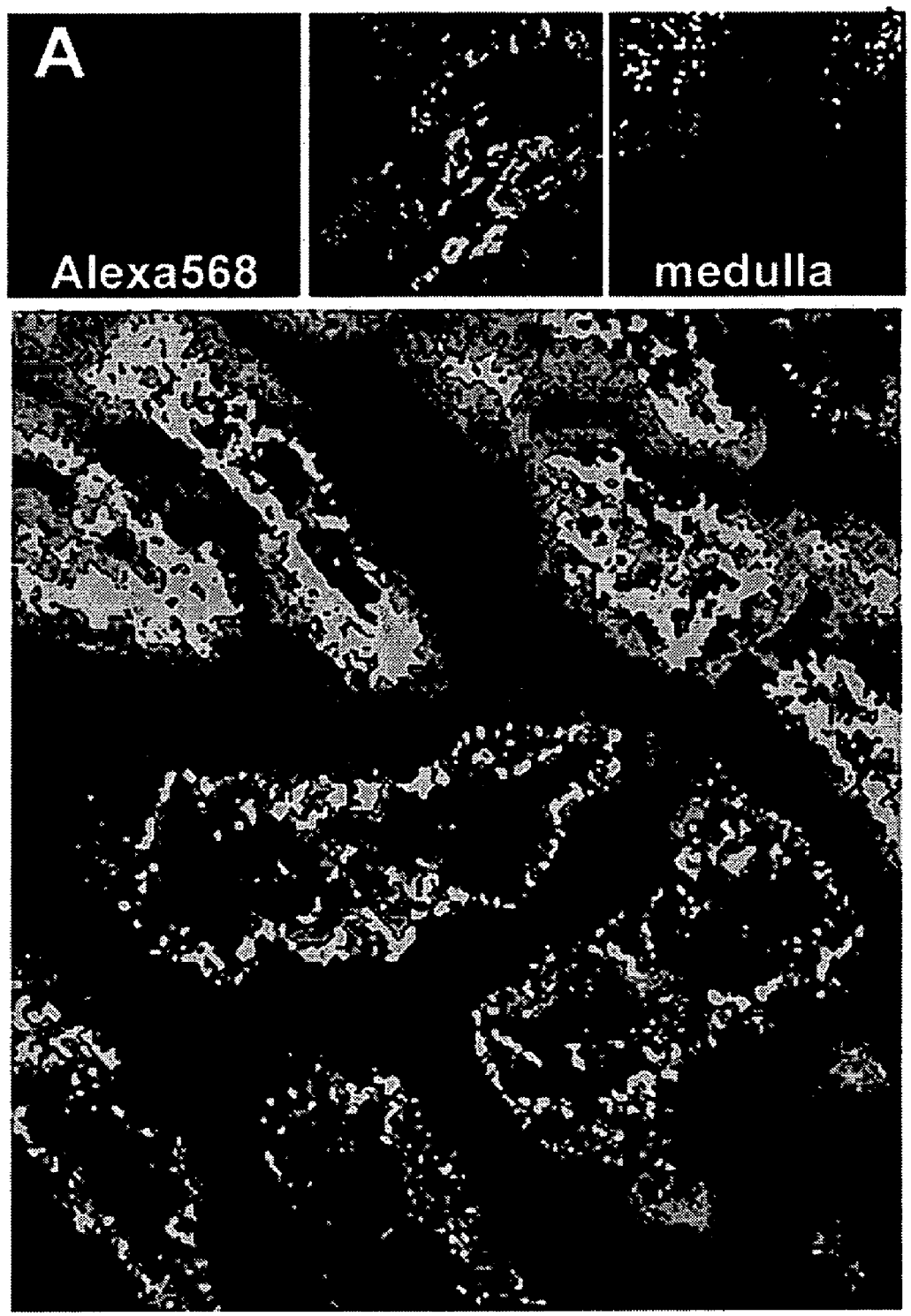
FIG. 16A shows fluorescent-labeled (Alexa568) NGAL localized to large vesicles in the proximal tubule (bottom panel) but not in the glomerulus or medulla (small top panels). Uncoupled fluorescent dye did not label the kidney.
Figure 16B:
FIG. 16B shows Alexa568-NGAL co-localized with FITC-dextran in S1 and S2 segments of the proximal tubule.
Figure 16C:
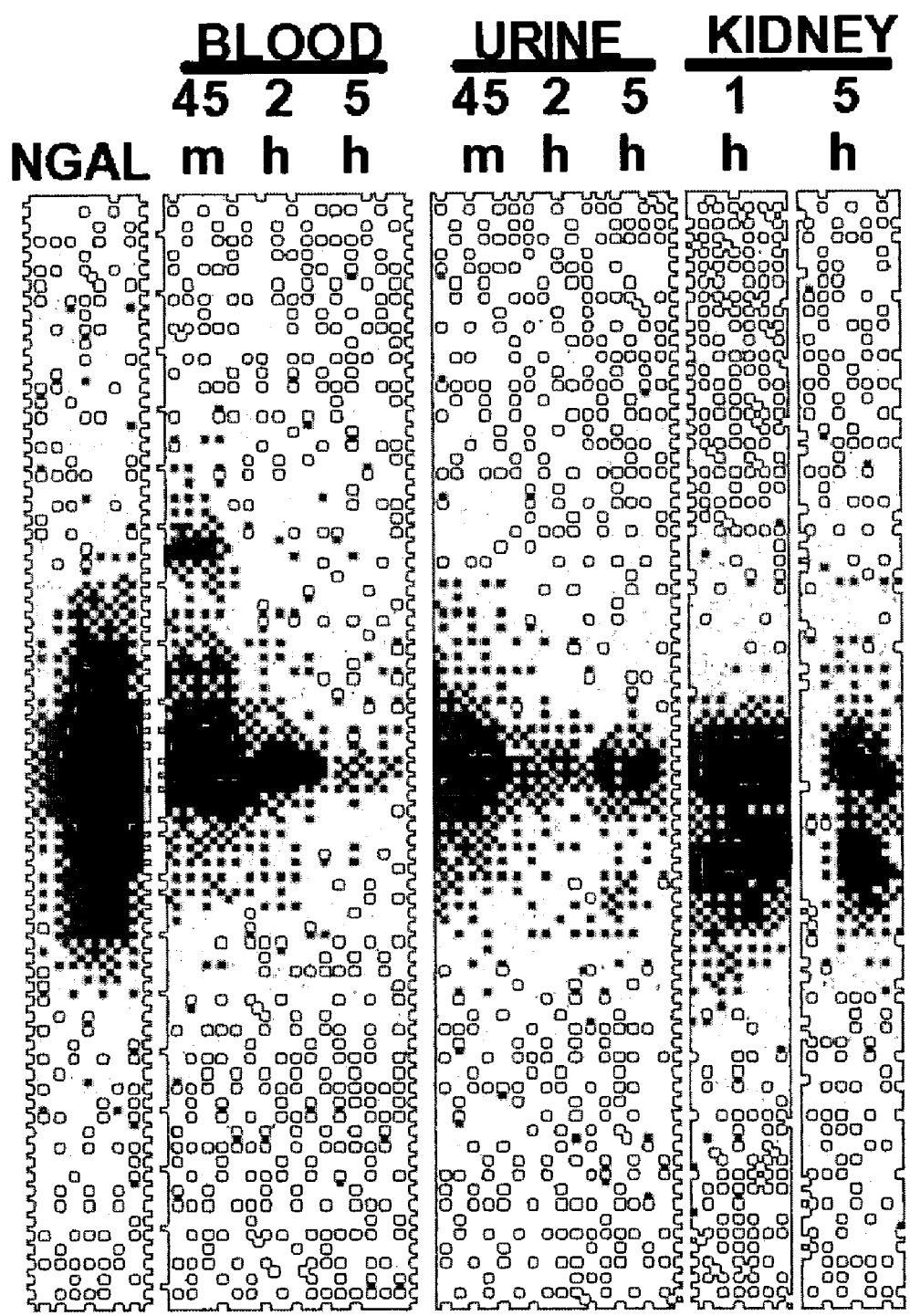
FIG. 16C shows SDS-PAGE separation of $^{125}$I-NGAL, with full length and a 14 kDa fragment of NGAL found in the kidney 1 and 5 hours after injection.

Mechanism of Rescue from ATN: NGAL Targets the Proximal Tubule. Distribution of exogenous NGAL was determined after an intraperitoneal or subcutaneous injection to establish the mechanism by which NGAL protects the proximal tubule from ischemic damage. NGAL was found in the urine within 10 min of injection of 100 µg exogenous NGAL suggesting that the protein was rapidly cleared by the kidney, shown in FIG. 15. The same time course was observed following injection of 10 µg NGAL (not shown). However, only 0.1-0.2% of the injected NGAL was recovered in the urine in the first hour. To better follow trafficking, fluorescent conjugates of NGAL were administered. Both fluorescein- and Alexa-labeled NGAL localized to large vesicles in the subapical domain of the cortical proximal tubule (S1 and S2 segments of the nephron) by one hour, but not to other segments of the tubule, shown in FIG. 16A. It should be noted that protein trafficking itself is also unlikely to be the mechanism of renal protection because a second lipocalin, retinoid loaded RBP, which is also captured by the proximal tubule and degraded in lysosomes was ineffective (FIG. 6A). To determine if these organelles were lysosomes, we labeled proximal tubular lysosomes with fluorescein-dextran (43 kDa) the day before administering Alexa-568 NGAL. One hour after injecting NGAL, 33% of the NGAL vesicles also contained dextran, shown in FIG. 16B. In addition, many of these vesicles co-stained with the lysosomal marker LAMP1 (data not shown). Similar results were observed following injection of [$^{125}$I]-NGAL, FIG. 16C, which showed that the full length protein was rapidly cleared from the blood and located in the kidney by the one hour time-point. In fact, the kidney had 13-fold more [$^{125}$I]-NGAL than the liver/mg protein. Nearly identical data were previously reported with human NGAL, which rapidly cleared the circulation ($t_{1/2}$=10 minutes) and located in the kidney at levels 12-fold higher than the liver/mg protein. The kidney-localized protein was TCA precipitable (70%), and composed of both full-length NGAL and a specific 14 kDa degradation product. These species persisted, and were only slowly lost after 5 hours after injection. In contrast, the plasma, and particularly the urine contained mostly low molecular weight, TCA soluble [$^{125}$I]-fragments, (35% and 20% TCA precipitable, respectively).

These data show that full length NGAL is rapidly cleared by the proximal tubule where it traffics to lysosomes and degrades to a 14 kDa fragment. It is likely that the endogenous protein (low levels of serum NGAL) traffics in a similar manner, because there is very little urinary NGAL in normal mouse or human urine, despite the fact that it is freely filtered from the circulation (human: filtered load=20 ng/ml×GFR, whereas urine NGAL=22 ng/ml; mouse: filtered load=100 ng/ml×GFR, whereas urine NGAL=40 ng/ml).

Example 13

Rescue of the Proximal Tubule from ATN Requires Fe:Siderophore. To determine if NGAL can deliver iron to the proximal tubule, NGAL was saturated with the radionuclide iron species $^{55}$Fe by incubating iron-free enterochelin-NGAL (Sid:NGAL) with $^{55}$Fe at a 1:1 stoichiometry ($^{55}$Fe:Sid:N-GAL). One hour after injecting this radiolabeled $^{55}$Fe:Sid:NGAL complex (10 µg intraperitoneal), the majority of $^{55}$Fe was recovered in the kidney (55%), while only trace amounts were found in the plasma (4.3%), urine (0.6%), liver (2.4%), and spleen (0.2%). To determine the location of the $^{55}$Fe in the kidney, radioautography of tissue sections was performed. $^{55}$Fe was localized in the proximal tubule, particularly along the apical surface, beneath the brush border, as shown in FIG. 16E, and in Table 1, where $X^2$=21.2 and p=0.0017.

TABLE 1

| Location | SilverGains$^a$ (% Total) | Area$^b$ (% Point Count) | Relative SA$^c$ | $X^2$ |
|---|---|---|---|---|
| Lumen | 26.46 | 18.49 | 1.43 | 3.43 |
| Apical MB | 12.91 | 5.84 | 2.21 | 8.54 |
| Cytosol | 48.98 | 48.81 | 1 | 0.00062 |
| Nucleus | 4.02 | 7.17 | 0.56 | 1.39 |
| Basal MB | 3.81 | 6.41 | 0.59 | 1.06 |
| Interstitium | 3.71 | 12.2 | 0.3 | 5.91 |
| Glomerular Tuft | 0.13 | 1.16 | 0.11 | 0.91 |

Key:
$^a$Total silver grains = 2601
$^b$Total point count = 999
$^c$% grains/% point count.

Figure 16D:
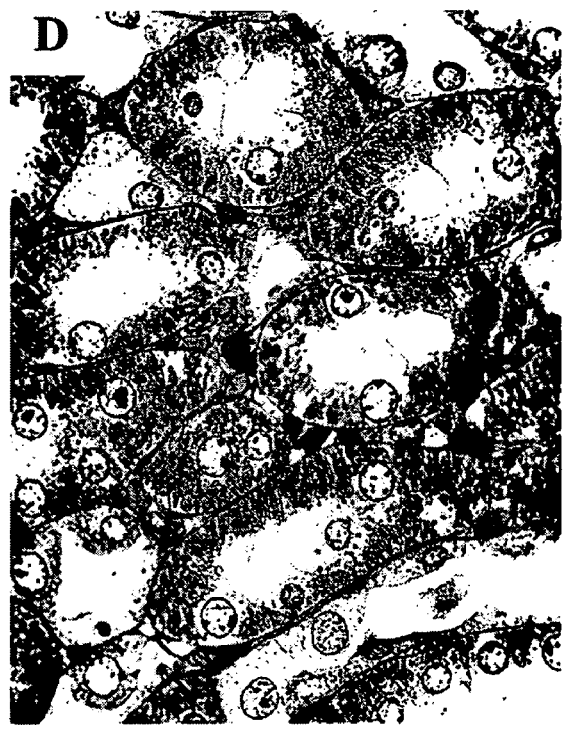
FIG. 16D shows radioautograph of kidney one hour after intraperitoneal injection of $^{55}$Fe loaded siderophore-NGAL. Radioactive decay is found in the cortex and is associated with the apical zones of proximal tubule cells FIG. 16E show radioautograph of kidney one hour after intraperitoneal injection of $^{55}$Fe loaded siderophore-NGAL, with no radioactivity was found in the medulla.
Figure 16E:
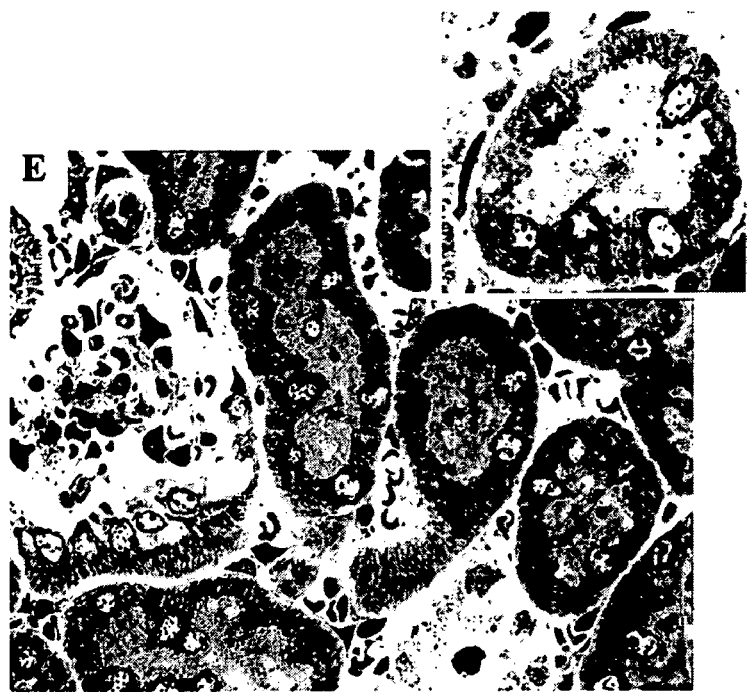

In contrast, $^{55}$Fe was not found in the medulla, shown in FIG. 16D. These data demonstrate that both the NGAL protein and its ligand, iron, can be captured by the proximal tubule when exogenous $^{55}$Fe:Sid:NGAL complex is injected. It should be noted that the distribution of $^{55}$Fe:Sid:NGAL was quite different from the distribution of non-protein bound $^{55}$Fe citrate, wherein only 1.5% of the iron was recovered in the kidney (not shown).

Example 14

Figure 17A:
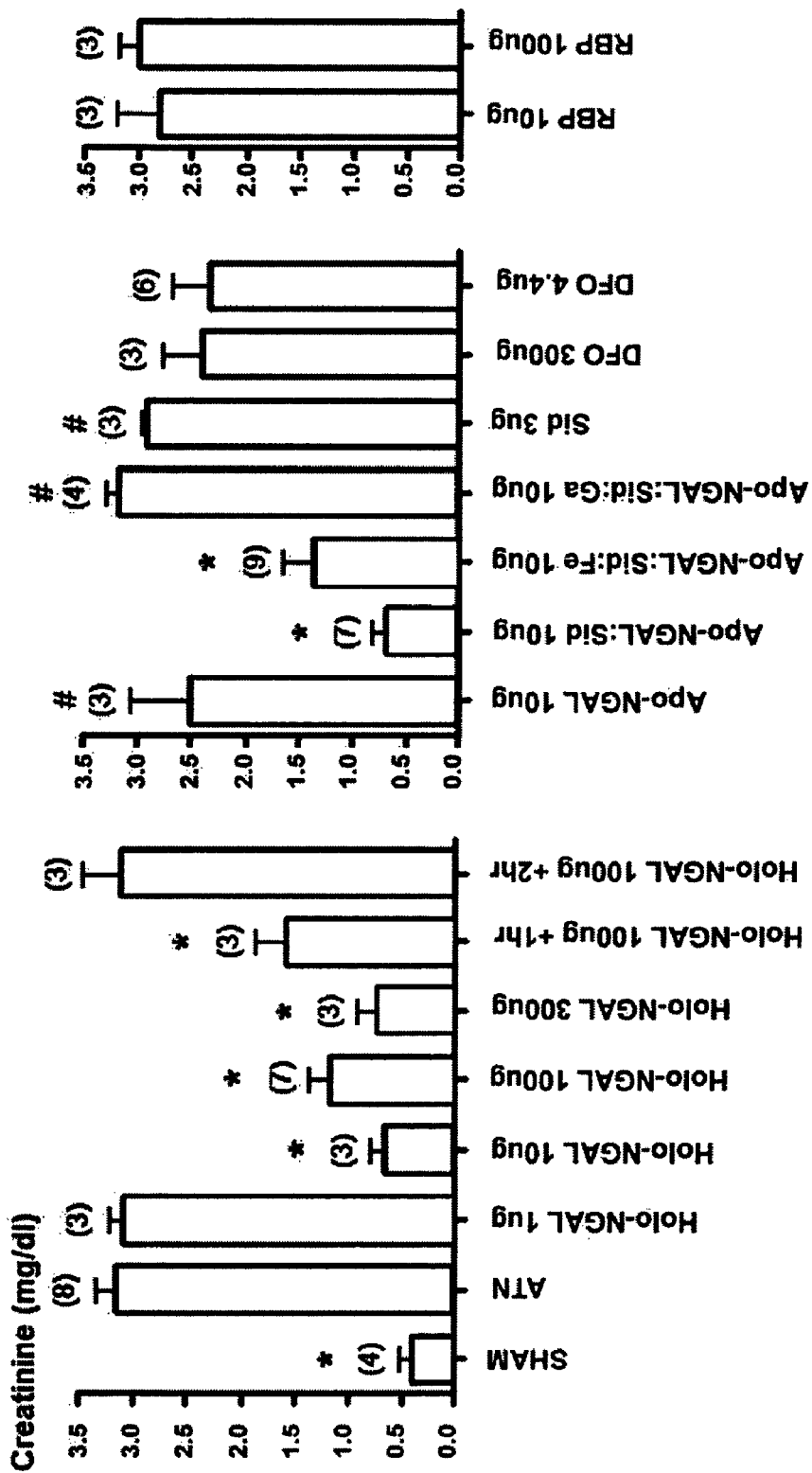
FIG. 17A shows plasma creatinine in mice subjected to 30 minutes of ischemia. The first panel shows that holo-NGAL ($\geqq 1$ μg) from XL-1 bacteria (containing siderophore) rescues renal function when introduced 15 minutes prior to ischemia or within one hour after ischemia. However, NGAL is ineffective when administered later. The second panel shows that apo-NGAL from BL-21 bacteria (siderophore free) is minimally active, but when loaded with enterochelin, the protein is protective. Both iron-free (apo-NGAL:Sid) and iron-loaded siderophores (apo-NGAL:Sid:Fe) have protective effect. In comparison, the gallium-loaded complex (apo-NGAL:Sid:Ga) was ineffective as was a single dose of DFO or the free siderophore (Sid). Retinol Binding Protein (RBP), a lipocalin that is also filtered and reabsorbed by the proximal tubule was ineffective
Figure 17B:
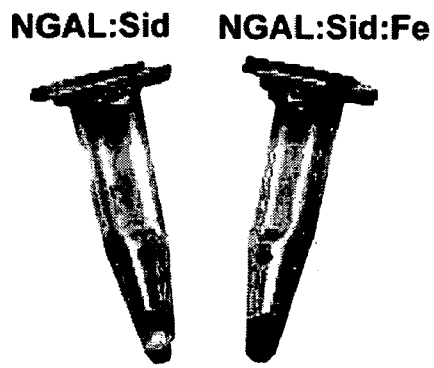
FIG. 17B shows immunoprecipitate preparations of NGAL. NGAL:Sid contains enterochelin, but not iron. NGAL:Sid:Fe contains siderophore and iron.

To determine the role of iron delivery in renal protection, we compared NGAL cloned in two different strains of E. coli bacteria. NGAL cloned in XL-1Blue bacteria contains enterochelin and is iron-loaded, while NGAL cloned in BL-21 bacteria does not contain enterochelin. Ten µg of XL-1Blue-cloned NGAL (holo-Ngal 10 µg, left panel) protected the kidney in comparison with sham-treated (Sham) and untreated ATN-injured kidney (ATN), shown in FIG. 17A. However, there was a reduced level of protection with 10 µg of BL-21-cloned NGAL (apo-Ngal 10 µg, center panel) lacking enterochelin. Therefore, BL-21-cloned NGAL was reconstituted with iron-free (apo-Ngal:Sid) and iron-saturated enterochelin (apo-Ngal:Sid:Fe). Loading with enterochelin (with or without iron) enhanced the protection of the kidney and blunted the rise in serum creatinine. The presence of iron was slightly less protective, since iron-saturated siderophore has a diminished capacity for chelating iron in the kidney. Because both the iron-loaded form and the iron free-form of NGAL:Sid were protective, it is possible that the siderophore itself, rather than iron was active. To test the role of iron further, a gallium:Sid:NGAL:Sid:gallium (apo-Ngal:Sid:Ga) complex was also tested. Because gallium is a metal that occupies iron binding sites with high affinity, including the enterochelin siderophore (gallium blocks $^{55}$Fe binding to enterochelin to the same extent as unlabeled iron), and because it can not undergo redox reactions typical of iron, gallium competes with iron for binding to the siderophore. In contrast to the iron complex, mice treated with the gallium complex 15 minutes prior to ischemia were not protected (creatinine=3.17±0.1; n=4). In addition, a single dose of free Siderophore (Sid), desferrioxamine mesylate (DFO) or retinol-binding protein (RBP) failed to protect against ATN. These data demonstrate that NGAL:siderophore complexes provide the protective activity of NGAL, and that iron transport by the siderophore is dependent upon NGAL. An immunoblot of NGAL:Siderophore complexes with or without iron (Fe) are shown in FIG. 17B.

Example 15

Figure 18A:
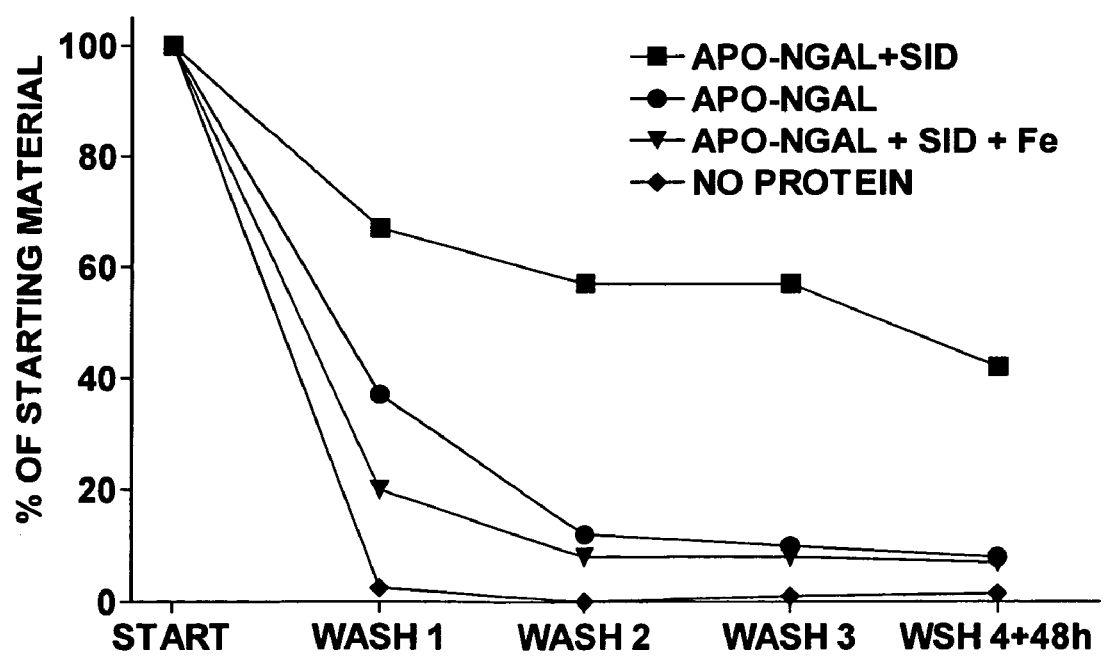
FIG. 18A shows that an iron-binding cofactor is present in urine. Buffer is mixed with $^{55}$Fe (no protein), with apo-NGAL, apo-NGAL+siderophore, or apo-NGAL+siderophore+unlabeled iron. After a series of washes, $^{55}$Fe is retained by apo-NGAL+siderophore but not by apo-NGAL or apo-NGAL ligated by the iron-saturated siderophore, demonstrating that an unsaturated siderophore is required for retention of $^{55}$Fe by NGAL.
Figure 18B:
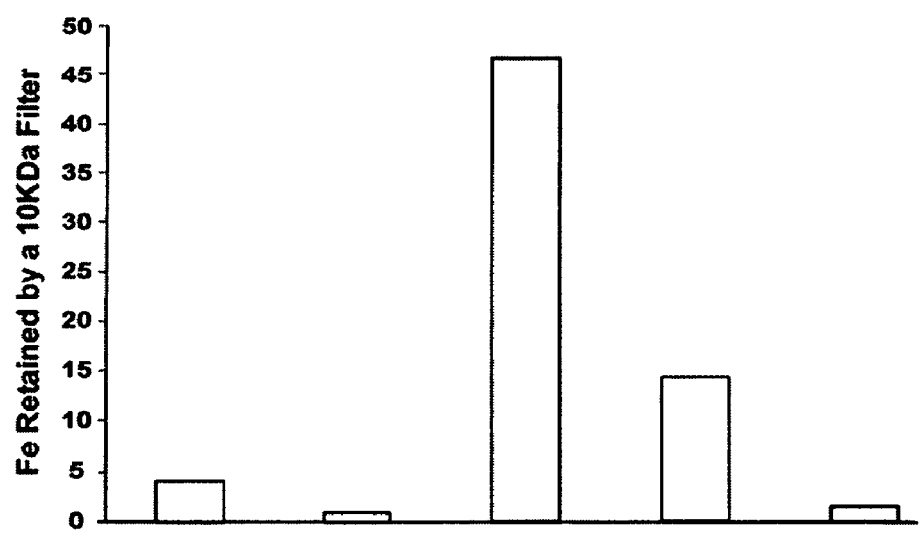
FIG. 18B shows that when urine (<3,000 Da) is mixed with $^{55}$Fe or with apo-NGAL, as indicated, and then washed three times on a 10 KDa filter, apo-NGAL+urine retains $^{55}$Fe. $^{55}$Fe retention was blocked by the addition of excess iron-citrate (Fe). Activity was also blocked by iron saturated enterochelin (Sid:Fe).

Demonstration of a Urine Siderophore. The actions of endogenous NGAL in vivo might differ from the pharmacological effect of exogenous NGAL, because the critical siderophore associated with exogenous NGAL is a bacterial product. The presence of endogenous low molecular weight factors that transport iron, however, have been suggested by a variety of studies. These molecules can include citrate, and related compounds, but also iron-transporting activities that have a molecular weight in the range of 1 Kd. To determine whether an NGAL co-factor is present in the urine, apo-NGAL from BL21 bacteria was mixed with urine samples from healthy mice. While the low molecular weight components of the urine (<3 Kd) failed to trap $^{55}$Fe above a 10 Kd cut-off filter, and apo-NGAL diluted in Tris or phosphate buffer failed to trap $^{55}$Fe, incubation of NGAL with urine (<3,000 Da) permitted the retention of $^{55}$Fe, shown in FIG. 18A. The capture of iron by NGAL was inhibited by the presence of 1000-fold unlabeled iron citrate, and more powerfully by a 50-fold concentration of iron-saturated enterochelin, shown in FIG. 18B. The capture of iron was saturable, and when using 30 µl of mouse urine, approximately 20% of NGAL molecules bound iron. These findings suggest that mouse urine contains a low molecular weight co-factor that permits NGAL-iron interactions. Because the endogenous factor is competitive with the bacterial siderophore, which binds the calyx with high affinity (0.4 nM), it appears that both bacterial and mammalian factors occupy the same binding pocket of the lipocalin.

Example 16

Figure 19:
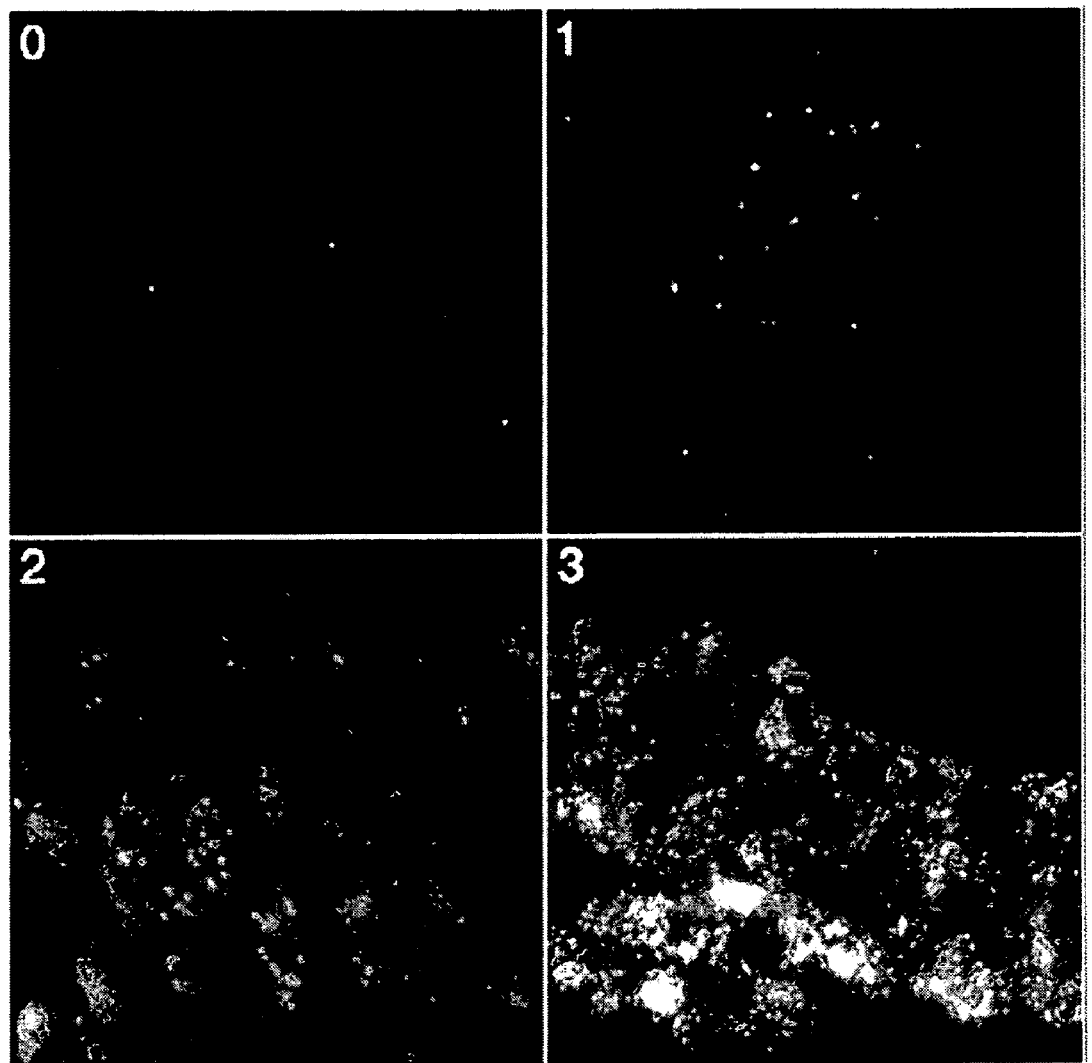
FIG. 19 shows kidney biopsies obtained within 1 hour of transplantation from living related (panels 0 and 1) or cadaveric (panels 2 and 3) kidney transplants. Sections were stained with NGAL antibody. NGAL expression was significantly increased in the cadaveric group, which underwent a longer ischemic period.

NGAL expression in patients undergoing kidney transplantation. Humans undergoing kidney transplantation were evaluated to determine NGAL expression during the recovery period. Kidney biopsies were obtained within 1 hour of transplantation from living related donors (LRD, n=10) or cadaveric (CAD, n=12) kidney transplants. Biopsy specimens were sectioned and immunohistochemically stained with NGAL antibody. NGAL expression was significantly increased in the CAD group, as shown in FIG. 19. Since cadaveric kidneys are maintained outside the body for a longer period of time than is typical for kidneys from living related donors, the degree of ischemic injury is generally greater, and was positively correlated by NGAL expression.

Figure 20:
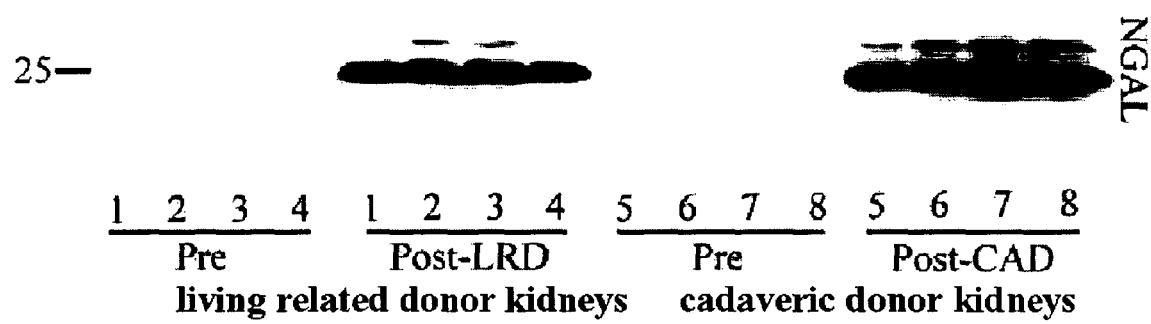
FIG. 20 shows Western blots of urine samples obtained within 2 hours of transplantation from living related (LRD, n=4) or cadaveric (CAD, n=4) kidney transplants, probed with NGAL antibody. NGAL expression in the urine was absent before the operation. NGAL expression was significantly increased in the CAD group compared to the LRD group
Figure 21:
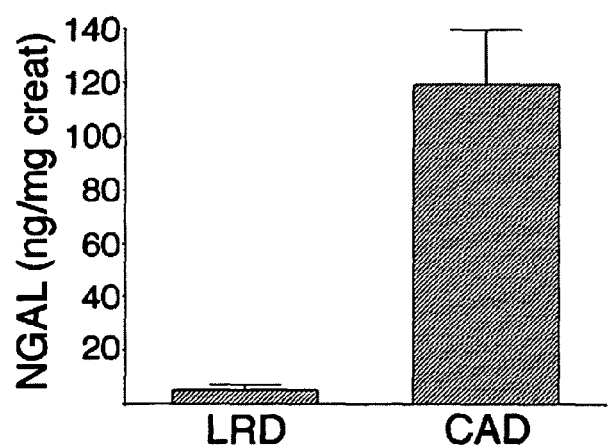
FIG. 21 shows quantitation of urinary NGAL by Western blots in LRD versus CAD, showing a significantly increased expression in CAD.
Figure 22:
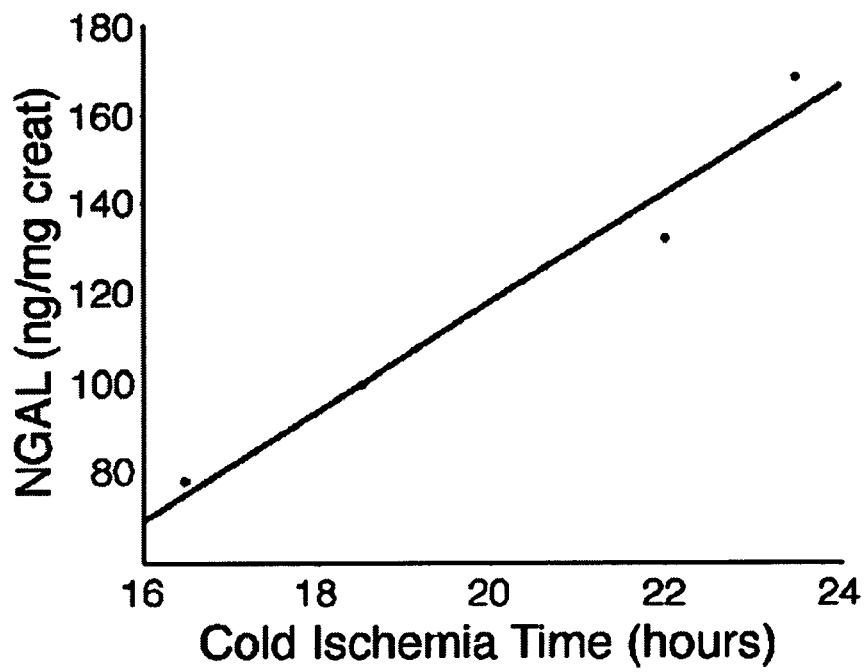
FIG. 22 shows the correlation of urinary NGAL obtained 2 hours after CAD transplantation with cold ischemia time. The degree of urinary NGAL expression correlates with ischemia time.

Western blots of urine samples obtained prior to transplantation, and within 2 hours of transplantation from LRD (n=4) or CAD (n=4) kidney transplants, shown in FIG. 20. NGAL expression in the urine was absent before the operation. NGAL expression was significantly increased in the CAD group compared to the LRD group. Quantitation of urinary NGAL measured by Western blots in LRD versus CAD showed a significantly increased expression in CAD, shown in FIG. 21. Quantitation by ELISA demonstrated similar results (not shown). This finding again correlated with the longer period of ischemia associated with CAD kidney transplantation. Correlation of urinary NGAL obtained 2 hours after CAD transplantation with cold ischemia time, shown in FIG. 22.

Figure 23:
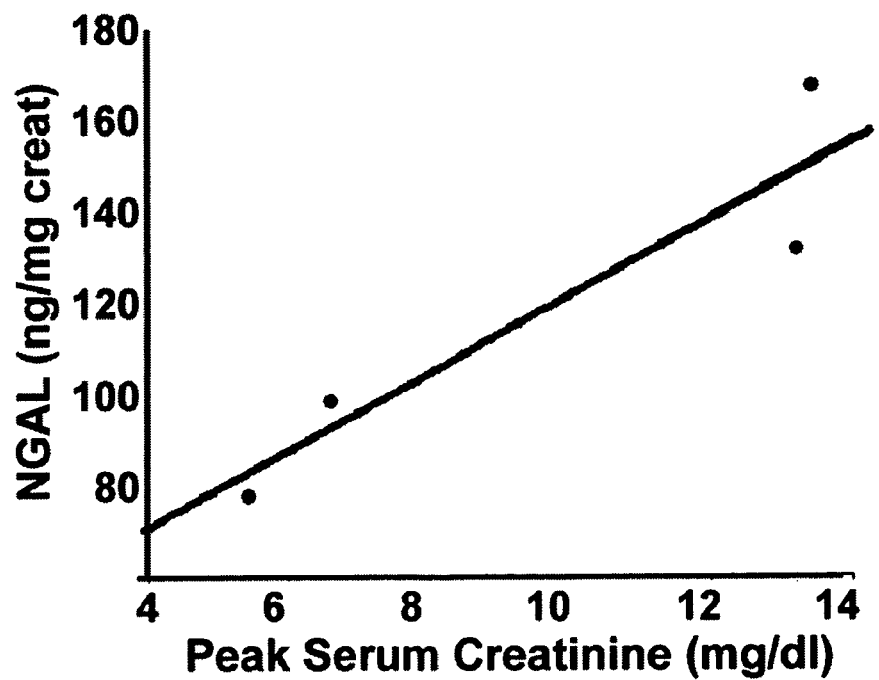
FIG. 23 shows the correlation of urinary NGAL obtained 2 hours after CAD transplantation with peak serum creatinine measured 2-4 days after the operation. The degree of urinary NGAL expression correlates with peak serum creatinine.

The serum creatinine levels, which peaked at 2-4 days after the transplant surgery occurred, also correlate with the urinary NGAL. Correlation of urinary NGAL obtained 2 hours after CAD transplantation with peak serum creatinine is shown in FIG. 23.

Example 17

Figure 24:
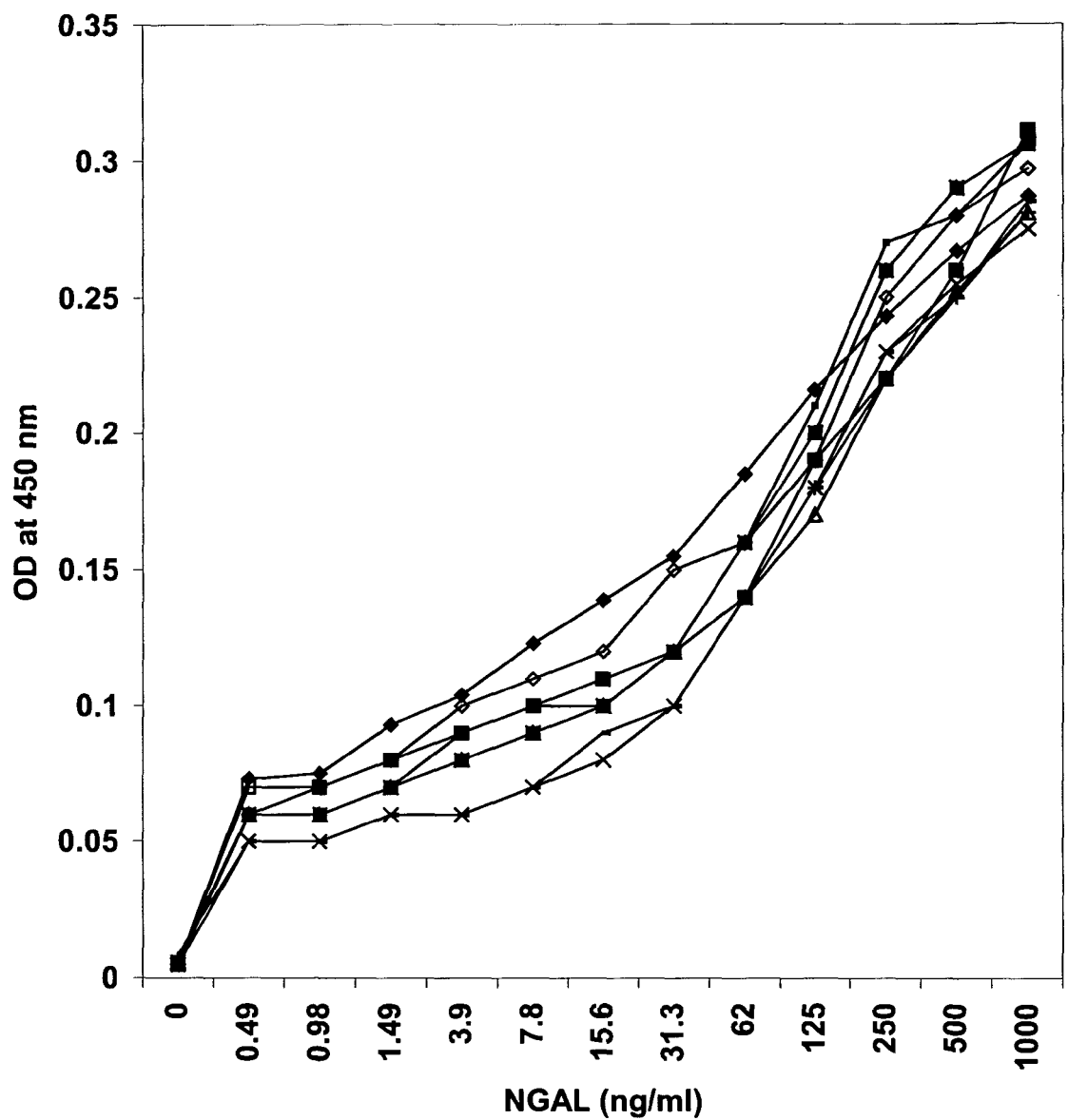
FIG. 24 shows standard curves for NGAL ELISA with the linear relationships obtained from 10 independent standard curves.
Figure 25:
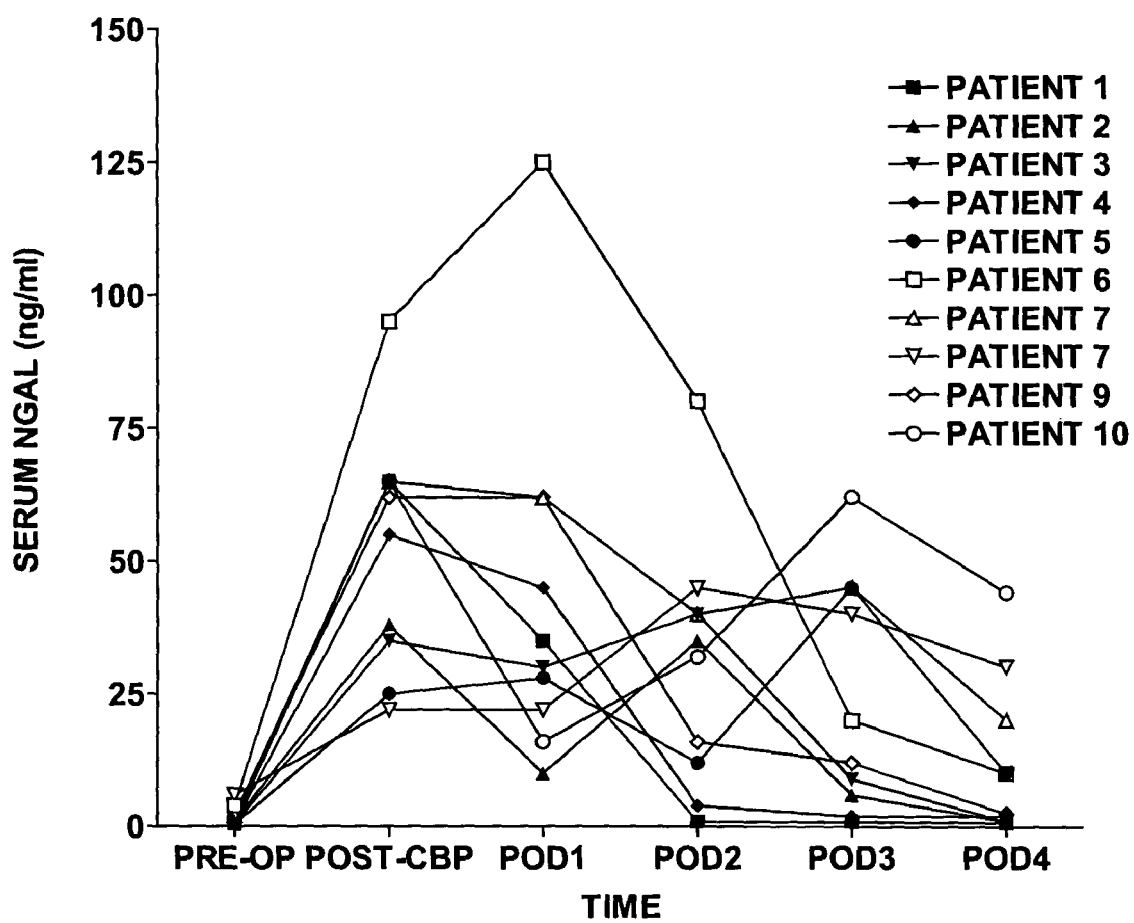
FIG. 25 shows serial serum NGAL measurements in patients who developed ARF following cardiopulmonary bypass during surgery (CPB) (n=10).
Figure 26:
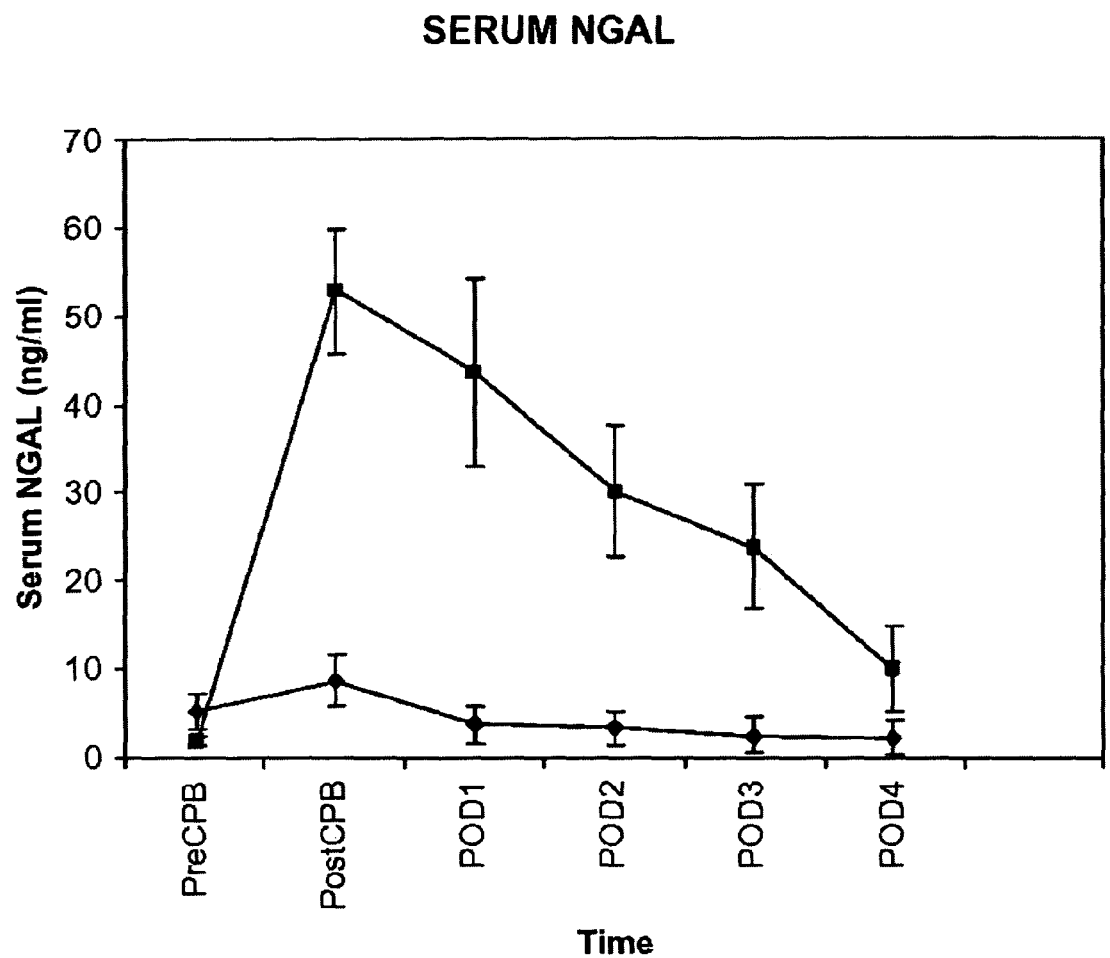
FIG. 26 shows means±SD for serial serum NGAL levels in CBP patients who developed ARF (squares) (n=10) versus those who had an uneventful postoperative course (diamonds) (n=30).
Figure 27:
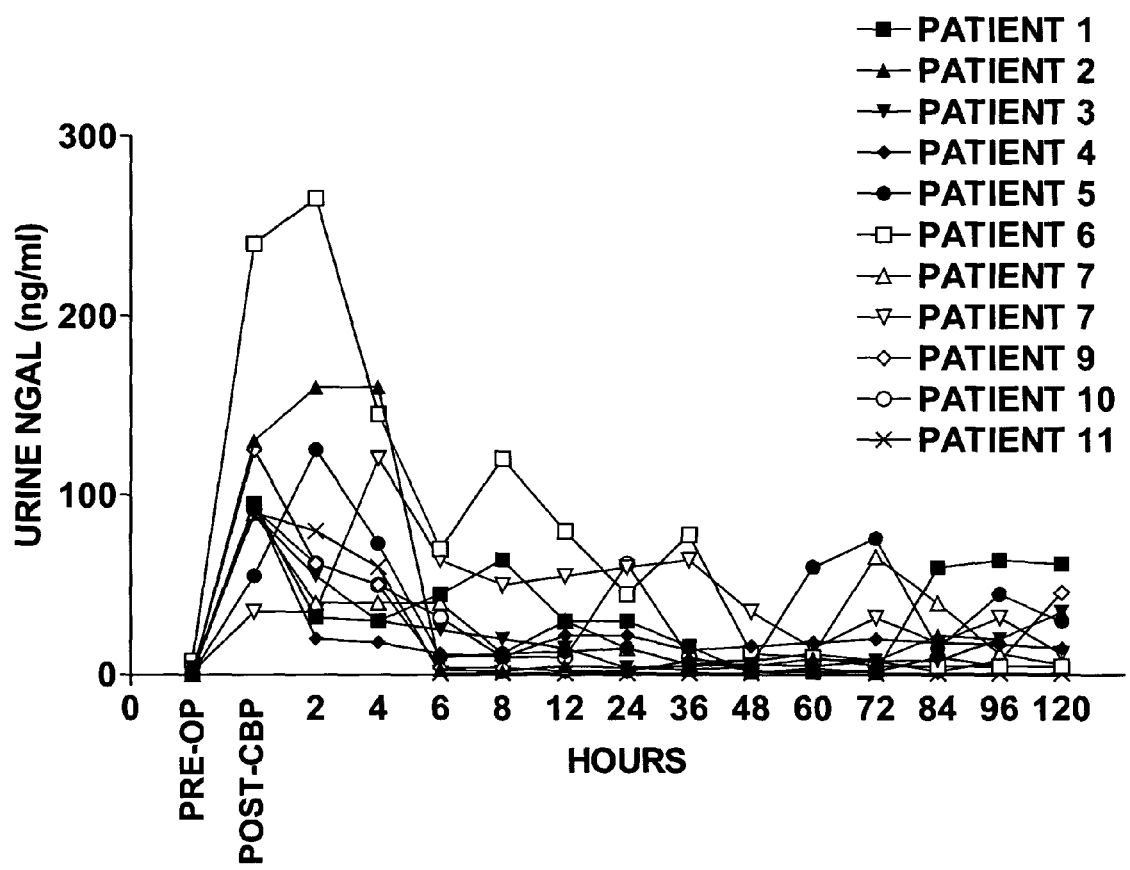
FIG. 27 shows serial urine NGAL measurements in CBP patients who developed ARF following CPB (n=11).
Figure 28:
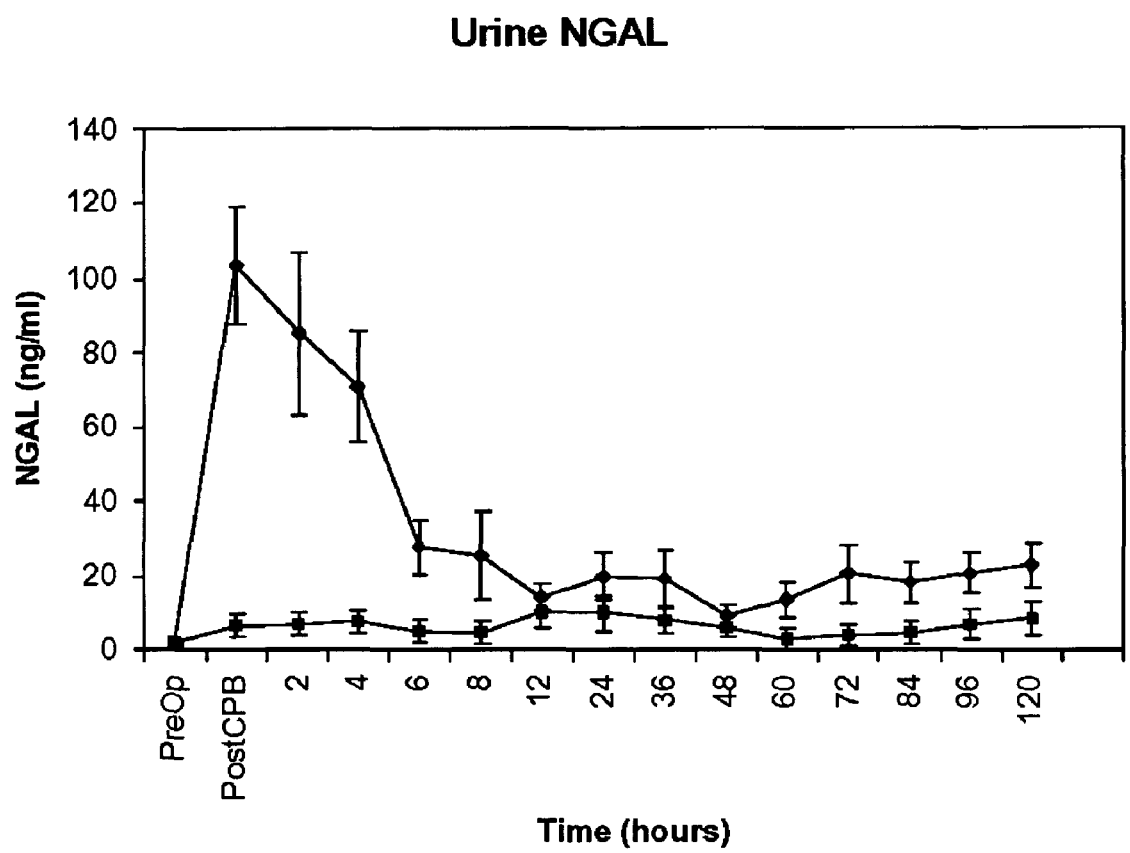
FIG. 28 shows means±SD for serial urine NGAL levels in CBP patients who developed ARF (diamonds) (n=11) versus those who had an uneventful postoperative course (squares) (n=30).
Figure 29:
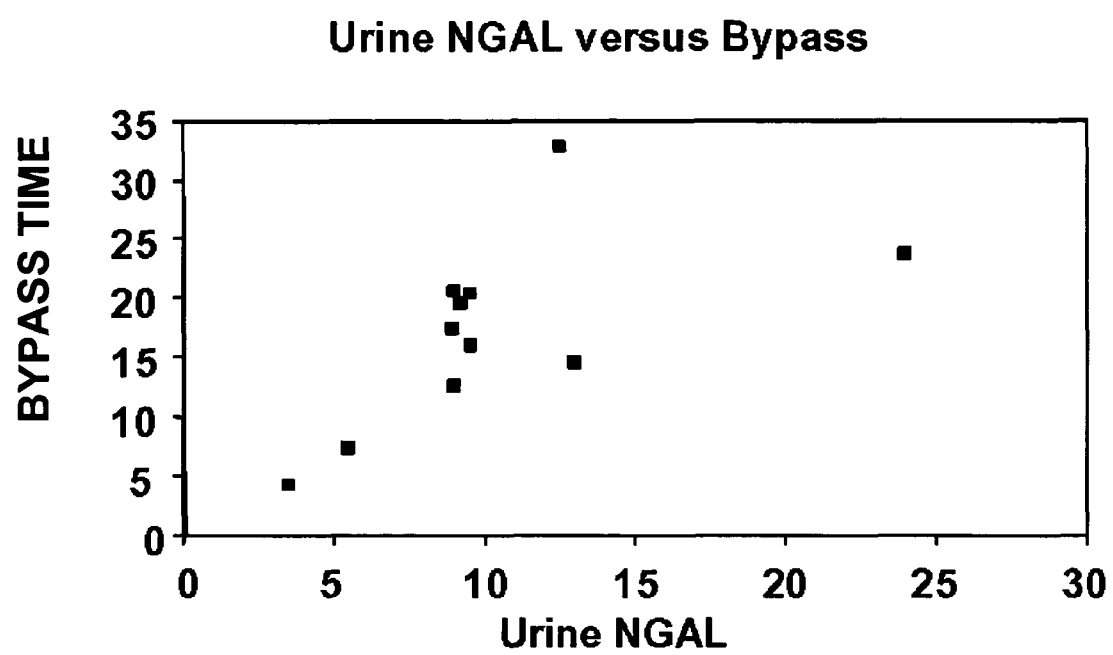
FIG. 29 shows the correlation between urine NGAL levels 2 hours after CPB versus CPB time.

Use of NGAL measurement as a diagnostic tool for Acute Renal Failure. One of the unfortunate outcomes of cardiopulmonary bypass (CPB) during open heart surgery is the development of acute renal failure (ARF). Serum NGAL measurement can be highly predictive for patients who at risk of developing ARF. Standard curves for NGAL ELISA are shown in FIG. 24, the linear relationships obtained from 10 independent standard curves. Serial serum NGAL was measured in samples from patients who developed ARF following CPB (n=10), shown in FIG. 25. NGAL was markedly elevated in samples collected after surgery, and remained elevated for at least 4 days. In contrast, patients who did not develop ARF had no increases in serum NGAL levels during the first 4 post-operative days. FIG. 26 shown means±SD for serial serum NGAL in patients who developed ARF (n=10) versus those who had an uneventful postoperative course (n=30) Serial urine NGAL measurements in patients who developed ARF following CPB (n=11) was also elevated as shown in FIG. 27, but was more variable than serum NGAL. However, urine NGAL levels were predictive of ARF, as shown in FIG. 28, with and analysis of means±SD for serial urine NGAL in patients who developed ARF (n=11) versus those who had an uneventful postoperative course (n=30). Urine NGAL levels at 2 hr postoperative correlated with length of CBP time during surgery, shown in FIG. 29.

While the present invention has been illustrated by the description of embodiments and examples thereof, and while the embodiments and examples have been described in considerable detail, it is not intended to restrict or in any way limit the scope of the appended claims to such detail. Additional advantages and modifications will be readily apparent to those skilled in the art. The invention in its broader aspects is therefore not limited to the specific details, representative methods and structures, and illustrated examples shown and described. Accordingly, departures can be made from such details without departing from the scope or spirit of the invention.

We claim:

1. A method of treating, reducing, or ameliorating a renal injury selected from the group consisting of an ischemic renal injury and an ischemic-reperfusion renal injury to a kidney, comprising the step of administering exogenous neutrophil gelatinase-associated lipocalin (NGAL) in an amount effective to treat, reduce or ameliorate the renal injury to the kidney.

2. The method according to claim 1, wherein the kidney is transplanted into a patient, and the NGAL is administered to a cadaverous or a living donor kidney prior to transplant of the kidney into the patient.

3. The method according to claim 2, wherein NGAL is administered to the patient prior to, during, or following transplant of the kidney.

4. The method according to claim 2 wherein the exogenous NGAL is administered using an organ preservation solution comprising NGAL.

5. The method according to claim 4 wherein the exogenous NGAL is administered using an organ preservation solution comprising at least 0.1 µg NGAL/µL solution.

6. The method according to claim 5 wherein the organ preservation solution comprises at least 1 µg NGAL/µL solution.

7. The method according to claim 5 wherein the organ preservation solution further comprises a siderophore.

8. The method according to claim 7, wherein the NGAL and siderophore are co-administered as a complexed compound of NGAL and the siderophore.

9. The method according to claim 1, wherein the NGAL is administered intravenously or parenterally.

10. The method according to claim 1, wherein the renal injury is associated with conditions, treatments, therapies, or diseases that predispose a patient to the ischemic renal injury.

11. The method according to claim 1, wherein the renal injury results from a condition, treatment, or therapy selected from the group consisting of contrast agent treatment, antibody treatment, antibiotic treatment, organ transplant, kidney transplant, cadaveric kidney transplant, cardiac treatment, cardiac treatment after surgery, and central nervous system treatment.

12. The method according to claim 1, wherein the renal injury results from a condition, treatment, therapy, or disease selected from the group consisting of infection, bacterial infection, kidney disease, ischemic-reperfusion injury, cardiac reperfusion injury, cardiopulmonary bypass surgery, open heart surgery, and abdominal surgery.

13. The method according to claim 1, wherein the injury is an ischemia-reperfusion injury to a kidney, and NGAL administration ameliorates a reduction in kidney function.

14. The method according to claim 1, further comprising the step of administering to the patient a siderophore in an amount effective to enhance the treating, reducing, or ameliorating of the renal injury by NGAL.

15. The method according to claim 14, wherein NGAL and the siderophore are co-administered as a complexed compound of NGAL and the siderophore.

16. The method according to claim 1 wherein the step of administering comprises administering a composition comprising NGAL, in an amount effective to treat, reduce, or ameliorate the renal injury to the kidney.

17. The method according to claim 16, wherein the composition comprises at least 10 microgram NGAL per 100 microliter of composition.

18. The method according to claim 17, wherein the composition further comprising a siderophore.

19. The method according to claim 18, wherein the NGAL and siderophore are co-administered as a complexed compound of NGAL and the siderophore.

20. The method according to claim 1 wherein the renal injury is an ischemic-reperfusion injury to a kidney transplant in a patient, and wherein the step of administering NGAL comprises administering the exogenous NGAL to (i) the kidney transplant, (ii) a donor of the kidney transplant, or (iii) both (i) and (ii), in an amount of NGAL effective to reduce or ameliorate delayed graft function (DGF) or rejection of the kidney transplant.

21. The method according to claim 20 wherein the kidney transplant is a cadaveric or living donor kidney.

22. The method according to claim 20, further comprising the step of administering to the patient a siderophore in an amount effective to enhance the reducing or ameliorating of the ischemic-reperfusion injury effected by NGAL.

23. The method according to claim 22, wherein NGAL and the siderophore are co-administered as a complexed compound of NGAL and the siderophore.

* * * * *

```
                         SEQUENCE LISTING

<160> NUMBER OF SEQ ID NOS: 4

<210> SEQ ID NO 1
    <211> LENGTH: 20
    <212> TYPE: DNA
    <213> ORGANISM: Murinae gen. sp.

<400> SEQUENCE: 1
ctcagaactt gatccctgcc                                              20

<210> SEQ ID NO 2
    <211> LENGTH: 20
    <212> TYPE: DNA
    <213> ORGANISM: Murinae gen. sp.

<400> SEQUENCE: 2
tccttgaggc ccagagactt                                              20

<210> SEQ ID NO 3
    <211> LENGTH: 20
    <212> TYPE: DNA
    <213> ORGANISM: Murinae gen. sp.

<400> SEQUENCE: 3
ctaaggccaa ccgtgaaaag                                              20

<210> SEQ ID NO 4
    <211> LENGTH: 20
    <212> TYPE: DNA
    <213> ORGANISM: Murinae gen. sp.

<400> SEQUENCE: 4
tctcagctgr ggrggrgaag                                              20
```